(12) United States Patent
Thompson

(10) Patent No.: US 11,453,621 B2
(45) Date of Patent: Sep. 27, 2022

(54) ISOBARIC MASS LABELS HAVING N',N'-DIMEIHYL PIPERAZINE-2-CARBOXYLIC ACID REPORTER MOIETIES

(71) Applicant: ELECTROPHORETICS LIMITED, London (GB)

(72) Inventor: Andrew Hugin Thompson, Cambridge (GB)

(73) Assignee: ELECTROPHORETICS LIMITED, London (GB)

(*) Notice: Subject to any disclaimer, the term of this patent is extended or adjusted under 35 U.S.C. 154(b) by 67 days.

(21) Appl. No.: 16/061,136

(22) PCT Filed: Dec. 9, 2016

(86) PCT No.: PCT/EP2016/080534
§ 371 (c)(1),
(2) Date: Jun. 11, 2018

(87) PCT Pub. No.: WO2017/098029
PCT Pub. Date: Jun. 15, 2017

(65) Prior Publication Data
US 2018/0362416 A1 Dec. 20, 2018

(30) Foreign Application Priority Data
Dec. 11, 2015 (GB) .................................... 1521903

(51) Int. Cl.
*G01N 33/58* (2006.01)
*C07B 59/00* (2006.01)
(Continued)

(52) U.S. Cl.
CPC .......... *C07B 59/002* (2013.01); *C07D 403/12* (2013.01); *G01N 33/58* (2013.01);
(Continued)

(58) Field of Classification Search
CPC ....... G01N 33/58; C07B 59/00; C07D 403/12
(Continued)

(56) References Cited

U.S. PATENT DOCUMENTS 5,399,693 A * 3/1995 Watkins ............ C07F 9/650952
544/337
7,294,456 B2 11/2007 Schmidt et al.
(Continued)

FOREIGN PATENT DOCUMENTS

WO     WO 01/68684 A2    9/2001
WO     WO 03/013571 A1    2/2003
(Continued)

OTHER PUBLICATIONS

Nilsson, J. W. et al, Journal of Combinatorial Chemistry 2001, 3, 546-553.*
(Continued)

*Primary Examiner* — Arlen Soderquist
(74) *Attorney, Agent, or Firm* — ArentFox Schiff LLP

(57) ABSTRACT

The present invention relates to a set of two or more mass labels, wherein each mass label comprises the formula:

X-L-M-Re wherein X is a reporter moiety having an exact mass, L is a bond cleavable by collision in a mass spectrometer, M is a mass modifier, and Re is a) a reactive functionality for attaching the mass label to an analyte or b) the analyte, wherein each mass label in the set has an integer mass, wherein each mass label in the set has the same integer mass, and wherein the set comprises two or more subsets of mass labels, each subset comprising one, two or more mass labels, and wherein, when the subset comprises two or more mass labels, the exact mass of the reporter moiety X of each mass label in the subset is different from the exact mass of the reporter moiety X of the mass labels in the same subset and (Continued)

in all other subsets, and wherein each mass label is distinguishable by mass spectrometry.

16 Claims, 11 Drawing Sheets

(51) Int. Cl.
*C07D 403/12* (2006.01)
*G01N 33/68* (2006.01)
*C12Q 1/6872* (2018.01)
*C40B 40/04* (2006.01)

(52) U.S. Cl.
CPC ...... *G01N 33/6893* (2013.01); *C07B 2200/05* (2013.01); *C12Q 1/6872* (2013.01); *C40B 40/04* (2013.01); *G01N 2458/15* (2013.01); *G01N 2560/00* (2013.01)

(58) Field of Classification Search
USPC ...................................... 436/86–87, 94, 173
See application file for complete search history.

(56) References Cited

U.S. PATENT DOCUMENTS

| | | | | |
|---|---|---|---|---|
| 8,697,604 | B2* | 4/2014 | Hamon | C07C 229/12 506/13 |
| 10,527,629 | B2* | 1/2020 | Thompson | C12Q 1/6872 |
| 2004/0106802 | A1 | 6/2004 | Sankaranarayanan | |
| 2004/0157264 | A1 | 8/2004 | Sharma et al. | |
| 2004/0219685 | A1* | 11/2004 | Pappin | C07D 401/12 436/173 |
| 2004/0220412 | A1* | 11/2004 | Pappin | G01N 33/532 548/542 |
| 2005/0148087 | A1* | 7/2005 | Pappin | C07D 295/037 436/86 |
| 2005/0148771 | A1* | 7/2005 | Dey | C07D 207/46 544/182 |
| 2005/0153456 | A1* | 7/2005 | Pappin | G01N 33/6848 436/166 |
| 2007/0023628 | A1* | 2/2007 | Hamon | C07C 229/12 250/282 |
| 2007/0218560 | A1* | 9/2007 | Pillai | C07D 295/15 436/86 |
| 2008/0014642 | A1* | 1/2008 | Purkayastha | C07C 269/02 436/56 |
| 2008/0241955 | A1* | 10/2008 | Purkayastha | C07D 295/15 436/173 |
| 2008/0287453 | A1* | 11/2008 | Bower | A61P 1/02 514/252.11 |
| 2010/0068819 | A1* | 3/2010 | Hoffmann | G01N 33/6848 436/86 |
| 2010/0178710 | A1* | 7/2010 | Hamon | C07D 207/404 436/173 |
| 2011/0003395 | A1* | 1/2011 | Dey | G01N 30/72 436/98 |
| 2011/0028685 | A1* | 2/2011 | Purkayastha | C07D 493/10 530/300 |
| 2011/0143951 | A1* | 6/2011 | Thompson | C12Q 1/6816 506/7 |
| 2011/0172115 | A1* | 7/2011 | Thompson | H01J 49/0004 506/9 |
| 2011/0292388 | A1* | 12/2011 | Manka | G01N 21/211 356/364 |
| 2011/0318771 | A1* | 12/2011 | Li | G01N 33/6848 435/27 |
| 2012/0196378 | A1* | 8/2012 | Purkayastha | C07D 295/14 436/98 |
| 2013/0078728 | A1* | 3/2013 | Li | C07D 207/46 436/86 |
| 2013/0184181 | A1* | 7/2013 | Purkayastha | C07D 493/10 506/12 |
| 2013/0309689 | A1 | 11/2013 | Rogers et al. | |
| 2016/0139140 | A1* | 5/2016 | Thompson | C07D 403/12 506/4 |
| 2017/0045526 | A1* | 2/2017 | Thompson | G01N 33/6848 |
| 2017/0146549 | A1* | 5/2017 | Thompson | G01N 33/6848 |

FOREIGN PATENT DOCUMENTS

| | | | |
|---|---|---|---|
| WO | 2006002841 A2 | 1/2006 | |
| WO | WO 2007/012849 A2 | 2/2007 | |
| WO | WO 2007/087534 A2 | 8/2007 | |
| WO | WO 2011/036059 A1 | 3/2011 | |
| WO | 2013138210 A1 | 9/2013 | |
| WO | 2013170067 A1 | 11/2013 | |
| WO | WO 2015/091876 A1 | 8/2015 | |
| WO | WO 2015/189413 A | 12/2015 | |
| WO | WO 03/084940 A1 | 1/2016 | |

OTHER PUBLICATIONS

Pace, P. et al, Journal of Medicinal Chemistry 2007, 50, 2225-2239.*
Guitot, K. et al, Journal of Organic Chemistry 2009, 74, 8433-8436.*
Xiang, F. et al, Analytical Chemistry 2010, 82, 2817-2825.*
Palomo, C. et al, Tetraheron Letters 1997, 38, 4643-4646.*
Breitenbucher, J. G. et al, Tetraheron Letters 1998, 39, 1295-1298.*
Herpin, T. F. et al, Molecular Diversity 1998, 4, 221-232.*
Ross. P. L. et al, Molecular & Cellular Proteomics 2004, 3, 1154-1169.*
Schmidt, A. et al, Proteomics 2005, 5, 4-15.*
Catalano, A. et al, European Journal of Medicinal Chemistry 2008, 43, 2535-2540.*
Phanstiel, D. et al, Journal of the American Society for Mass Spectrometry 2008, 19, 1255-1262.*
Ottesen,, L. K. et al, Chemistry A European Journal 2009, 15, 2966-2978.*
Zeng, D. et al, Bioorganic & Medicinal Chemistry Letters 2009, 19, 2059-2061.*
International Preliminary Report on Patentability and Written Opinion of the International Searching Authority issued in PCT/EP2016/080534, dated Jun. 12, 2018, pp. 1-6.
Office Action issued in European Patent Application No. 16816622.1, dated Sep. 26, 2019, pp. 1-5.
Andrews et al.; "Performance Characteristics of a New Hybrid Triple Quadrupole Time-of-Flight Tandem Mass Spectrometer"; Anal. Chem. Jul. 1, 2011; 83(13); pp. 5442-5446.
Arnold et al.; "Conversion of Serine to Stereochemically Pure β-Substituted α-Amino Acids via β-Lactones"; J. Am. Chem. Soc. 1985, vol. 107, No. 24, pp. 7105-7109.
Dess et al.; "Readily Accessible Dec. 1, 1951 Oxidant for the Conversion of Primary and Secondary Alcohols to Aldehydes and Ketones"; J. Org. Chem. 1983, 48, pp. 4155-4156.
GB Search Report issued for GB1521903.3, dated Nov. 11, 2016 (16 pages).
Goddard-borger et al.; "An Efficient Inexpensive, and Shelf-Stable Dlazotransfer Reagent: Imidazole-1-sulfonyl Azide Hydrochloride"; Organic Letters, 2007, vol. 9, No. 19, pp. 3797-3800.
Gygi et al.; "Quantitative analysis of complex protein mixtures using isotope-coded affinity tags"; Nature Biotechnology, vol. 17, Oct. 1999; pp. 994-999.
Hebert et al.; "Neutron-encoded mass signatures for multi-plexed proteome quantification"; Nat. Methods, Apr. 2013, 10(4), pp. 332-334.
Hu et al.; "The Orbitrap: a new mass spectrometer"; Journal of Mass Spectrometry, 2005, 40, pp. 430-443.
International Search Report issued for PCT/EP2016/080534, dated Feb. 24, 2017.
Lee et al; "Selective Mono-BOC Protection of Diamines"; Synthetic Communications, 37, 2007, pp. 737-742.
Makarov; "Electrostatic Axially Harmonic Orbital Trapping: A High-Performance Technique of Mass Analysis"; Analytical Chemistry, 2000, vol. 72, No. 6, pp. 1156-1162.

(56) References Cited

OTHER PUBLICATIONS

Marshall et al.; "Fourier Transform Ion Cyclotron Resonance Mass Spectrometry: A Primer"; Mass Spectrometry Reviews, 1998, 17, pp. 1-35.
Marshall et al.; "High-Resolution Mass Spectrometers"; Annu. Rev. Anal. Chem. 2008, 1, pp. 579-599.
McAlister et al.; "Increasing the Multiplexing Capacity of TMTs Using Reporter Ion Isotopologues with Isobaric Masses"; Anal. Chem. 2012, 84, pp. 7469-7478.
Okumura et al.; "High-resolution time-of-flight spectra obtained using the Multum II muiti-turn type time-of-flight mass spectrometer with an electron ionization ion source"; Eur. J. Mass Spectrum, 11, 2005, pp. 261-266.
Pedregal et al.; "Highly Chemoselective Reduction of N-Boc Protected Lactams"; Tetrahedron Letters, vol. 35, No. 13, 1994, pp. 2053-2056.
Ratemi et al.; "Reaction of Trimethylsilylamines with N-Cbz-L-Serine-βLactone: A Convenient Route to Optically Pure β-Amino-L-alanine Derivatives"; Tetrahedron Letters, vol. 35, No. 41, pp. 7605-7608, 1994.
Rostovtsev et al.; "A Stepwise Huisgen Cycloaddition Process: Copper(I)-Catalyzed Regioselective "Ligation" of Azides and Terminal Alkynes**"; Angew. Chem. Int. Ed. 2002, 41, No. 14, pp. 2596-2599.
Schaub et al.; "High-Performance Mass Spectrometry: Fourier Transform Ion Cyclotron Resonance at 14.5 Tesla"; Anal. Chem. 2008, 80, pp. 3985-3990.
Shimma et al.: "Detailed Structural Analysis of Lipids Directly on Tissue Specimens Using a MALDI-SpiralTOF-Reflection TOF Mass Spectrometer"; PLoS One 7(5): e37107, 2012, (8 pages).
Warshawsky et al.; "Synthesis of N,N-Orthogonally Protected (S)-Piperazine-2-carboxylic Acid"; J. Org. Chem. 1997, 62, pp. 6439-6440.
Werner et al.; "High-Resolution Enabled TMT 8-plexing"; Anal. Chem. 2012, 84, pp. 7188-7194.
Chinese Office Action issued for Chinese Application No. 201680078597, dated Jan. 27, 2021 (15 pages), English translation of Text of the First Office Action (12 pages).
Chinese Office Action issued for CN 201680078597.9, dated Office Action Oct. 9, 2021 (English translation of Text of Second OA).
Canadian Office Action issued for CA Application No. 3,007,430, dated Office Action Mar. 10, 2022 (5 pps).
Chinese Office Action issued for Chinese Application No. 201680078597.9, date of Chinese Office Action Mar. 17, 2022, dated Apr. 24, 2022 (English translation of text only).

* cited by examiner a)
Serine isotopes:
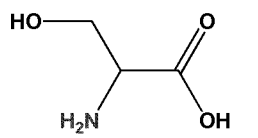 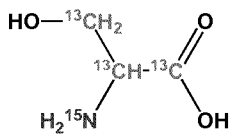 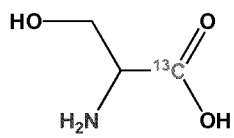 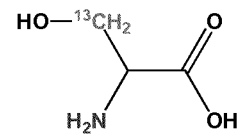
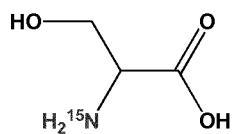 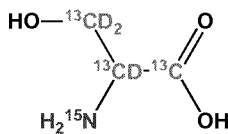 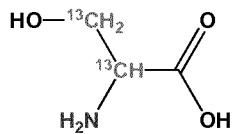 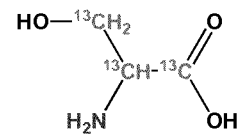
Ethanolamine Isotopes
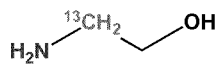 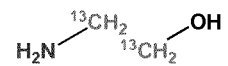 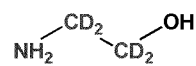 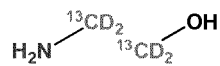
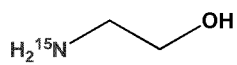 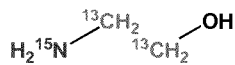
Formaldehyde Isotopes:
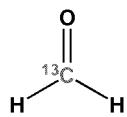 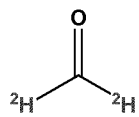 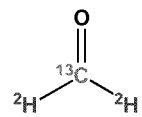
Threonine isotopes:
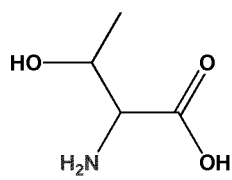 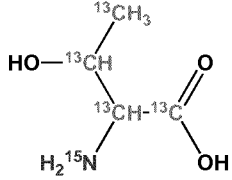 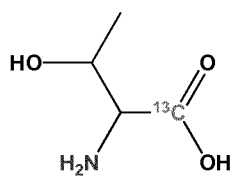 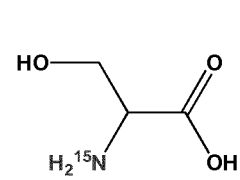
Figure 6 b)
Alanine isotopes:
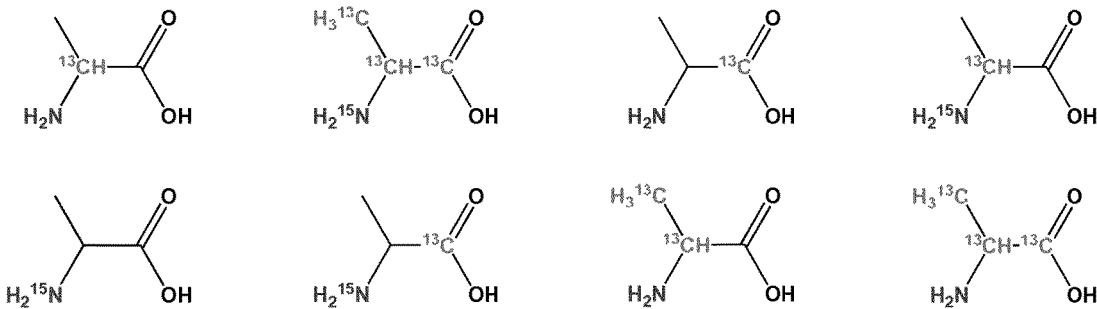
Valine isotopes:
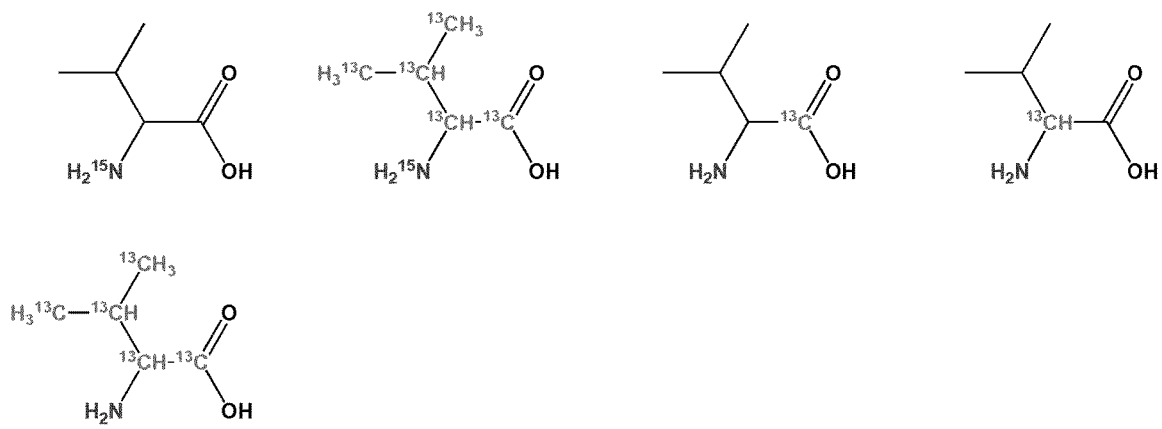
Leucine isotopes:
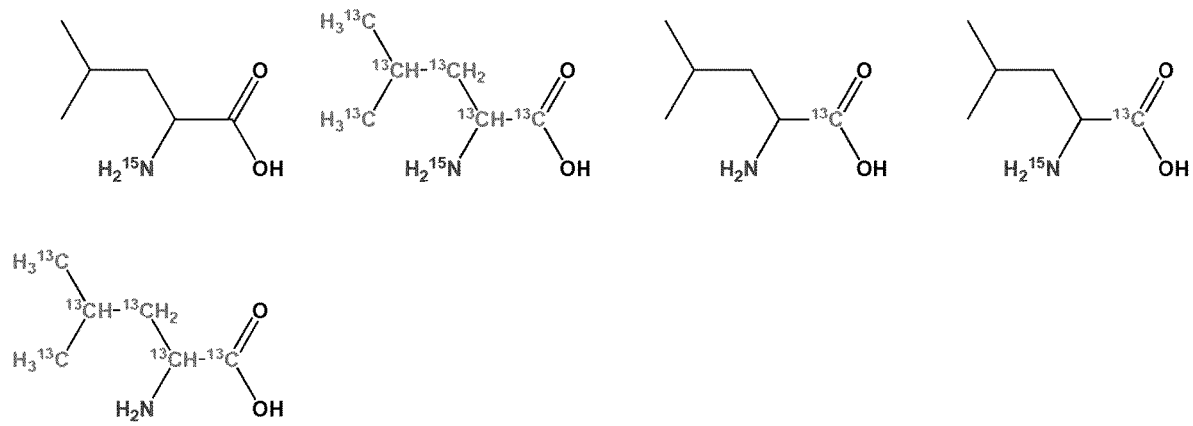
Figure 6 (cont.)

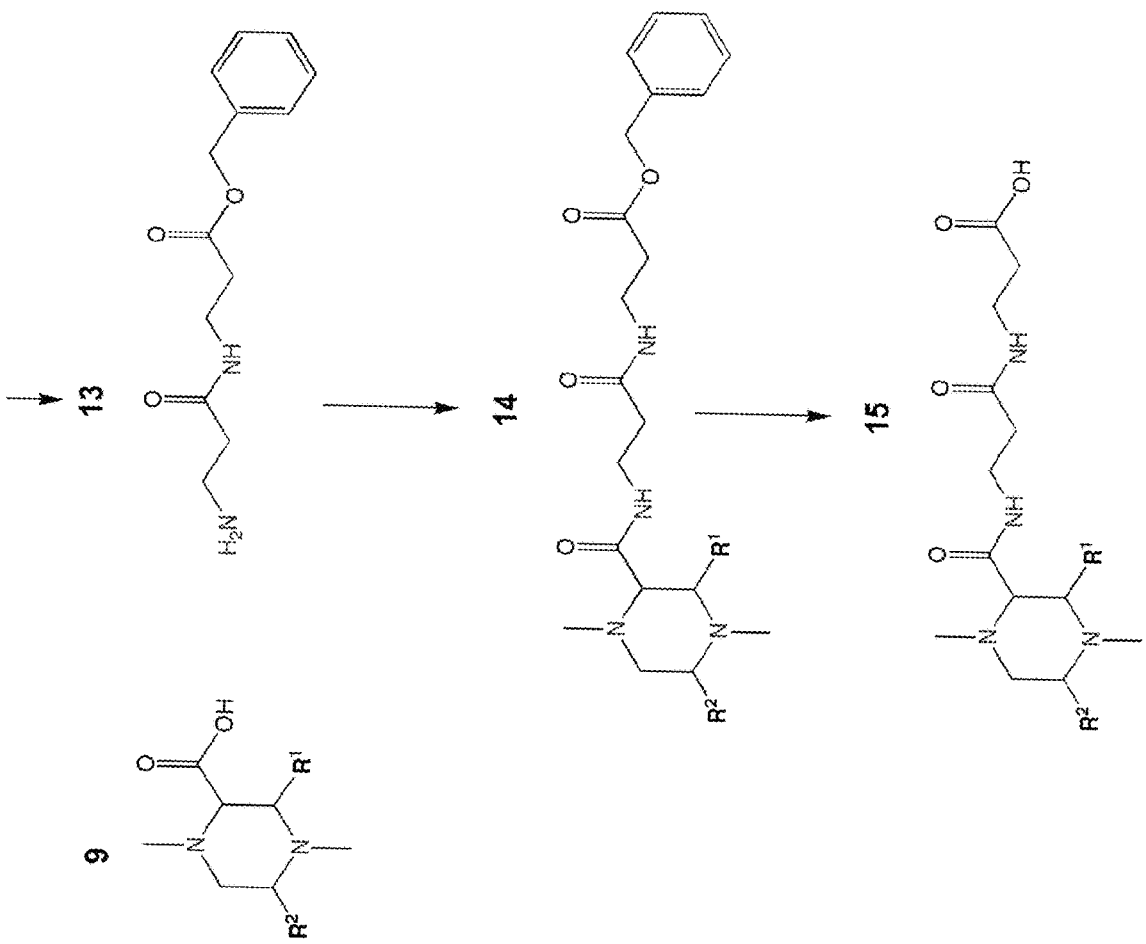

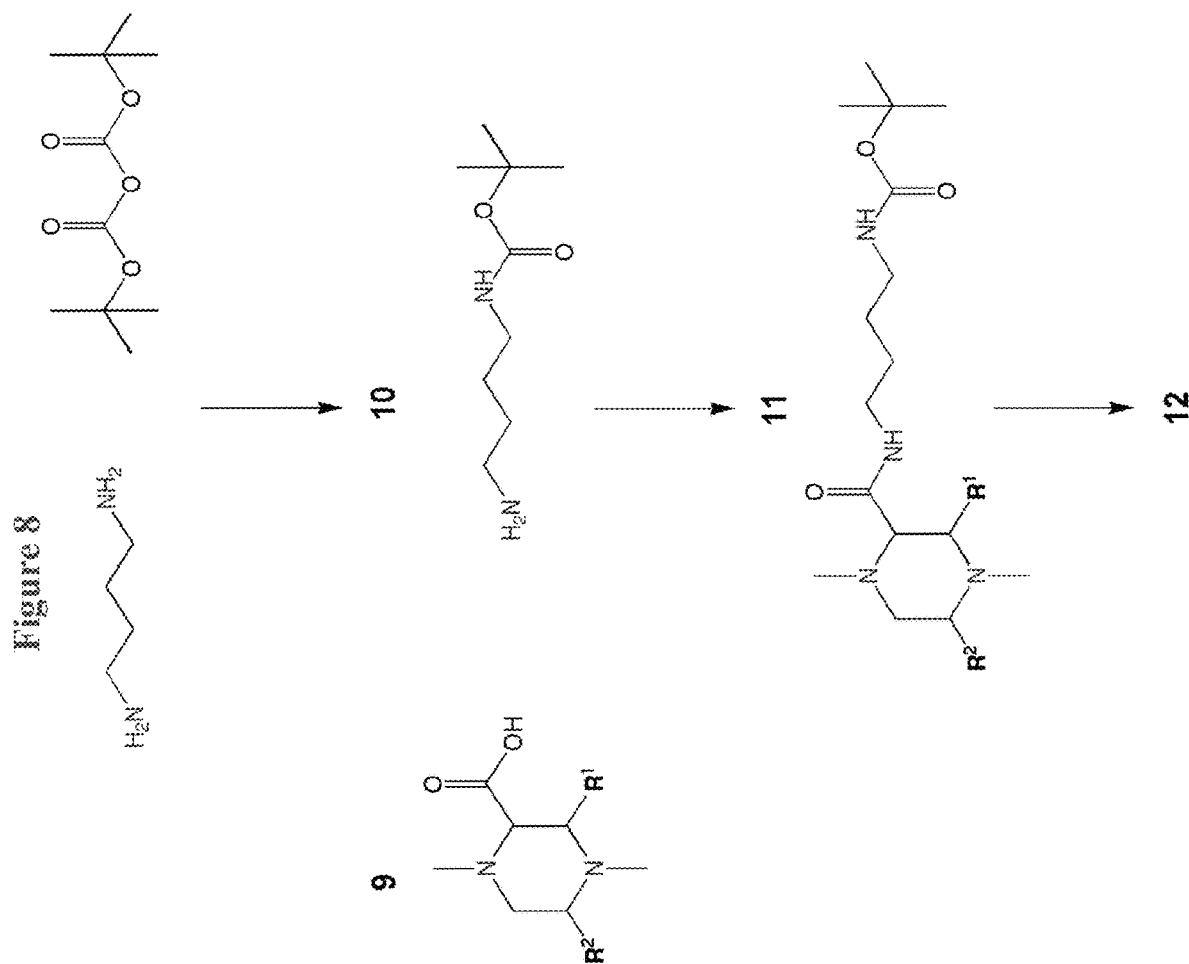

ISOBARIC MASS LABELS HAVING N',N'-DIMEIHYL PIPERAZINE-2-CARBOXYLIC ACID REPORTER MOIETIES

CROSS-REFERENCE TO RELATED APPLICATIONS

This application is the U.S. National Stage Application of International Patent Application No. PCT/EP2016/080534 filed on Dec. 9, 2016, which claims priority to GB Application No. 1521903.3, filed on Dec. 11, 2015, the contents of each of which is incorporated herein by reference in its entirety.

FIELD OF THE INVENTION

This invention relates to useful reactive labels for labelling peptides and to methods for using these reactive labels, to identify and quantify peptides particularly peptides derived from complex protein mixtures. These reactive labels are of particular value for the analysis of peptides by high resolution and high mass accuracy mass analysers such as orbitraps, time-of-flight and ion cyclotron resonance mass analysers.

BACKGROUND OF THE INVENTION

The study of biological systems and particularly the understanding of human disease is dependent on the ability to detect changes caused in biological systems by or in response to a disease. Such changes provide means of diagnosis and offer insights into the targets for therapeutic compounds such as vaccines and medicines. A wide range of biological molecules need to be measured quantitatively to understand disease processes including nucleic acids, proteins, steroids, sugars and lipids. In this context, the ability to quantitatively detect such biomolecules using mass spectrometers has provided considerable advances in their study and application to human and also to veterinary disease. The same advances have also occurred in environmental analysis and monitoring, and in food and beverage manufacturing. In particular the use of stable isotopes to provide synthetic quantitative references has been developed in isotope dilution mass spectrometry for monitoring of all classes of biomolecules. However, these methods have traditionally required an available synthetic standard, which is not always possible.

Recently, a range of chemical mass tags bearing heavy isotope substitutions have been developed to further improve the quantitative analysis of biomolecules by mass spectrometry. Depending on the tag design, members of tag sets are either isotopic having the same chemical structure but different absolute masses, or isobaric and isotopomeric, having both identical structure and absolute mass. Isotopic tags are typically used for quantification in MS mode whilst isobaric tags must be fragmented in MS/MS mode to release reporter fragments with a unique mass.

An early example of isotopic mass tags were the Isotope-Coded Affinity Tags (ICAT) (Gygi, S. P. et al., (1999) *Nat Biotechnol,* 17, 994-999). The ICAT reagents are a pair of mass tags bearing a differential incorporation of heavy isotopes in one (heavy) tag with no substitutions in the other (light) tag. Two samples are labelled with either the heavy or light tag and then mixed prior to analysis by LC-MS. A peptide present in both samples will give a pair of precursor ions with masses differing in proportion to the number of heavy isotope atomic substitutions.

The ICAT method also illustrates 'sampling' methods, which are useful as a way of reconciling the need to deal with small populations of peptides to reduce the complexity of the mass spectra generated while retaining sufficient information about the original sample to identify its components. The 'isotope encoded affinity tags' used in the ICAT procedure comprise a pair of biotin linker isotopes, which are reactive to thiols, for the capture peptides comprising cysteine. Typically 90 to 95% or proteins in a proteome will have at least one cysteine-containing peptide and typically cysteine-containing peptides represent about 1 in 10 peptides overall so analysis of cysteine-containing peptides greatly reduces sample complexity without losing significant information about the sample. Thus, in the ICAT method, a sample of protein from one source is reacted with a 'light' isotope biotin linker while a sample of protein from a second source is reacted with a 'heavy' isotope biotin linker, which is typically 4 to 8 Daltons heavier than the light isotope. The two samples are then pooled and cleaved with an endopeptidase. The biotinylated cysteine-containing peptides can then be isolated on avidinated beads for subsequent analysis by mass spectrometry. The two samples can be compared quantitatively: corresponding peptide pairs act as reciprocal standards allowing their ratios to be quantified. The ICAT sampling procedure produces a mixture of peptides that still accurately represents the source sample while being less complex than MudPIT, but large numbers of peptides are still isolated and their analysis by LC-MS/MS generates complex spectra. With 2 ICAT tags, the number of peptide ions in the mass spectrum is doubled compared to a label-free analysis.

Further examples of isotopic tags include the ICPL reagents that provide up to four different reagents, and with ICPL the number of peptide ions in the mass spectrum is quadrupled compared to a label-free analysis. For this reason, it is unlikely to be practical to develop very high levels of multiplexing with simple heavy isotope tag design.

Whilst isotopic tags allow quantification in proteomic studies and assist with experimental reproducibility, this is achieved at the cost of increasing the complexity of the mass spectrum. To overcome this limitation, and to take advantage of greater specificity of tandem mass spectrometry isobaric mass tags were developed. Since their introduction in 2000 (WO01/68664), isobaric mass tags have provided improved means of proteomic expression profiling by universal labelling of amines and other reactive functions in proteins and peptides prior to mixing and simultaneous analysis of multiple samples. Because the tags are isobaric, having the same mass, they do not increase the complexity of the mass spectrum since all precursors of the same peptide will appear at exactly the same point in the chromatographic separation and have the same aggregate mass. Only when the molecules are fragmented prior to tandem mass spectrometry are unique mass reporters released, thereby allowing the relative or absolute amount of the peptide present in each of the original samples to be determined.

WO01/68664 sets out the underlying principles of isobaric mass tags and provides specific examples of suitable tags wherein different specific atoms within the molecules are substituted with heavy isotope forms including $^{13}C$ and $^{15}N$ respectively. WO01/68664 further describes the use of offset masses to make multiple isobaric sets to increase the overall multiplexing rates available without unduly increasing the size of the individual tags.

WO2007/012849 describes further sets of isobaric mass tags including 3-[2-(2,6-Dimethyl-piperidin-1-yl)-acetylamino]-propanoic acid-(2,5-dioxo-pyrrolidin-1-yl)-ester (DMPip-βAla-OSu).

Recently, with dramatic improvements in mass accuracy and mass resolution enabled by high mass resolution mass spectrometers such as the Orbitrap (Hu, Q. et al., (2005) *J Mass Spectrom*, 40, 430-443 & Makarov, A. (2000) *Anal Chem*, 72, 1156-1162), Fourier Transform Ion Cyclotron Resonance (FT-ICR) mass spectrometers (Marshall, A. G. et al., (1998) *Mass Spectrom Rev*, 17, 1-35) and high resolution Time-of-Flight (TOF) mass spectrometers (Andrews, G. L. et al., (2011) *Anal Chem*, 83, 5442-5446), it has become possible to resolve millidalton differences between ion mass-to-charge ratios. This high resolution capability has been exploited to increase multiplexing of Isobaric Tandem Mass Tags using heavy nucleon substitutions of $^{13}C$ for $^{15}N$ in the reporter region which results in 6.32 millidalton differences between the respective reporter fragments upon analysis by MS/MS (McAlister, G. C. et al., (2012) *Anal Chem*, 84, 7469-7478 & Werner, T. et al., (2012) *Anal Chem*, 84, 7188-7194). Similarly, it has been shown that metabolic labelling with lysine isotopes comprising millidalton mass differences can be resolved by high-resolution mass spectrometry enabling multiplexing and relative quantification of samples in yeast (Hebert, A. S. et al., (2013) *Nat Methods*, 10, 332-334).

Despite the significant benefits of previously disclosed isobaric mass tags, the multiplexing rate has been limited to 10-plex in commercial reagents to date. In addition, tags comprising very small mass differences would be useful because labelled ions that are related to each other, e.g. corresponding peptides from different samples, would cluster closely in the same ion envelope with very distinctive and unnatural isotope patterns that would be readily recognisable and which will be much less likely to interfere with the identification of other different peptides.

Hence, there still remains the need for sets of tags, where each tag differs from the others by millidalton mass differences, for labelling peptides and biomolecules with multiplexing rates greatly in excess of 10-fold.

BRIEF DESCRIPTION OF THE INVENTION

In a first aspect, the present invention relates to a set of two or more mass labels, wherein each mass label comprises the formula:

X-L-M-Re wherein:
X is a reporter moiety having an exact mass,
L is a bond cleavable by collision in a mass spectrometer,
M is a mass modifier, and
Re is a) a reactive functionality for attaching the mass label to an analyte or b) the analyte,
wherein each mass label in the set has an integer mass, wherein each mass label in the set has the same integer mass, wherein the set comprises two or more subsets of mass labels, each subset comprising one, two or more mass labels, wherein, when the subset comprises two or more mass labels, the exact mass of the reporter moiety X of each mass label in the subset is different from the exact mass of the reporter moiety X of the mass labels in the same subset and in all other subsets, wherein each mass label is distinguishable by mass spectrometry, wherein each mass label has a reporter moiety X comprising the following general formula:

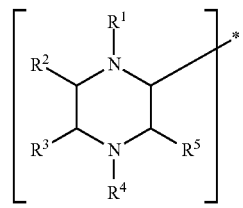

wherein each of $R^1$, $R^2$, $R^3$, $R^4$ and $R^5$ is independently H, a substituted or unsubstituted straight or branched $C_1$-$C_{10}$ alkyl group; or a structure selected from methyl, ethyl, propyl or n-propyl, isopropyl, butyl or n-butyl, isobutyl, sec-butyl, tert-butyl, pentyl or n-pentyl, neopentyl, tert-pentyl, iso-pentyl, sec-pentyl and 3-pentyl.

In another aspect, the present invention relates to a set of two or more mass labels, wherein each label comprises the formula:

X-L-M-Re wherein X is a reporter moiety having an exact mass, L is a bond cleavable by collision in a mass spectrometer, M is a mass modifier, and Re is a reactive functionality for attaching the mass label to an analyte or the analyte, and X comprises the following general formula:

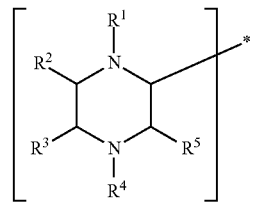

wherein each of $R^1$, $R^2$, $R^3$, $R^4$ and $R^5$ is independently H, a substituted or unsubstituted straight or branched $C_1$-$C_{10}$ alkyl group, or a structure selected from methyl, ethyl, propyl or n-propyl, isopropyl, butyl or n-butyl, isobutyl, sec-butyl, tert-butyl, pentyl or n-pentyl, neopentyl, tert-pentyl, iso-pentyl, sec-pentyl and 3-pentyl.

In another aspect, the present invention relates to an array of mass labels, comprising two or more sets of mass labels according to the invention.

In another aspect, the present invention relates to a method of mass spectrometry analysis, which method comprises detecting an analyte by identifying by mass spectrometry a mass label or combination of mass labels relatable to the analyte, wherein the mass label is a mass label from a set or array of mass labels according to the invention.

BRIEF DESCRIPTION OF THE DRAWINGS

FIG. 6: Examples of commercially available heavy isotope doped precursors that are useful for the synthesis of the mass tags of this invention. glycine, bromoacetic acid and an alkylamine such as methylamine can be used to synthesise N-alkylpiperazine. FIG. 6a illustrates examples of heavy isotopes of serine, ethanolamine, formaldehyde and threonine while FIG. 6b illustrates examples of heavy isotopes of alanine, valine and leucine.

DETAILED DESCRIPTION OF THE INVENTION

Sets of Mass Labels

Figure 1:
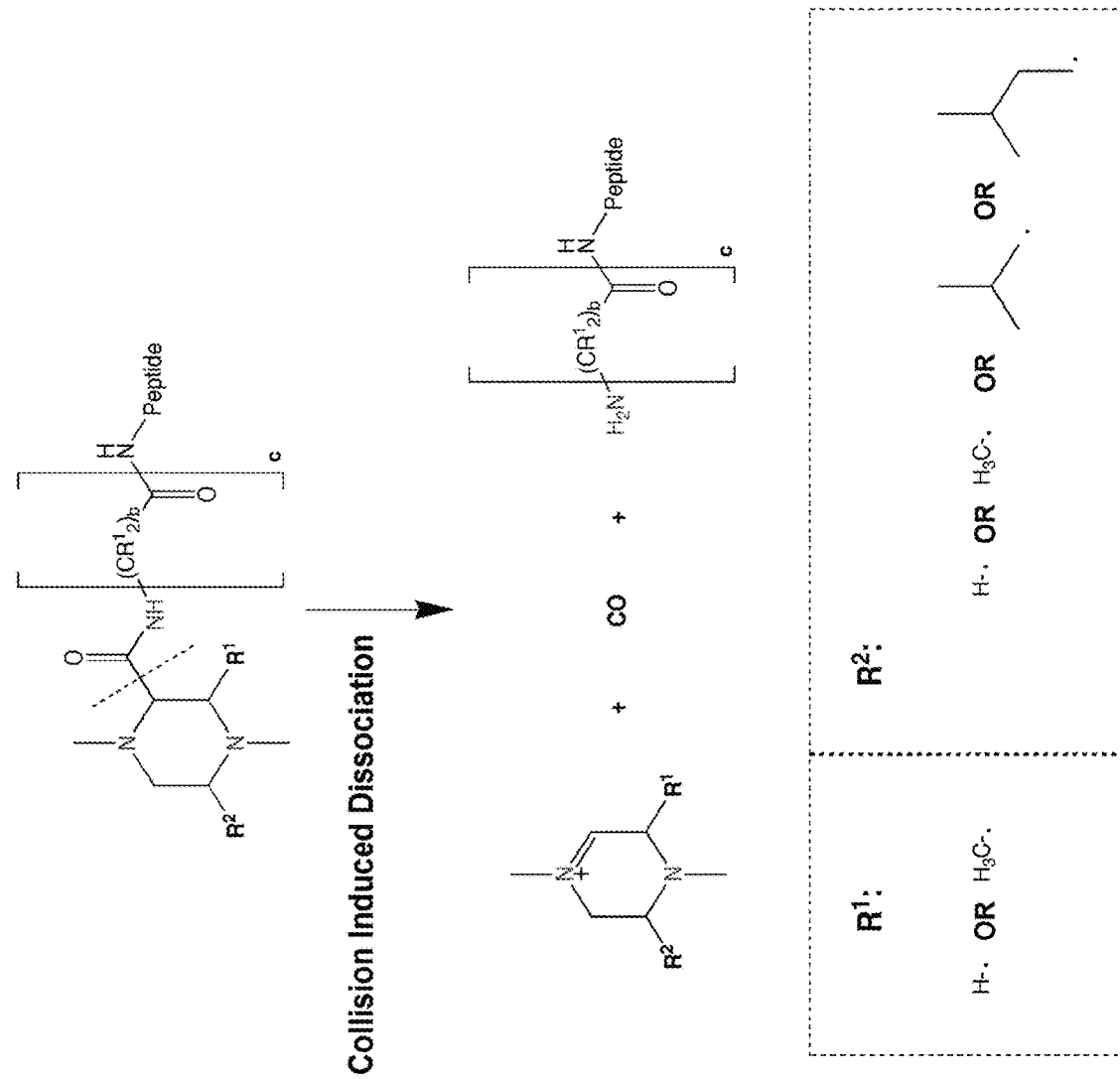
FIG. 1: Schematic of the predicted fragmentation pathway of the substituted piperazine-2-carboxylic acid mass label reporters according to this invention (depicted structure is hypothetical and illustrated only for the purpose of predicting the mass-to-charge ratio of expected reporter ions). Also shown is a first example of a suitable mass modifier linker according to this invention.

The present invention provides sets of isotopomeric reactive tags for the purposes of labelling peptides and other biomolecules with multiplexing rates greatly in excess of 10-plex. Co-selectable isotopologue arrays of isotomoperic reactive tags have masses differences in the range of millidalton which supports even higher levels of multiplexing.

The present invention also provides for methods of use of co-selectable isotopologue arrays of isotopomeric reactive tags that enable novel forms of analysis of labelled peptides, proteins and other biological molecules, particularly for the discovery of biologically significant differences between sets of biological samples.

In a first aspect, the present invention relates to a set of two or more mass labels, hereinafter referred to as "the first set of mass labels of the invention", wherein each mass label comprises the formula:

X-L-M-Re wherein:
X is a reporter moiety having an exact mass,
L is a bond cleavable by collision in a mass spectrometer,
M is a mass modifier, and
Re is a) a reactive functionality for attaching the mass label to an analyte or b) the analyte,
wherein each mass label in the set has an integer mass, wherein each mass label in the set has the same integer mass, wherein the set comprises two or more subsets of mass labels, each subset comprising one, two or more mass labels, wherein, when the subset comprises two or more mass labels, the exact mass of the reporter moiety X of each mass label in the subset is different from the exact mass of the reporter moiety X of the mass labels in the same subset and in all other subsets, wherein each mass label is distinguishable by mass spectrometry, wherein each mass label has a reporter moiety X comprising the following general formula:

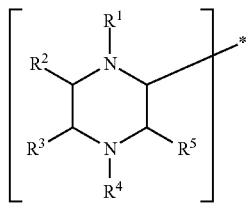

wherein each of $R^1$, $R^2$, $R^3$, $R^4$ and $R^5$ is independently H, a substituted or unsubstituted straight or branched $C_1$-$C_{10}$ alkyl group; or a structure selected from methyl, ethyl, propyl or n-propyl, isopropyl, butyl or n-butyl, isobutyl, sec-butyl, tert-butyl, pentyl or n-pentyl, neopentyl, tert-pentyl, iso-pentyl, sec-pentyl and 3-pentyl.

The term "exact mass" refers to the theoretical mass of the mass label or of the reporter moiety and is the sum of the exact masses of the individual isotopes of the entire mass label or reporter moiety, e.g. $^{12}C=12.000000$, $^{13}C=13.003355$ $H^1=1.007825$, $^{16}O=15.994915$. The "exact mass" takes account of mass defects.

The term "integer mass" is the sum of the integer masses of each isotope of each nucleus that comprises the molecule, e.g. $^{12}C=12$, $^{13}C=13$, $^1H=1$, $^{16}O=16$. The integer mass of an isotope is the sum of protons and neutrons that make up the nucleus of the isotope, i.e. $^{12}C$ comprises 6 protons and 6 neutrons while $^{13}C$ comprises 6 protons and 7 neutrons. This is often also referred to as the nominal mass, or atomic mass number or nucleon number of an isotope.

In the literature the term "isobaric" often refers to species that have the same integer mass and are co-selectable for MS/MS but in the context of this invention we will use the term "isobaric" refer to species that have the same exact mass and we will use the term "pseudo-isobaric" for species that have the same integer mass but may have slightly differing exact masses.

The difference in exact mass between at least two of the mass labels in a subset is usually less than 100 millidaltons, preferably less than 50 millidaltons, most preferably less than 20 millidaltons (mDa). Preferably, the difference in exact mass between at least two of the mass labels in a set is 2.5 mDa, 2.9 mDa, 6.3 mDa, 8.3 mDa, 9.3 mDa, or 10.2 mDa due to common isotope substitutions. For example, if a first label comprises a $^{13}C$ isotope, and in a second label this $^{13}C$ isotope is replaced by $^{12}C$ but a $^{14}N$ isotope is replaced by a $^{15}N$ isotope, the difference in exact mass between the two labels will be 6.3 mDa.

In the present specification, the term label is synonymous with the term tag.

The term "reporter moiety X" is used to refer to a moiety of the mass label to be detected independently, typically after cleavage, by mass spectrometry, however, it will be understood that the remainder of the mass label attached to the analyte as a complement ion may also be detected in methods of the invention. The mass modifier X is a moiety which is incorporated into the mass label to ensure that the mass label has a desired integer mass. The reporter moiety X of each mass label may in some embodiments comprise no heavy isotopes.

The components of the reporter moiety according to the invention are preferably fragmentation resistant so that the site of fragmentation of the reporter moiety can be controlled by the introduction of a cleavable bond L that is easily broken by Collision Induced Dissociation (CID), Surface Induced Dissociation, Electron Capture Dissociation (ECD), Electron Transfer Dissociation (ETD), or Fast Atom Bombardment. In the most preferred embodiment, the linkage is easily broken by CID.

It will be understood by the person skilled in the art that in order to achieve the desired integer masses, one or both of the moieties X and M, the reactive functionality Re or the analyte may be modified with heavy isotopes. Typically the heavy isotopes are selected from $^2H$, $^{13}C$, $^{15}N$ or $^{18}O$.

Preferably, the reporter moiety of each mass label in a subset is an isotopologue of the reporter moiety of all other mass labels in the subset. Isotopologues are chemical species that differ only in the isotopic composition of their molecules. For example, water has three hydrogen-related isotopologues: HOH, HOD and DOD, where D stands for deuterium ($^2H$). Isotopologues are distinguished from isotopomers (isotopic isomers) which are isotopic isomers having the same number of each isotope but in different positions. More preferably, the set of two or more mass labels comprises at least one subset comprising two or more mass labels.

Usually, the difference in exact mass is provided by a different number or type of heavy isotope substitution(s).

In one embodiment, the mass labels are isotopologues of Tandem Mass Tags as defined in WO01/68664.

In a preferred embodiment the aggregate molecular weight of the mass label is 600 Daltons or less, more preferably 500 Daltons or less, still more preferably 400 Daltons or less, most preferably from 300 to 500 Daltons.

In another preferred embodiment, the molecular weight of the reporter moiety is 400 Daltons or less, preferably 250 Daltons or less, more preferably 100 to 250 Daltons, most preferably 100-220 Daltons. A reporter moiety of small size is particularly advantageous because it produces a peak in the silent region of a mass spectrum, which allows the reporter moiety to be easily identified from the mass spectrum and also allows sensitive quantification.

The term silent region of a mass spectrum used in the present context is intended to refer to the region of a mass spectrum with low background "noise" caused by peaks relating to the presence of fragments generated by fragmentation of the labelled peptides. Thus, the term silent region is intended to refer to the region of the mass spectrum with low "noise" caused by peaks relating to the peptide to be detected. For a peptide or protein, the silent region of the mass spectrum is less than 220, preferably less than 200 Daltons.

The mass labels according to the invention are designed to be reacted with a biomolecule, such as a protein to form a labelled biomolecule, e.g. a labelled protein.

In one embodiment, $R^1$ and $R^4$ are methyl.

In another embodiment, $R^2$ is H.

In another embodiment, $R^3$ is selected from the group consisting of H, methyl, isopropyl, isobutyl.

In another embodiment, $R^5$ is H or methyl.

In a preferred embodiment, the reporter moiety X is selected from:

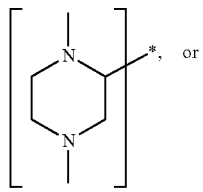

a)

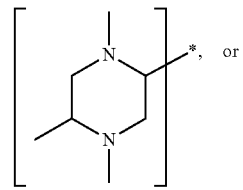

b)

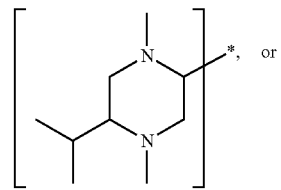

c)

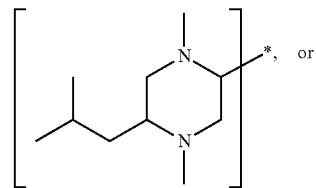

d)

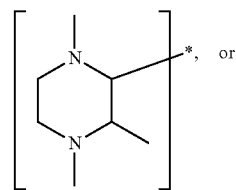

e)

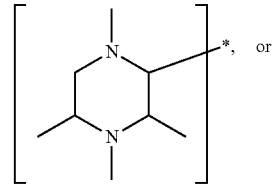

f)

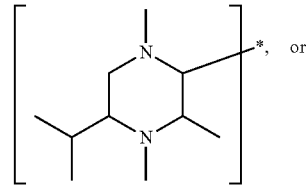

g)

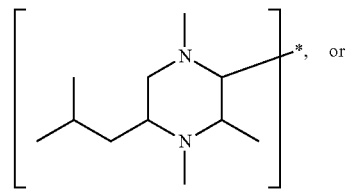

h)

In a more preferred embodiment, the reporter moiety X is selected from:

a)
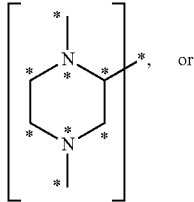

b)
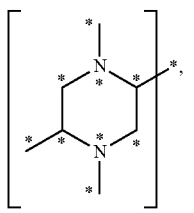

c)
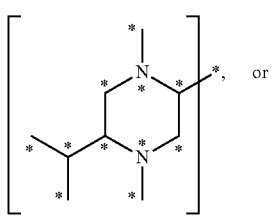

d)
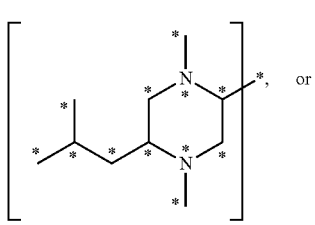

e)
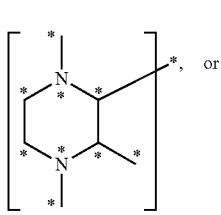

f)
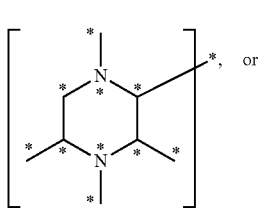

g)
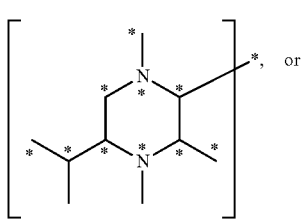

h)
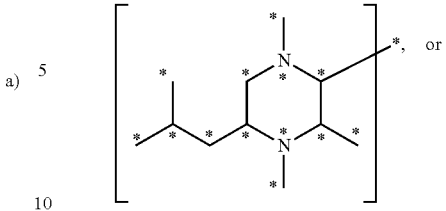

wherein * is an isotopic mass adjuster moiety and represents that carbon is $^{13}C$, nitrogen is $^{15}N$ or hydrogen is $^{2}H$, and wherein one or more * may be present.

In another embodiment, the cleavable bond L comprises, without limitation, an amide bond, a urea linkage, an ester linkage or an ether linkage. In a preferred embodiment, cleavable bond L comprises an amide bond. In another preferred embodiment, the cleavable bond L comprises a urea linkage. In another preferred embodiment, the cleavable bond L comprises an ester linkage. In another preferred embodiment, the cleavable bond L comprises an ether bond.

The term "mass modifier M", as used herein, refers to a moiety that ensures that each mass label in the set has a desired integer mass. The mass modifier M is not necessarily to be detected by mass spectrometry. However, the mass modifier M may be detected as part of a complement ion (see below). The mass modifier M is not particularly limited structurally, but merely serves to vary the overall mass of the mass label.

In another embodiment, the mass modifier M is selected from:

a)
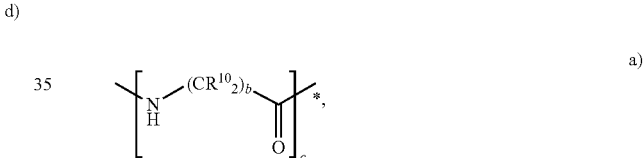

b)
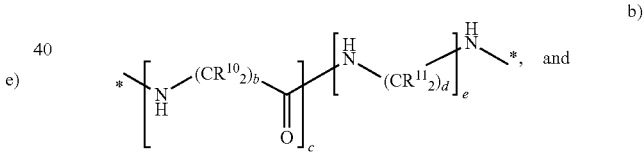

c)
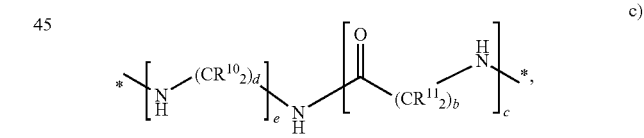

wherein:
each $R^{10}$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain, each $R^{11}$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain, b is an integer from 1-10,
c is an integer from 0-10,
d is an integer from 1-10, and
e is an integer from 1-10.

In a preferred embodiment, the mass modifier M is selected from:

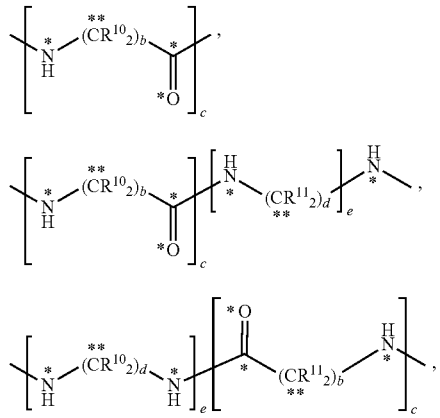

wherein * is an isotopic mass adjuster moiety and represents that oxygen is $^{18}O$, carbon is $^{13}C$, nitrogen is $^{15}N$ or hydrogen is $^{2}H$, and wherein one or more * may be present.

In another embodiment, each mass label additionally comprises at least one mass series modifying group, wherein the mass series modifying group is part of the reporter moiety X and/or part of the mass modifier M.

Preferably, each mass label comprises a mass series modifying group, wherein the at least one mass series modifying group is part of the reporter moiety X or of the mass modifier M or both. More preferably, the mass series modifying group is part of the reporter moiety X.

Preferably, the mass series modifying group may be selected from:
- a) a heavy isotope $^{2}H$, $^{13}C$, $^{15}N$ or $^{18}O$;
- b) a substituted or unsubstituted straight or branched $C_1$-$C_{10}$ alkyl group optionally comprising one or more heavy isotope substitutions;
- c) or a combination of a) and b).

In one embodiment, the mass series modifying group is selected from —$CH_3$, —$^{13}CH_3$, —$CHD_2$, —$^{13}CHD_2$, —$^{13}CD_3$ or —$CD_3$.

In another preferred embodiment, each mass label comprises at least one mass series modifying group having the following structure:

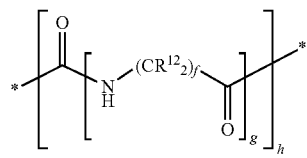

wherein:
- each $R^{12}$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain;
- f is an integer from 1 to 10;
- g is an integer from 1 to 10; and
- h is an integer from 1 to 10.

In the mass labels according to the invention, Re may either be a reactive functionality for attaching the mass label to an analyte or be an analyte.

Preferably the mass tags additionally comprise a reactive functionality to allow the mass label to be conjugated to an analyte. The reactive functionality for attaching the mass label to the analyte is not especially limited and may comprise any appropriate reactive group.

The reactive functionality may react with an amino group on the biological molecule, for example the ε-amino group of a lysine residue. In the simplest embodiments this may be an N-hydroxysuccinimide ester. Other reactive functionalities are contemplated herein such as those which react with thiol groups in biological molecules. In particular these reactive functionalities are designed to react with the thiol group of a cysteine residue. Examples of reactive groups of the present invention which are able to react with cysteine residues are the maleimido, haloacetyl and 2-dithiopyridine groups. The thiol group of cysteine undergoes nucleophilic addition across the double bond of the maleimido group and undergoes nucleophilic substitution with the haloacetyl or 2-dithiopyridine group.

Reactive functionalities which are capable of reacting with carbonyl or hydroxyl groups in biological molecules are also contemplated herein. In particular, these reactive functionalities are designed to react with the carbonyl or hydroxyl groups of steroid hormones. Reactive groups of the present invention which are able to react with carbonyl or hydroxyl groups in a biological molecule are hydrazide or —CONH—$(CH_2)_n$—$ONH_2$, wherein n is from 1 to 6, and preferably n is 3 i.e. aminoxypropyl amide. These groups react with carbonyl groups to form hydrazones or O-alkyloximes respectively. Examples of reactive functionalities are shown in WO2011/036059, which reference is incorporated herein.

Preferably, the reactive functionality is an N-hydroxysuccinimide ester, a 2,3,5,6-tetrafluorophenyl ester or a sulphodichlorophenyl ester.

When Re is the analyte, the analyte preferably comprises amino acids, peptides, polypeptides, nucleotides, oligonucleotides, polynucleotides, carbohydrates, lipids, phospholipids or combination thereof.

Improving multiplexing is a highly sought characteristic of isobaric mass labels as it allows labelling of a high number of sample and analysis is one single experiments thus reducing time of analysis, costs and also standardizing the analysis conditions for a higher number of samples. In order to generate mass labels for isobaric mass labelling using only $^{15}N$ and $^{13}C$ substitutions in a mass label according to the general structures disclosed in the present invention, it is necessary to consider the positions substitutable with heavy isotope mass series modifying groups comprising 2 different elements (P positions) and positions substitutable for the first element (A positions) and positions substitutable for the second element (B positions) different from the first. The number of A positions should be greater than or equal to the number of B positions. Assuming there are (P+1) subsets of mass labels and the $x^{th}$ subset of mass labels comprises C mass labels, C should be less than or equal to (B+1). Each reporter moiety comprises (x−1) positions substituted with heavy isotopes from either the first or second element and where the $w^{th}$ mass label in each subset of mass labels comprises y atoms of the first heavy isotope element and z atoms of the second heavy isotope element different from the first, x will have values from 1 to (P+1). P=(A+B) and the total number of mass labels will be (A+1) multiplied by (B+1).

In preferred embodiments B is greater than or equal to 2.

For example, a mass label where there are 7 dopable carbons and 2 dopable Nitrogens in the reporter moiety and in the mass modifier, will support up to 24-plex isobaric sets, i.e. (7+1) multiplied by (2+1). At single Dalton resolution, these reporters will support 10-plex (P=7+2 giving (9+1) subsets of mass labels with different integer reporter masses. Obviously as the reporter moiety groups can be substituted with different R-groups different isomers of the mass labels are possible, providing options for different fragmentation behaviours.

The most preferred mass labels according to the invention together with examples of sets of two or more mass labels comprising heavy isotopes mass series modifying groups are described in details herein below in preferred Embodiments 1 to 6. The mass labels are identified by the set number, parent set size and the reporter ion mass, e.g. in Embodiment or set 1 or below, each mass label is named TMT-1-21-"reporter mass", where TMT stands for Tandem Mass Tag, i.e. tags for tandem mass spectrometry, the digit 1 refers to the Set number, the 21 refers to the number of mass labels in the set and the reporter mass is the mass-to-charge ratio of the expected reporter ion under Collision Induced Dissociation conditions. Different reporter ions may be obtained by Electron Transfer Dissociation (ETD) or Electron Capture Dissociation (ECD).

Embodiment 1

The mass label has structure:

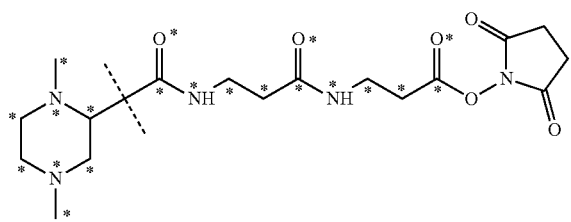

wherein * represents that oxygen is $^{18}O$, carbon is $^{13}C$, nitrogen is $^{15}N$ or hydrogen is $^{2}H$, and wherein one or more * may be present.

Figure 3:
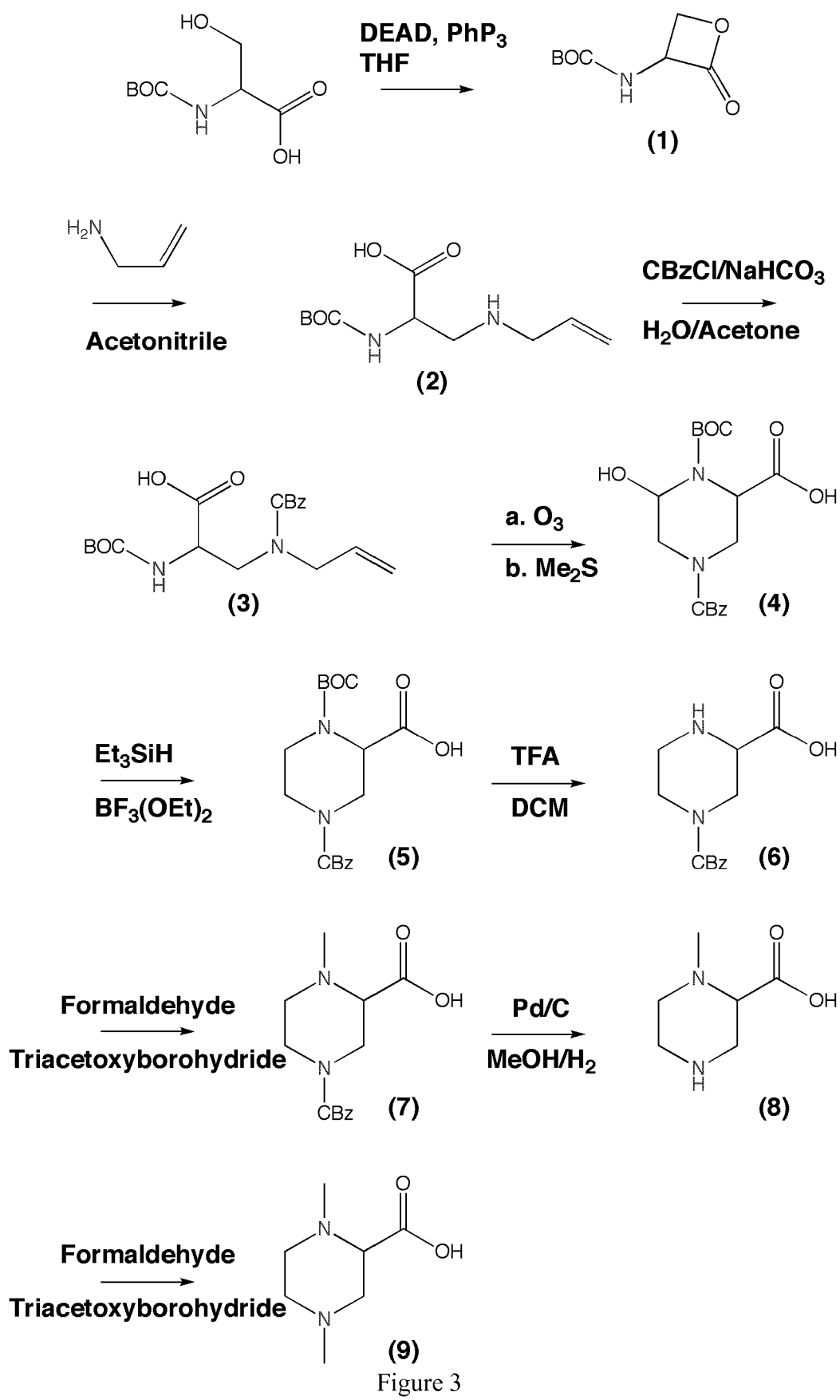
FIG. 3: Schematic representation of a published synthesis method for the N',N'-dimethyl piperazine-2-carboxylic acid reporter moiety according to this invention.
Figure 7:
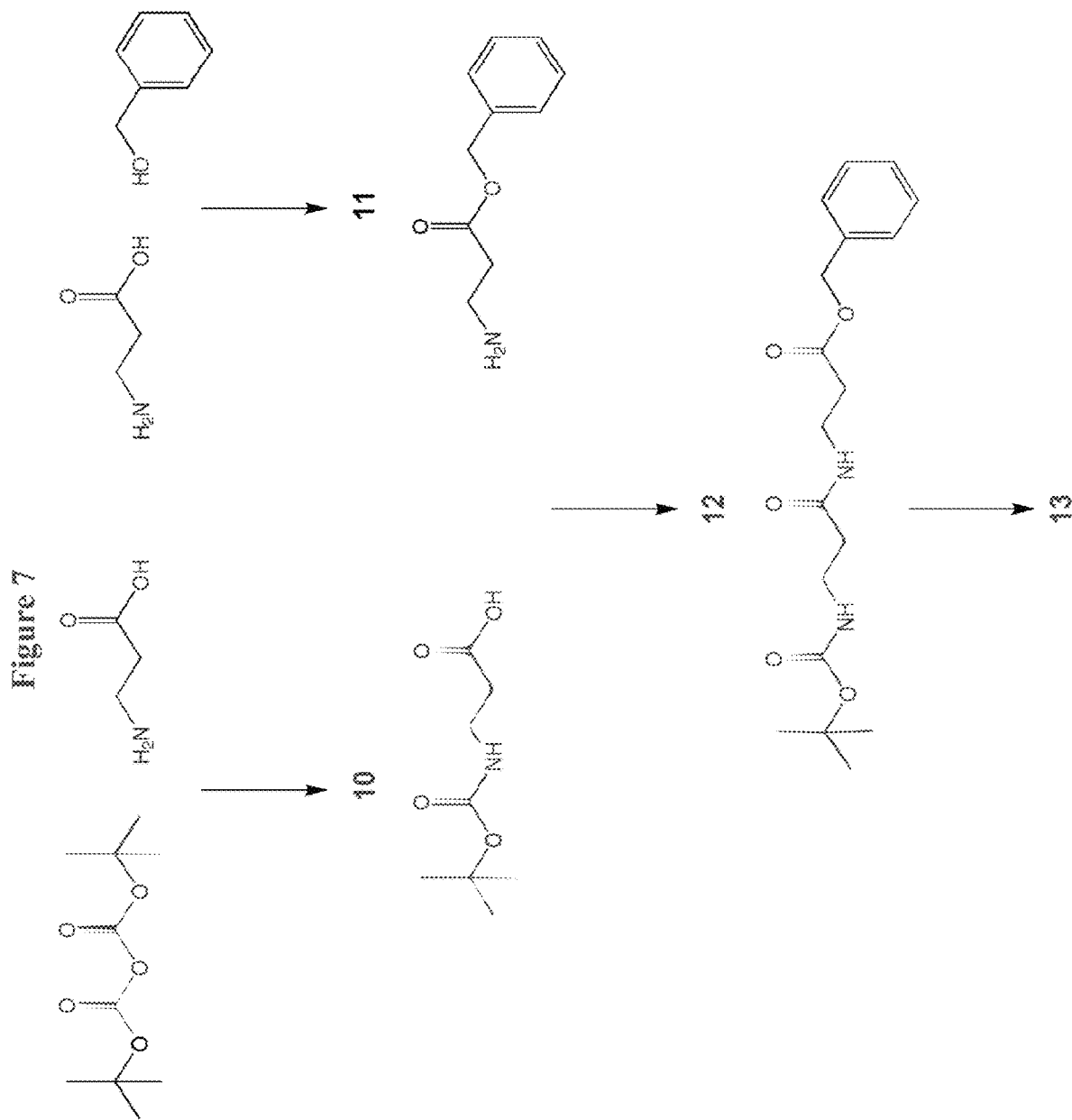
FIG. 7: Schematic illustration of the synthesis and coupling of mass modifier linker composed of two consecutive beta-alanine residues to the reporter structures of this invention.

The expected fragmentation of the tags in example set 1 is shown in FIG. 1. The synthesis of the reporter structure is shown in FIG. 3 and the addition of the double beta-alanine linkers is shown in FIG. 7. The synthesis of the tags of this invention is discussed in more detail later in this document.

In a specific preferred embodiment of an isobaric set of mass tags according to this invention, the mass adjuster moiety * is $^{13}C$ or $^{15}N$ and the set comprises n=21 mass labels having the following structures:

(Subset 1)

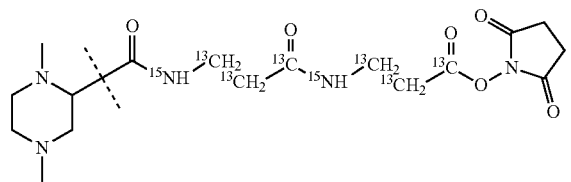

TMT-1-21-113.10732

(Subset 2)

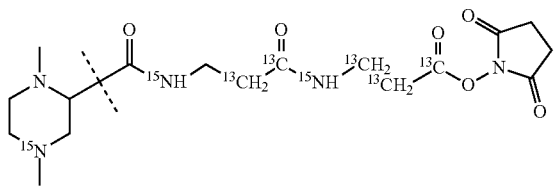

TMT-1-21-114.10436

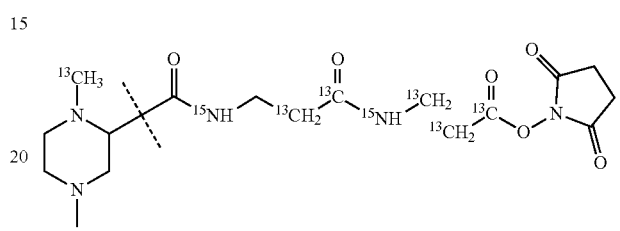

TMT-1-21-114.11068 (Subset 2)

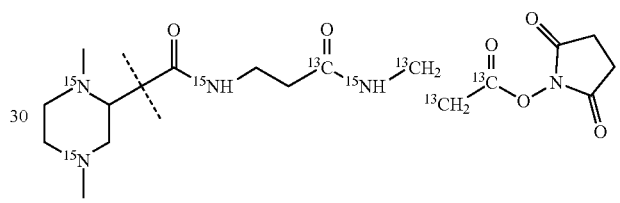

TMT-1-21-115.10139 (Subset 3)

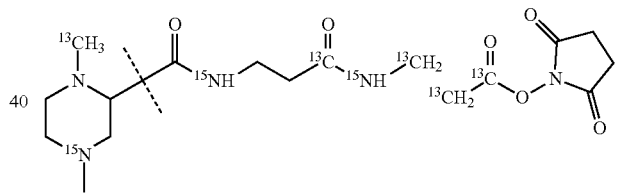

TMT-1-21-115.10771 (Subset 3)

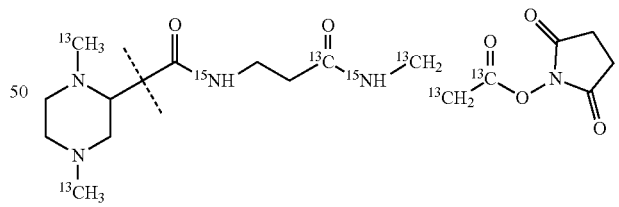

TMT-1-21-115.11403 (Subset 3)

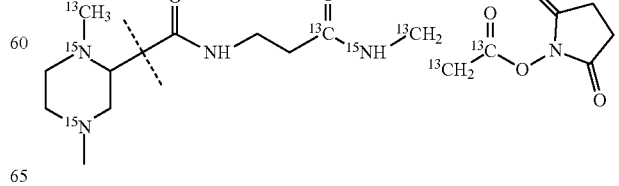

TMT-1-21-116.10475 (Subset 4)

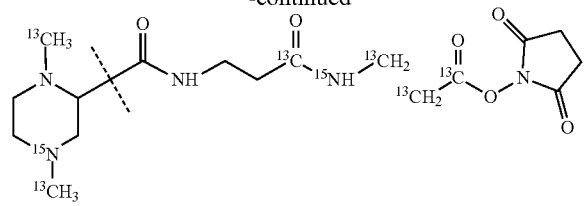
TMT-1-21-116.11107 (Subset 4)
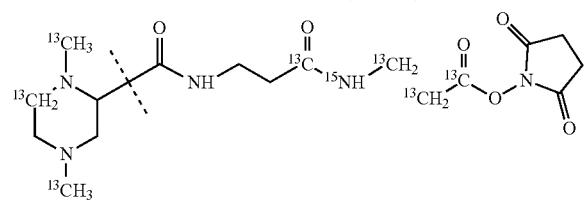
TMT-1-21-116.11739 (Subset 4)
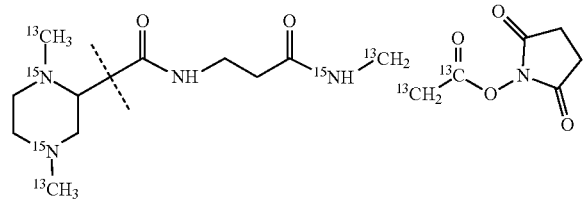
TMT-1-21-117.1081 (Subset 5)
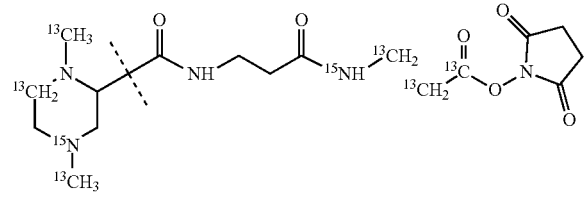
TMT-1-21-117.11442 (Subset 5)
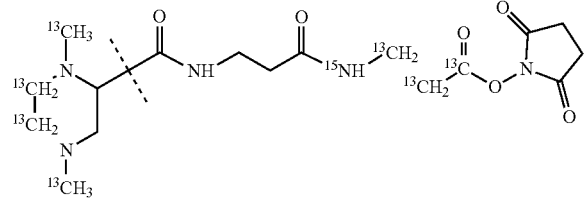
TMT-1-21-117.12074 (Subset 5)
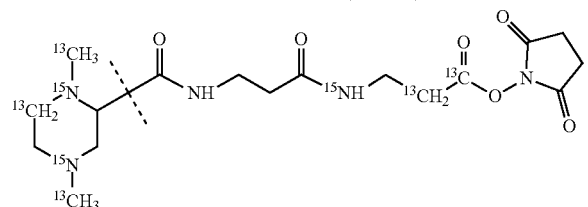
TMT-1-21-118.11146 (Subset 6)
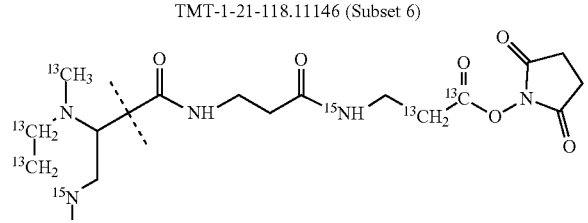
TMT-1-21-118.11778 (Subset 6)
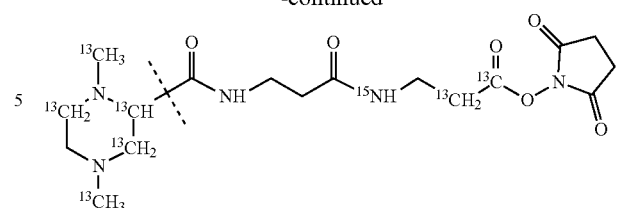
TMT-1-21-118.1241 (Subset 6)
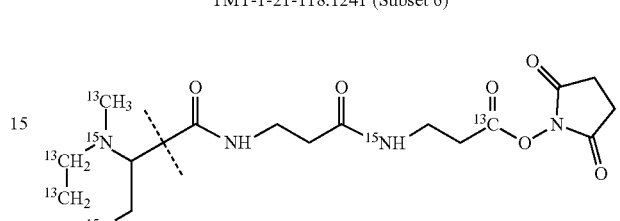
TMT-1-21-119.11481 (Subset 7)
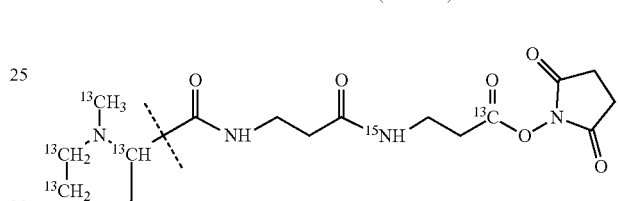
TMT-1-21-119.12113 (Subset 7)
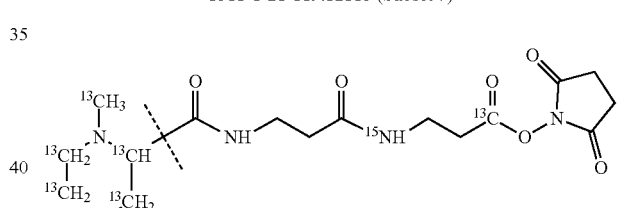
TMT-1-21-119.12745 (Subset 7)
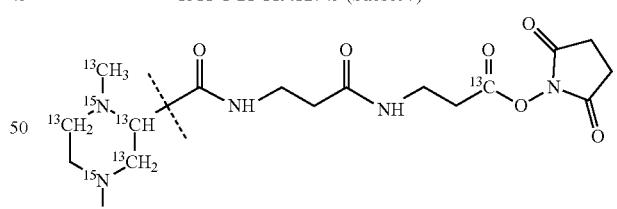
TMT-1-21-120.11817 (Subset 8)
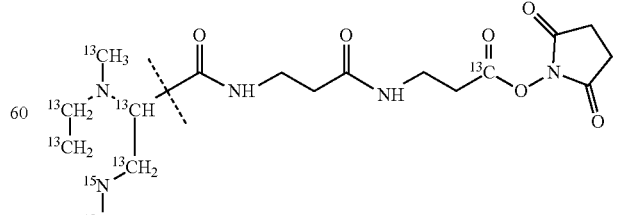
TMT-1-21-120.12449 (Subset 8)

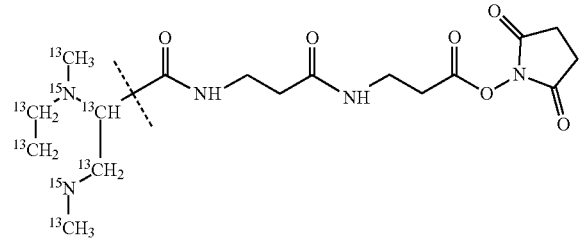

TMT-1-21-121.12152 (Subset 9)

Taking the terminology set out in the preferred embodiment described above, m (as defined above) is 21 and n=8. Since there are more carbon atoms into which $^{13}C$ can be substituted than nitrogen atoms into which $^{15}N$ can be substituted, there are a=6 substitutable carbon nuclei and b=2 substitutable nitrogen nuclei. Thus there are 6 atoms of the first heavy isotope mass adjuster, which is $^{13}C$, incorporated into each tag and 2 atoms of the second heavy isotope mass adjuster, which is $^{15}N$ and the full set of mass tags is created by making all the possible combinations of mass adjusters on either side of the fragmentable bond, which is marked with the dashed line in the structures above. It can be seen in the list above that there are (n+1)=9 subsets of tags based on the integer mass of the reporter ions, i.e. the reporter ions in subset 2 are approximately 1 dalton heavier than the reporter ions in subset 1. Similarly, the reporter ions in subset 3 are approximately 1 dalton heavier than the reporter ions in subset 2, etc. Within each subset of tags, it can be seen from the calculated exact masses that each tag differs from the next by 6.32 millidaltons. In subset 1, there are no heavy isotope mass adjusters in the reporter ion and there is only one way in which this reporter can be constructed so there is only 1 tag in subset 1. In subset 2, there is one heavy isotope mass adjuster in the reporter ion, shifting the mass of the reporter by approximately 1 dalton relative to subset 1. There are 2 ways to introduce the mass adjuster, by introduction of a single $^{15}N$ nucleus or by introduction of a single $^{13}C$ nucleus and hence there are two tags in subset 2 differing in mass from each other by 6.3 millidaltons. In subset 3, there are two heavy isotope mass adjusters in the reporter ion, shifting the mass of the reporter by approximately 1 dalton relative to subset 2. There are 3 ways to introduce the 2 mass adjusters into subset 3, by introduction of two $^{15}N$ nuclei or by introduction of a single $^{15}N$ nucleus and a single $^{13}C$ nucleus or by introduction of two $^{13}C$ nuclei and hence there are 3 tags in subset 3. In subset 4, there are three heavy isotope mass adjusters in the reporter ion, shifting the mass of the reporter by approximately 1 dalton relative to subset 3. There are again only 3 ways to introduce the 3 mass adjusters into subset 3, by introduction of two $^{15}N$ nuclei and a single $^{13}C$ or by introduction of a single $^{15}N$ nucleus and a two $^{13}C$ nuclei or by introduction of three $^{13}C$ nuclei and hence there are 3 tags in subset 4. In general, the number of tags in each subset is limited by which of the mass adjuster nuclei is present less frequently in the structure. In example set 1, there are only two nitrogen nuclei in the reporter and in the mass normalizer and so b=2 as defined above and the number of tags in each subset of tags is lower than or equal to (b+1), which is a maximum of 3 tags per subset. In the $8^{th}$ subset, there are 7 heavy isotope mass modifiers and there are only two ways to construct a reporter ion with the 8 heavy isotopes while retaining an overall isobaric tag structure so there are only two tags in the $9^{th}$ subset and similarly in the $9^{th}$ subset, all 8 heavy isotope mass adjusters are present in the reporter and there is only one way to construct a reporter with all of the mass modifiers, so there is only 1 tag in subset 9.

It should be clear to one of ordinary skill in the art that the mass normalizer group, which comprises two beta-alanine residues in this tag, could be varied considerably. Obvious substitutions include, replacement with other amino acids such as alanine, valine, leucine or with longer amino acids such as gamma-aminobutyric acid, aminopentanoic acid or aminohexaminoic acid. Poly-ethylene glycol linkers might also be appropriate with an amino and a carboxylic acid terminus. The preparation of benzyl esters and use of these esters for all these alternatives would be essentially the same as shown in FIG. 7 for beta-alanine.

The limitation on the multiplexing rate for a single isobaric mass tag set, such as Embodiment Set 1 described above can be overcome by providing multiple sets each carrying a unique additional mass. The additional mass is provided by a mass series modifying group according to the second aspect of this invention. The concept of introducing a mass series modifier into the mass normalising linker is described in U.S. Pat. No. 7,294,456, which is incorporated herein and also in WO2011036059, which is incorporated herein. In WO2011036059, the inventors found that it was possible to develop arrays of isobaric mass tag sets by adding additional beta-alanine moieties into the linker region of the commercially available 6-plex Tandem Mass Tag Dimethylpiperazine-Beta-Alanine tag structure. Such a unitary approach provides a rapid and inexpensive means of increasing the multiplexing rate from 6 to 12, 18, 24 or more samples. The isobaric mass tag sets of this invention may also be modified by introduction of additional linkers into the mass normaliser, as previously disclosed.

For example, Embodiment Set 1 can be modified by introduction of a further undoped GABA linker to every tag in Embodiment set 1 as shown below to give a different set of 21 tags that is differentiated from the tags in Embodiment Set 1 by the mass of a GABA linker.

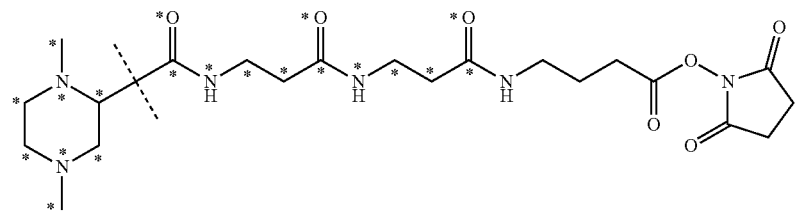

Clearly, a further set of 21 tags can be created by adding an undoped beta-alanine linker to every tag in Embodiment Set 1 as shown below:

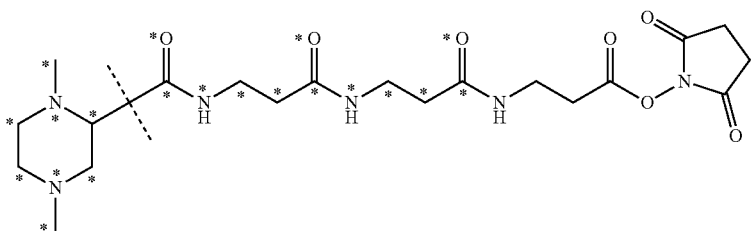

Moreover, a further set of 24 tags can be created by adding a doped beta-alanine linker to every tag in Embodiment Set 1, where the additional beta-alanine linker comprises a fixed substitution of three $^{13}$C nuclei and a $^{15}$N nucleus as shown below:

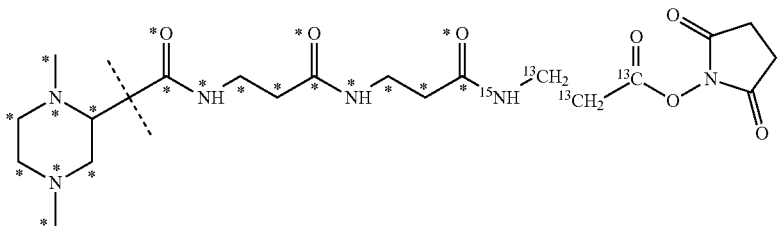

The skilled person will understand that the specific means of introducing additional masses to the mass normalising linker of the tag structures disclosed in this patent is not particularly limiting and alternate means are considered to be within the scope of the present invention.

This invention discloses a further method of introducing a mass series modifier into the tags of this invention. It has been found by the present inventors that mass series modification of the reporter group is highly advantageous as will be discussed in Embodiment Sets 2 to 4 below:

Embodiment 2

The mass label has structure:

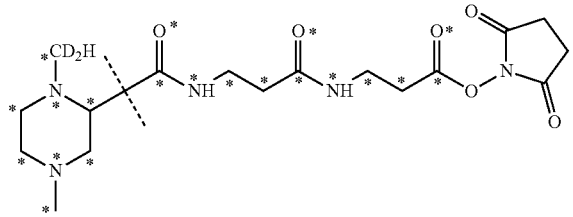

wherein * represents that oxygen is $^{18}$O, carbon is $^{13}$C, nitrogen is $^{15}$N or hydrogen is $^{2}$H, and wherein one or more * may be present.

In the structure above, the 1' N-methyl groups substituted into the piperazine ring has a fixed reporter mass series modifier substitution of two deuterium atoms. This fixed substitution in this example means that the reporter ions of Example Set 2 have a minimum mass offset relative to the reporter ions of Embodiment Set 1, thus the heaviest reporter in Embodiment Set 2 will be approximately 5.9 millidaltons heavier than the heaviest reporter in Embodiment Set 1. The deuterium substitutions in Embodiment Set 3 also mean that all the reporters in Embodiment Set 2 will have a different mass from every reporter in Embodiment Set 1.

The synthesis of the reporter structure is shown in FIG. 3 and the addition of the double beta-alanine linkers is shown in FIG. 7. The synthesis of the tags of this invention is discussed in more detail in the Examples of the present document.

An example of a set of n=7 mass labels comprising the mass series modifying groups $^{2}$H (i.e. D) $^{13}$C or $^{15}$N is shown below:

(Subset 3)

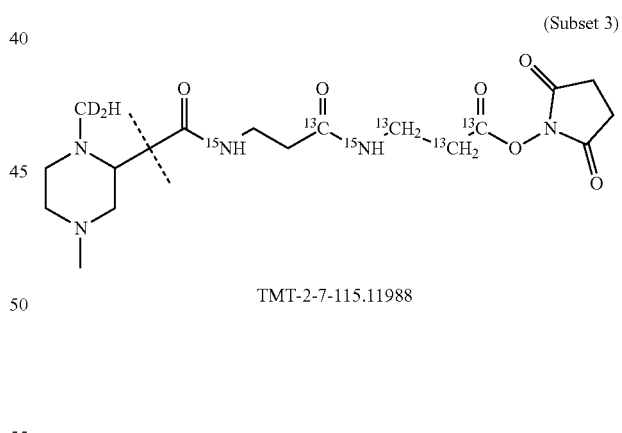

TMT-2-7-115.11988

(Subset 4)

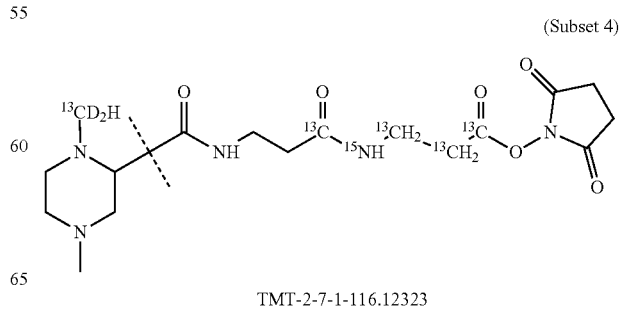

TMT-2-7-1-116.12323

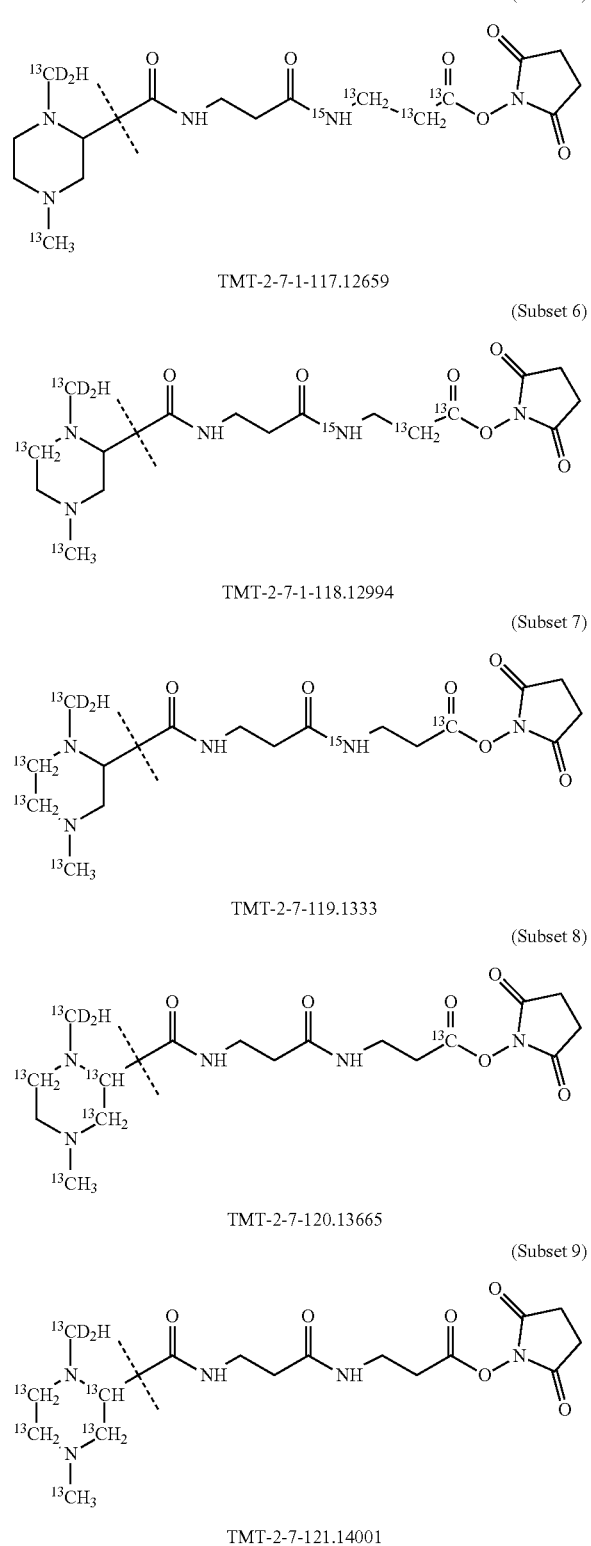

TMT-2-7-1-117.12659 (Subset 5)

TMT-2-7-1-118.12994 (Subset 6)

TMT-2-7-119.1333 (Subset 7)

TMT-2-7-120.13665 (Subset 8)

TMT-2-7-121.14001 (Subset 9)

As will be apparent to the person skilled in the art, the tags in Embodiment Set 2 are all isotopes of the tags in Embodiment Set 1 with tags in Embodiment set 2 (Parent Tag Mass of Tag 1 in Embodiment Set 2 is: 405.21618 Daltons) being approximately isobaric with tags in Embodiment Set 1 (Parent Tag Mass of Tag 1 in Embodiment Set 1 is: 405.21033 Daltons). This means that peptides labelled with tags from Embodiment Set 2 would be co-selectable with peptides labelled with tags from Embodiment Set 1 when these peptides are selected for sequencing in a mass spectrometer. More importantly, the reporter moieties X in Embodiment Set 1 are all different from the reporter moieties X in Embodiment Set 2. This means that Embodiment Set 1 can be used together with Embodiment Set 2 to label up to 28 samples for multiplexing. Peptides labelled with tags from Embodiment Set 2 will mostly co-elute with peptides labelled with tags from Embodiment Set 1, although with the possibility of a small mobility shift due to the presence of deuterium in the tags of Embodiment Set 2. Because the tags are isotopes of each other and will mostly co-elute, and the tags are co-selectable, then peptides labelled with Embodiment Set 2 will be analyzed simultaneously with peptides of Embodiment Set 1 and the tags will behave as if they are single pseudo-isobaric sets of tags. These two sets of tags comprise mass series modified reporter ions which all give different reporter ions so when peptides labelled with tags from Embodiment Sets 1 and 2, reporter ions can still be assigned to their correct peptides because the reporters are all different. Note, that the minimum differences in masses between reporters in Set 1 and reporters in Set 2 is almost 5.9 millidaltons, but Orbitrap instruments and Fourier Transform Ion Cyclotron Resonance instruments can already provide adequate mass resolution to allow robust discrimination of reporter ions of all the tags shown in Embodiment Sets 1 and 2.

The person skilled in the art will immediately appreciate that although the fixed substitutions of $^2H$, $^{13}C$ and $^{15}N$ are shown in a particular location in the examples shown above, this has been done as a convenience for the purposes of explanation and these fixed substitutions in Embodiment Set 2 could located at any suitable location within the reporter ion if it is more convenient or cost-effective to locate them elsewhere.

Embodiment 3

The mass label has structure:

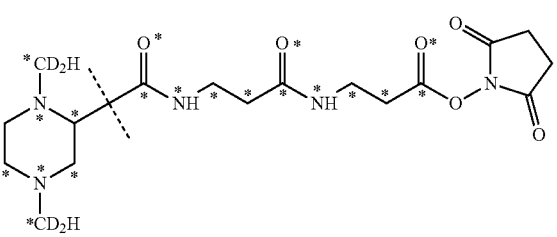

wherein * represents that oxygen is $^{18}O$, carbon is $^{13}C$, nitrogen is $^{15}N$ or hydrogen is $^2H$, and wherein one or more * may be present.

In the structure above, the N-methyl groups substituted into the piperazine ring both have a fixed reporter mass series modifier substitution of 2 deuterium atoms. These fixed substitutions in this embodiment mean that the reporter ions of Embodiment Set 3 have a minimum mass offset relative to the reporter ions of Embodiment Set 2, thus the heaviest reporter in Embodiment Set 3 will be approximately 5.9 millidaltons heavier than the heaviest reporter in Embodiment Set 2. The deuterium substitutions in Embodiment Set 3 also mean that all the reporters in Embodiment Set 3 will have a different mass from every reporter in Embodiment Set 2.

The synthesis of the reporter structure is shown in FIG. 3 and the addition of the double beta-alanine linkers is shown in FIG. 7. The synthesis of the tags of this invention is discussed in more detail in the experimental section of the present document.

An example of a set of n=5 mass labels comprising the mass series modifying groups $^{13}$C or $^{15}$N is shown below:

(Subset 5)

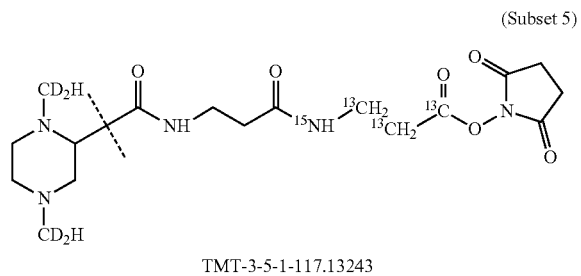

TMT-3-5-1-117.13243

(Subset 6)

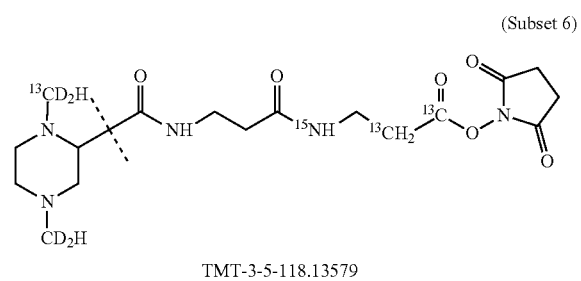

TMT-3-5-118.13579

(Subset 7)

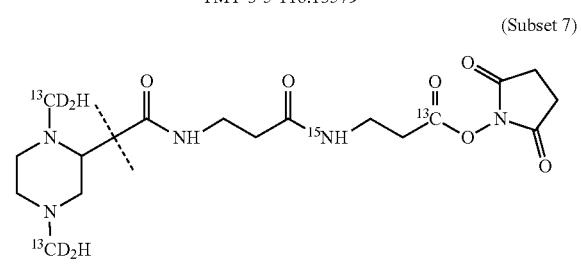

TMT-3-5-119.13914

(Subset 8)

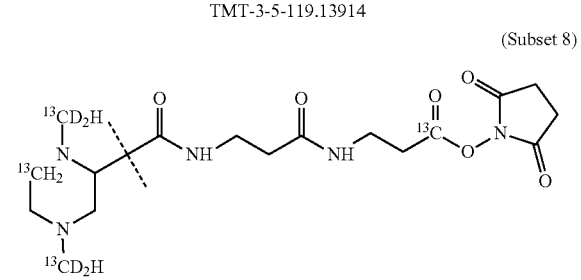

TMT-3-5-120.13618

(Subset 9)

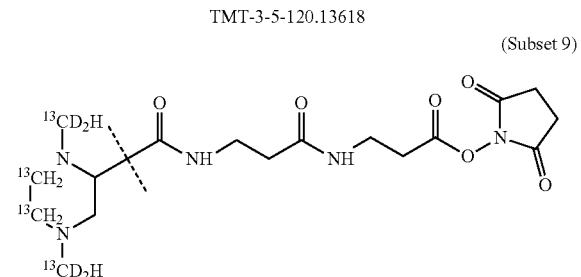

TMT-3-5-121.14585

As with Embodiment Set 2, the tags of Embodiment Set 3 are also all isotopes of the tags in Embodiment Set 1 with tags in Embodiment set 2 (Parent Tag Mass of Tag 1 in Embodiment Set 3 is: 405.22834 daltons) being approximately isobaric with tags in Embodiment Set 1 (Parent Tag Mass of Tag 1 in Embodiment Set 1 is: 405.21033 daltons). This means that Embodiment Set 1 can be used together with Embodiment Sets 2 and 3 to label up to 33 samples for multiplexing. Again, the minimum differences in masses between reporters in Set 2 and reporters in Set 3 is almost 5.9 millidaltons, but Orbitrap instruments and Fourier Transform Ion Cyclotron Resonance instruments can already provide adequate mass resolution to allow robust discrimination of reporter ions of all the tags shown in Embodiment Sets 1, 2 and 3.

Embodiment 4

The mass label has the structure:

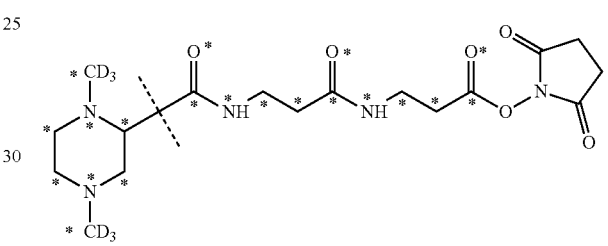

wherein * represents that oxygen is $^{18}$O, carbon is $^{13}$C, nitrogen is $^{15}$N or hydrogen is $^{2}$H, and wherein one or more * may be present.

Note in the structure above, the N-methyl groups substituted into the piperazine ring both have a fixed reporter mass series modifier of 3 deuterium atoms. These fixed substitutions in this Embodiment mean that the reporter ions of Embodiment Set 4 have a minimum mass offset relative to the reporter ions of Embodiment Set 3, thus the heaviest reporter in Embodiment Set 4 will be approximately 5.9 millidaltons heavier than the heaviest reporter in Embodiment Set 3. The deuterium substitutions in Embodiment Set 4 also mean that all the reporters in Embodiment Set 4 will have a different mass from every reporter in Embodiment Set 4.

An example of a set of n=3 mass labels comprising the mass series modifying groups $^{13}$C or $^{15}$N is shown below:

(Subset 7)

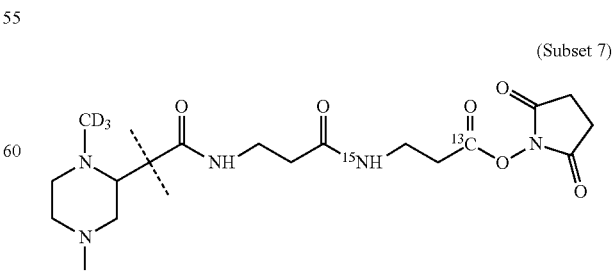

TMT-4-3-119.14499

(Subset 8)

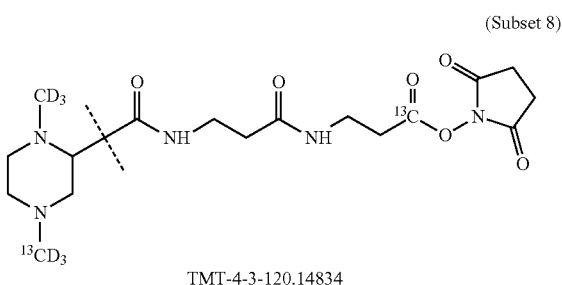

TMT-4-3-120.14834

(Subset 9)

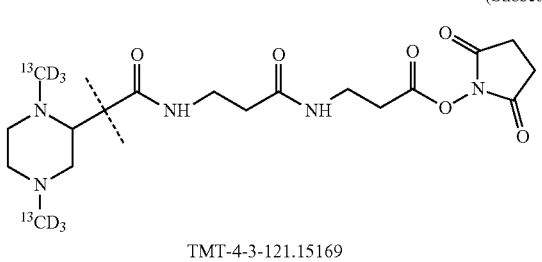

TMT-4-3-121.15169

Alternative heavy isotope substitutions could also be introduced with additional fixed substitutions of hydrogen, deuterium, $^{12}C$ or $^{14}N$ as illustrated below:

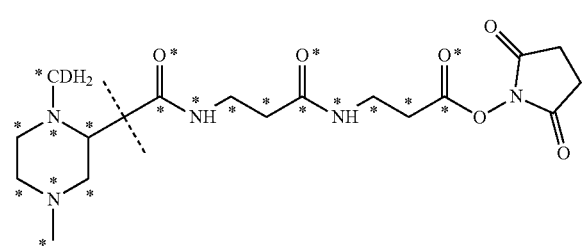

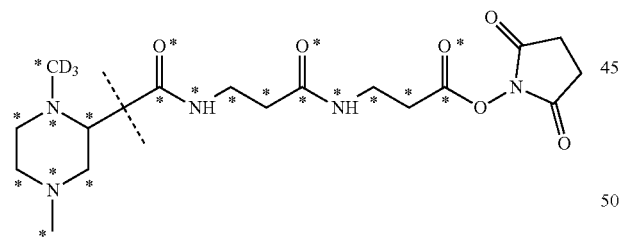

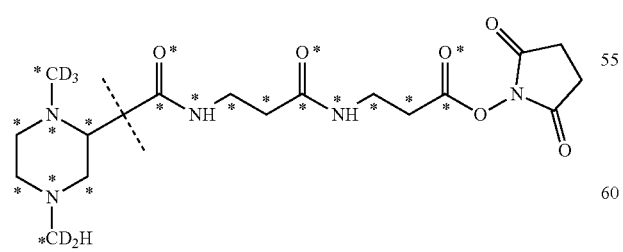

wherein * represents that oxygen is $^{18}O$, carbon is $^{13}C$, nitrogen is $^{15}N$ or hydrogen is $^{2}H$, and one or more * may be present.

Embodiment 5

The mass label has structure:

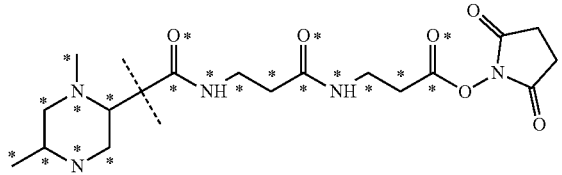

wherein * represents that oxygen is $^{18}O$ carbon is $^{13}C$, nitrogen is $^{15}N$ or hydrogen is $^{2}H$, and wherein one or more * may be present.

Figure 4:
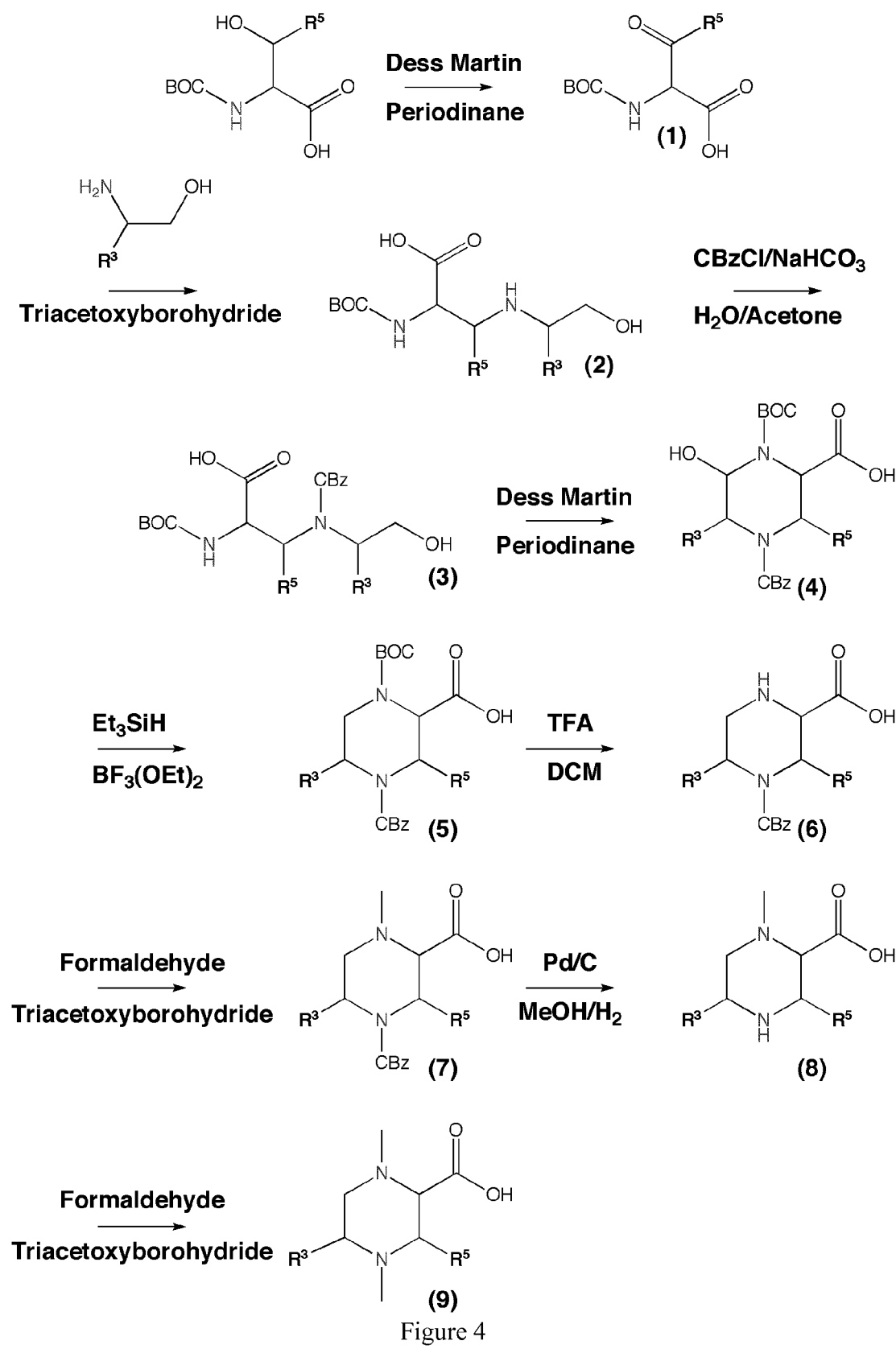
FIG. 4: Schematic representation of a second novel synthesis method for the production of ring-substituted N',N'-dimethyl piperazine-2-carboxylic acid reporter moieties of this invention.

The synthesis of the reporter structure is shown in FIG. 4 using threonine and the addition of the double beta-alanine linkers is shown in FIG. 7. The synthesis of the tags of this invention is discussed in more detail later in this document.

An example of a set of n=24 mass labels comprising the mass series modifying groups $^{13}C$ or $^{15}N$ is shown below:

(Subset 1)

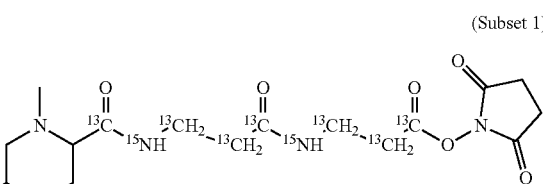

TMT-5-24-127.12297

(Subset 2)

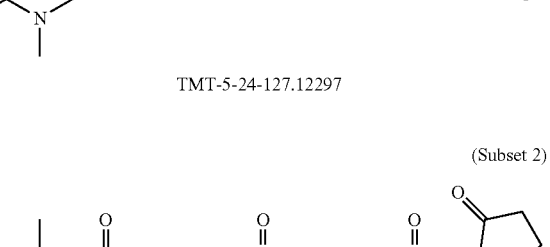

TMT-5-24-128.12001

(Subset 2)

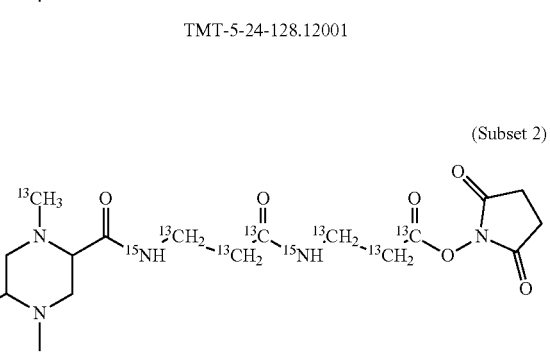

TMT-5-24-128.12633

-continued
(Subset 3)
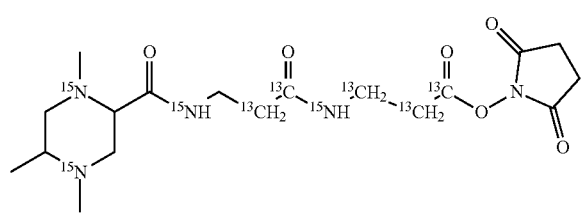
TMT-5-24-129.11704
(Subset 3)
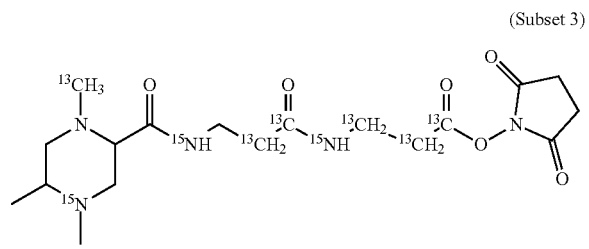
TMT-5-24-129.12336
(Subset 3)
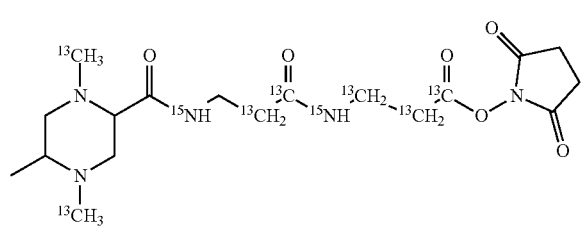
TMT-5-24-129.12968
(Subset 4)
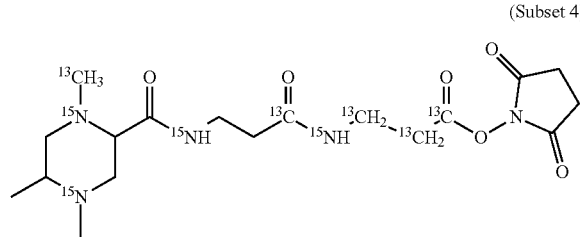
TMT-5-24-130.1204
(Subset 4)
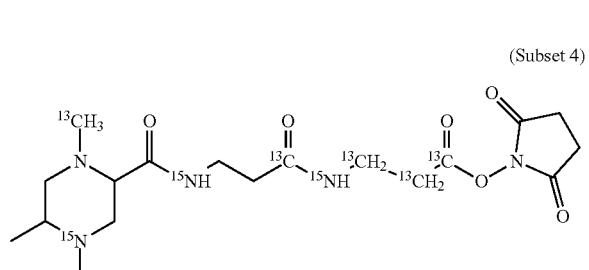
TMT-5-24-130.12672
-continued
(Subset 4)
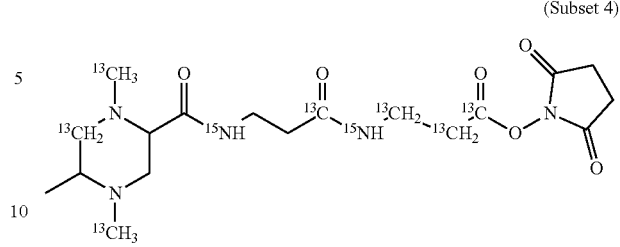
TMT-5-24-130.13304
(Subset 5)
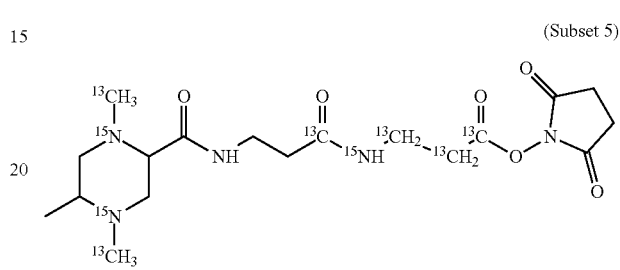
TMT-5-24-131.12375
(Subset 5)
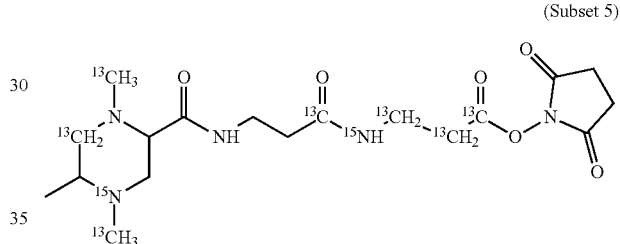
TMT-5-24-131.13007
(Subset 5)
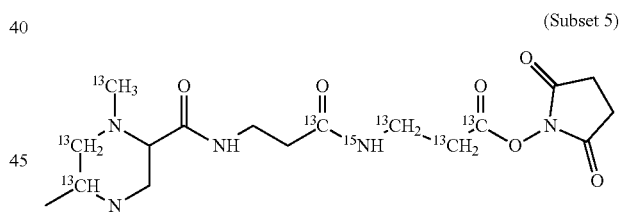
TMT-5-24-131.13639
(Subset 6)
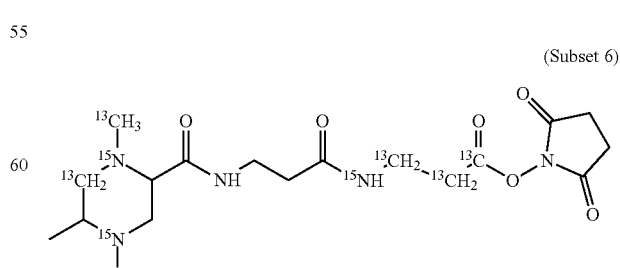
TMT-5-24-132.12711

-continued
(Subset 6)
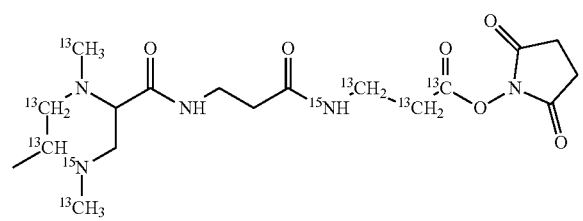
TMT-5-24-132.13343
(Subset 6)
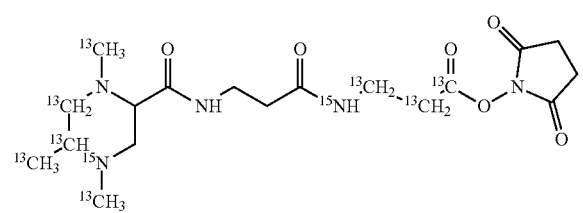
TMT-5-24-132.13975
(Subset 7)
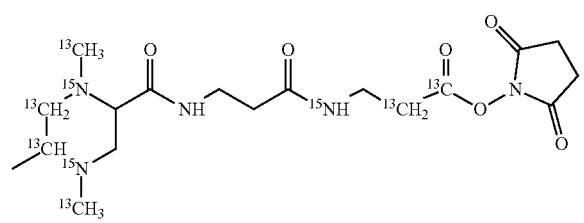
TMT-5-24-133.13046
(Subset 7)
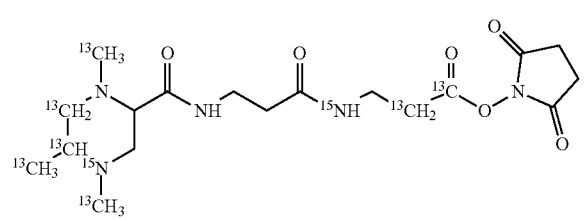
TMT-5-24-133.13678
(Subset 7)
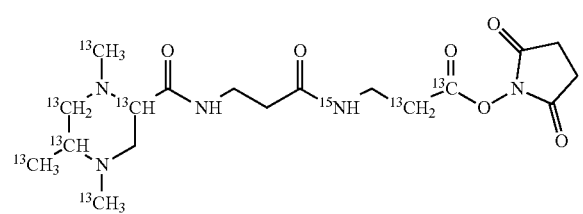
TMT-5-24-133.1431
-continued
(Subset 8)
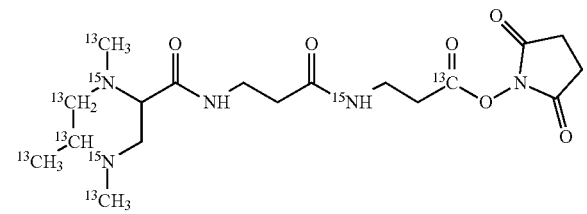
TMT-5-24-134.13382
(Subset 8)
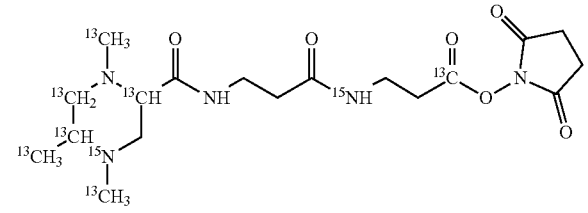
TMT-5-24-134.14014
(Subset 8)
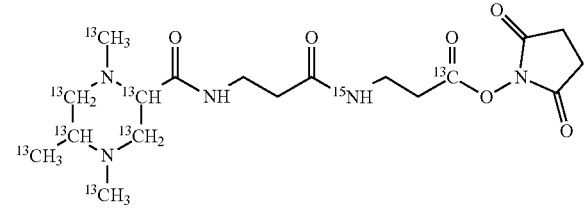
TMT-5-24-134.1523
(Subset 9)
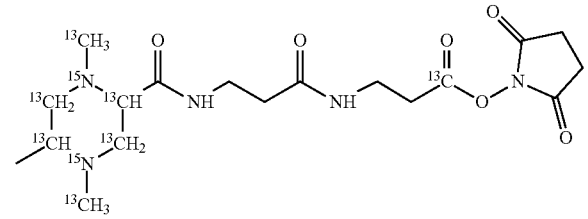
TMT-5-24-135.13717
(Subset 9)
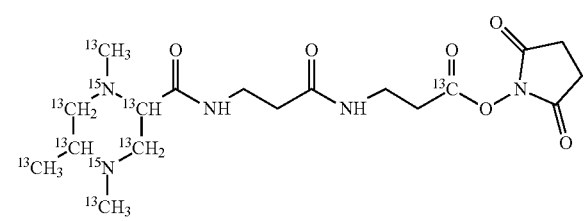
TMT-5-24-135.14349

(Subset 10)

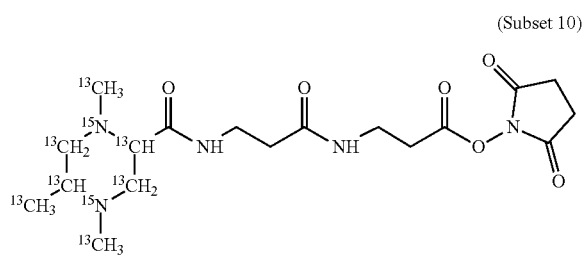

TMT-5-24-136.14053

Alternative heavy isotope substitutions could also be introduced with additional fixed substitutions of hydrogen, deuterium, $^{12}$C or $^{14}$N as illustrated below:

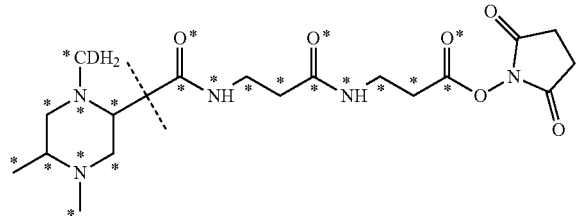

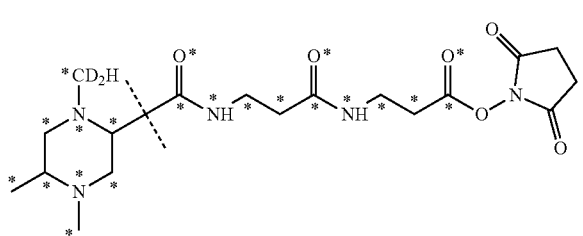

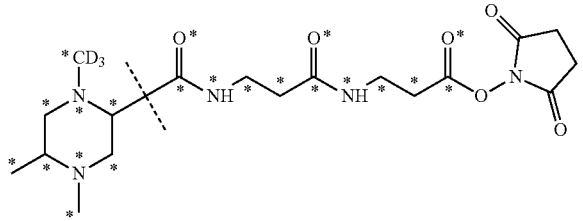

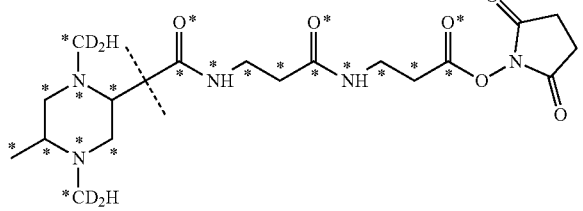

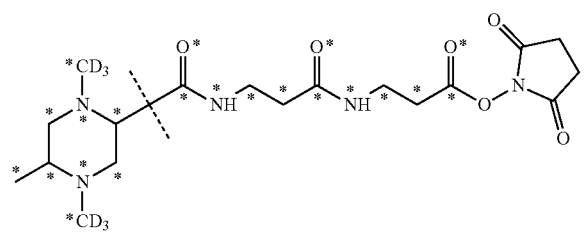

wherein * represents that oxygen is $^{18}$O, carbon is $^{13}$C, nitrogen is $^{15}$N or hydrogen is $^{2}$H, and one or more * may be present.

Embodiment 6

The mass label has structure:

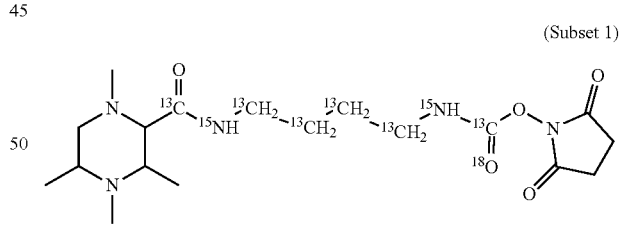

wherein * represents that oxygen is $^{18}$O, carbon is $^{13}$C, nitrogen is $^{15}$N or hydrogen is $^{2}$H, and wherein one or more * may be present.

Figure 8:
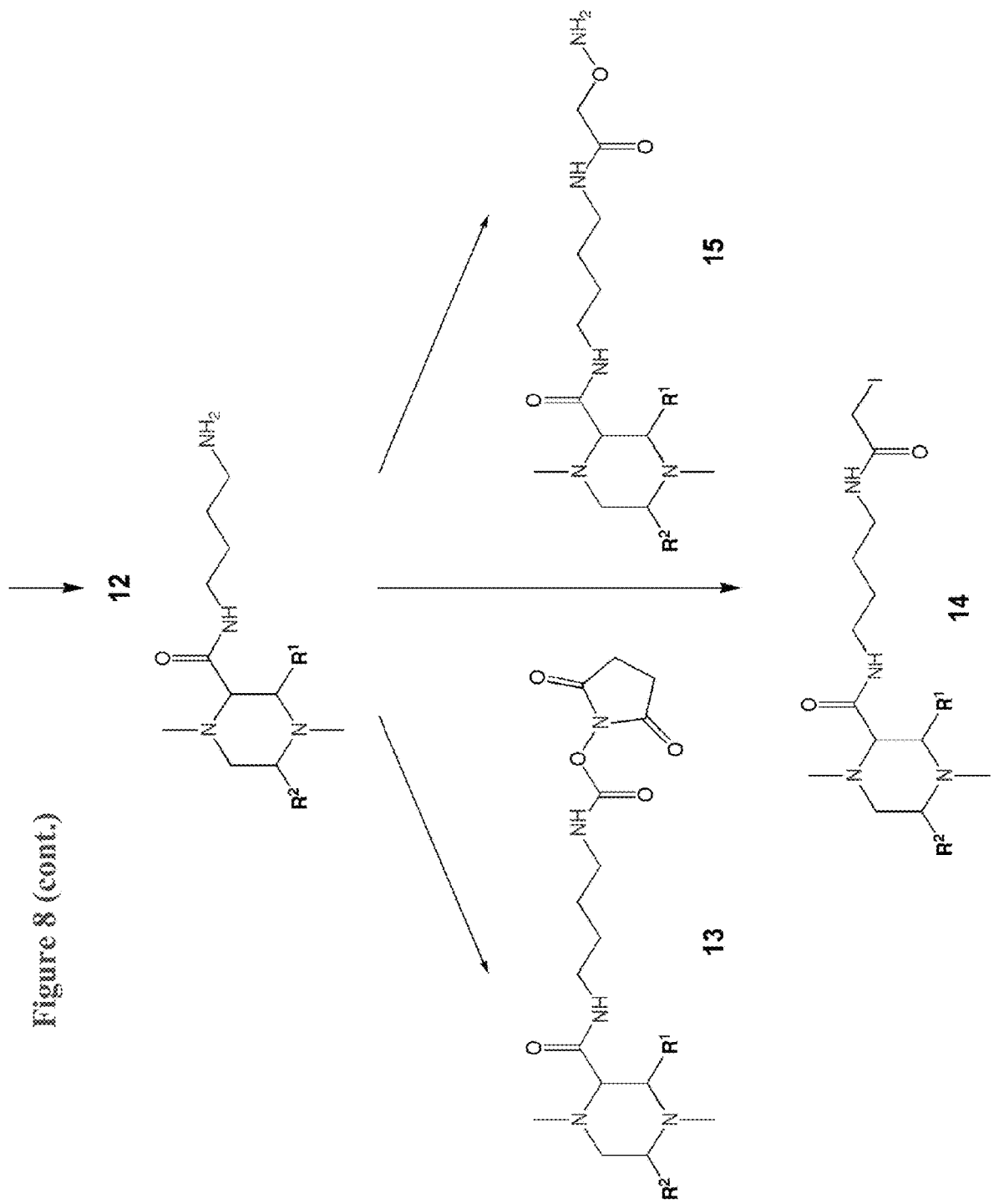
FIG. 8: Schematic illustration of the synthesis and coupling of mass modifier linker composed of 1,4-diaminobutane to the reporter structures of this invention.

The synthesis of the reporter moiety X of Embodiment 6 is shown in FIG. 4 and the addition of the diaminobutane linker is shown in FIG. 8. The synthesis of the tags of this invention is discussed in more detail in the experimental section of the present document.

An example of a set of n=27 mass labels comprising the mass series modifying groups $^{13}$C or $^{15}$N is shown below:

(Subset 1)

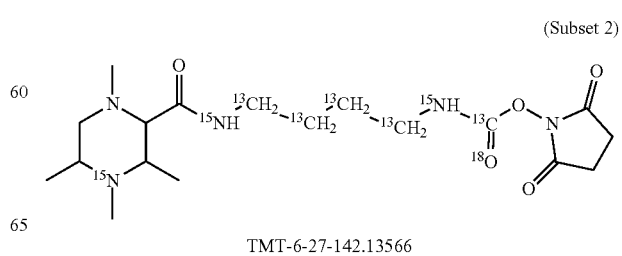

TMT-6-27-141.13862

(Subset 2)

TMT-6-27-142.13566

(Subset 2)
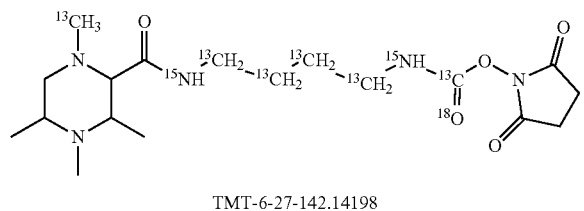
TMT-6-27-142.14198
(Subset 3)
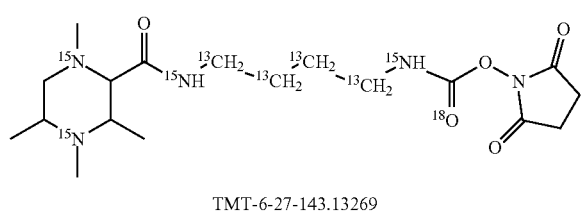
TMT-6-27-143.13269
(Subset 3)
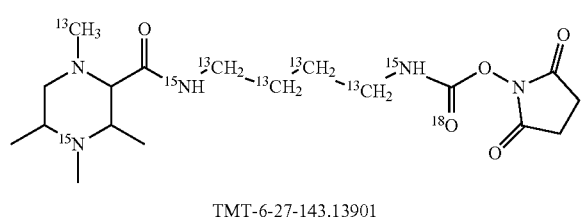
TMT-6-27-143.13901
(Subset 3)
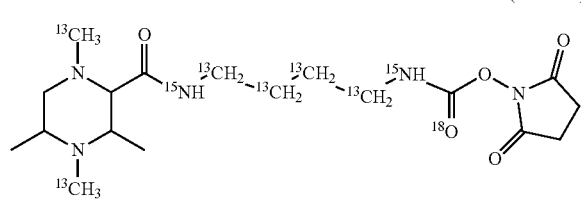
TMT-6-27-143.14533
(Subset 4)
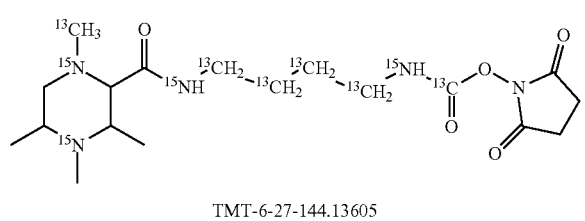
TMT-6-27-144.13605
(Subset 4)
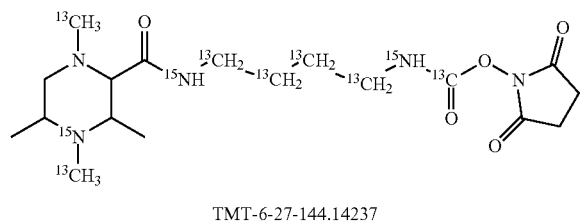
TMT-6-27-144.14237
(Subset 4)
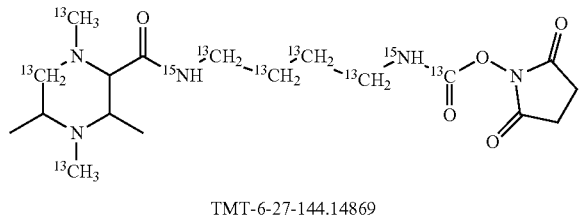
TMT-6-27-144.14869
(Subset 5)
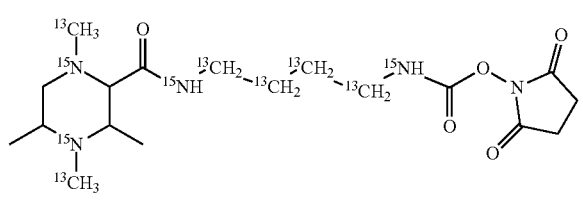
TMT-6-27-145.1394
(Subset 5)
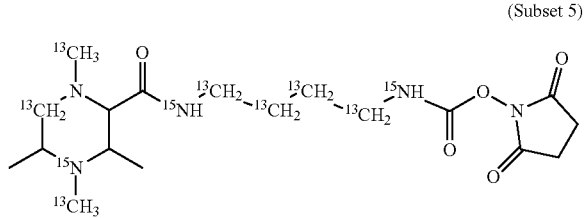
TMT-6-27-145.14572
(Subset 5)
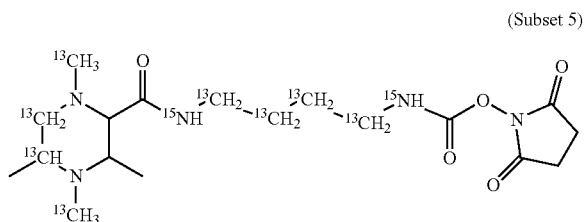
TMT-6-27-145.15204
(Subset 6)
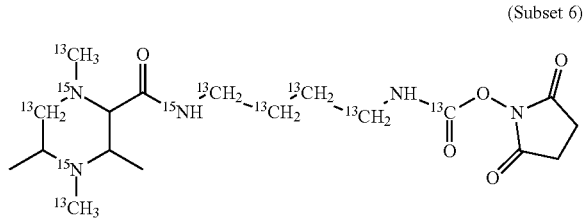
TMT-6-27-146.14276
(Subset 6)
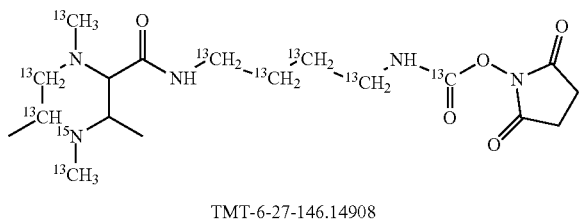
TMT-6-27-146.14908

(Subset 6)

TMT-6-27-146.1554

(Subset 7)

TMT-6-27-147.14611

(Subset 7)

TMT-6-27-147.15243

(Subset 7)

TMT-6-27-147.15875

(Subset 8)

TMT-6-27-148.14947

(Subset 8)

TMT-6-27-148.15579

(Subset 8)

TMT-6-27-148.16211

(Subset 9)

TMT-6-27-149.15282

(Subset 9)

TMT-6-27-149.15914

(Subset 9)

TMT-6-27-149.16546

(Subset 10)

TMT-6-27-150.15618

(Subset 10)

TMT-6-27-150.1625

-continued (Subset 11)

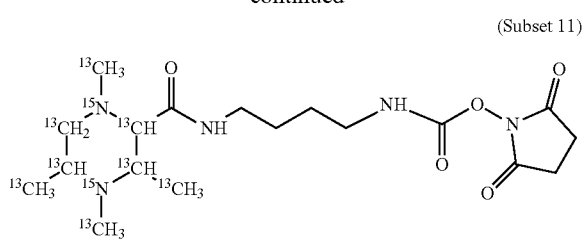

TMT-6-27-151.15953

Alternative heavy isotope substitutions could also be introduced with additional fixed substitutions of hydrogen, deuterium, $^{12}$C or $^{14}$N as illustrated below:

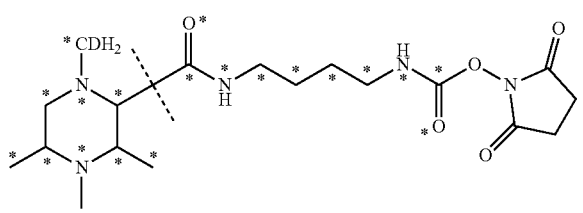

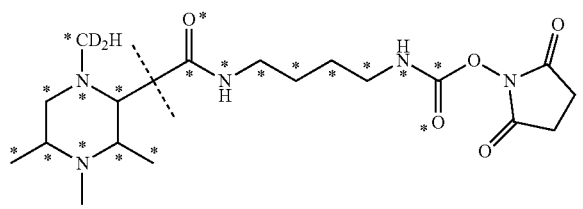

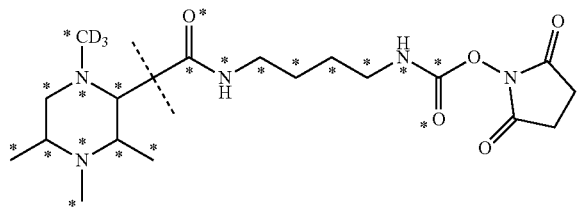

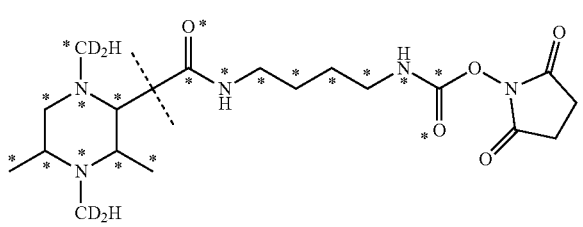

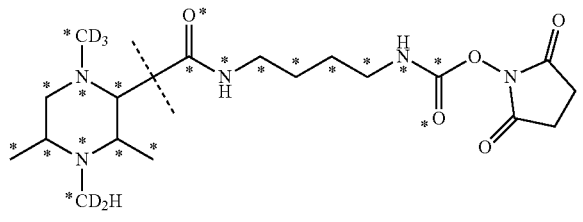

-continued

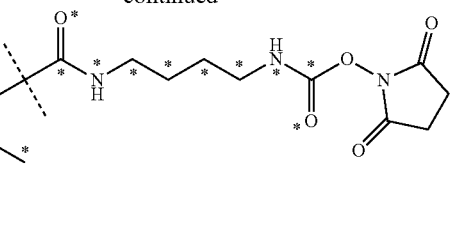

wherein * represents that oxygen is $^{18}$O, carbon is $^{13}$C, nitrogen is $^{15}$N or hydrogen is $^{2}$H, and one or more * may be present.

It will be immediately appreciated that the additional deuterated tag sets shown are all isotopes of the tags in Embodiment Set 6 and it is possible to select subsets of all the possible deuterated tags to give sets of tags that are approximately isobaric with the tags in Embodiment Set 6. This means that peptides labelled with tags from Embodiment Set 6 would be co-selectable with peptides labelled with any related deuterated tags.

In another aspect, the present invention relates to a set of two or more mass labels, hereinafter referred to as "the second set of mass labels of the invention", wherein each label comprises the formula:

X-L-M-Re wherein X is a reporter moiety having an exact mass, L is a bond cleavable by collision in a mass spectrometer, M is a mass modifier, and Re is a reactive functionality for attaching the mass label to an analyte or the analyte, and X comprises the following general formula:

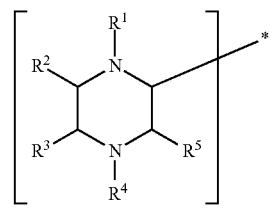

wherein each of $R^1$, $R^2$, $R^3$, $R^4$ and $R^5$ is independently H, a substituted or unsubstituted straight or branched $C_1$-$C_{10}$ alkyl group, or a structure selected from methyl, ethyl, propyl or n-propyl, isopropyl, butyl or n-butyl, isobutyl, sec-butyl, tert-butyl, pentyl or n-pentyl, neopentyl, tert-pentyl, iso-pentyl, sec-pentyl and 3-pentyl.

The definitions and particular and preferred embodiments of the first set of mass labels of the invention are equally applicable to the second set of mass labels of the invention.

The individual mass labels described previously in the context of the first and the second sets of mass labels of the invention constitute additional aspects of the present invention.

Arrays of Mass Labels

The present invention also provides an array of mass labels, hereinafter referred to as "the array of mass labels of the invention", comprising two or more sets of mass labels according to the first and the second sets of mass labels of the invention.

The definitions and particular and preferred embodiments described in detail in the context of the first set of mass labels of the invention apply equally to the array of mass labels of the invention.

In an embodiment, the integer mass of each of the mass labels of any one set in the array is different from the integer mass of each of the mass labels of every other set in the array.

In a preferred embodiment, each mass label in a set comprises:
  a) a mass series modifying group having the same integer mass as every other mass label in the set, and
  b) a different integer mass to the mass labels of all the other sets of the array.

In a particularly preferred embodiment the reporter moiety X comprises the mass series modifying group.

In one embodiment each mass label in a set comprises the same mass series modifying group.

In another embodiment, each mass label in a set comprises a mass series modifying group which is:
  a) the same; or
  b) an isotopologue of the mass series modifying group of all other mass labels of the array.

In a preferred embodiment, each mass label in a set comprises a mass series modifying group which is an isotopologue of the mass series modifying group of all other mass labels of the array.

Methods of Mass Spectrometry Analysis

The present invention also provides for a method of mass spectrometry analysis, hereinafter referred to as "the method of mass spectrometry analysis of the invention", which method comprises detecting an analyte by identifying by mass spectrometry a mass label or combination of mass labels relatable to the analyte, wherein the mass label is a mass label from the first or the second set of mass labels of the invention, or the array of mass labels of the invention, as defined in the previous aspects of the present invention.

In one embodiment, the method of mass spectrometry analysis of the invention comprises:
  a) providing a plurality of samples, wherein each sample is differentially labelled with a mass label or a combination of mass labels, wherein the mass label(s) are from the first or the second set of mass labels of the invention, or the array of mass labels of the invention;
  b) mixing the plurality of labelled samples to form an analysis mixture comprising labelled analytes;
  c) optionally detecting the labelled analytes in a mass spectrometer;
  d) dissociating the labelled analytes in the mass spectrometer to form mass labels and/or analyte fragments comprising intact mass labels;
  e) detecting the mass labels and/or analyte fragments comprising intact mass labels;
  f) optionally dissociating the mass labels in the mass spectrometer to release the reporter moieties, and detecting the reporter moieties;
  g) optionally dissociating the reporter moieties formed in step f) to form fragments, and detecting the fragments;
  h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

In a particular embodiment, the dissociation is, preferably, collision induced dissociation in a mass spectrometer.

In another particular embodiment, a complement ion is formed in step d) by neutral loss of carbon monoxide from the linker L.

Preferably the methods described herein may be performed in a mass spectrometer with a resolution of greater than 60,000 at a mass-to-charge ratio of 400, preferably a resolution of greater than 100,000 at a mass-to-charge ratio of 400, most preferably greater than 250,000 at a mass-to-charge ratio of 400.

The analytes may be identified on the basis of i) the mass spectrum of the labelled analytes; or ii) the mass spectrum of the mass labels and/or analyte fragments comprising an intact mass label; or iii the mass spectrum of the reporter moieties or fragments of reporter moieties. When identification according to ii) occurs, the analyte fragment preferably comprises an intact mass label is a b-series ion comprising an intact mass label, preferably a b1 ion. The analytes may be identified on the basis of the mass spectrum of the reporter moieties X or fragments of reporter moieties X.

Thus, in one embodiment, the analytes may be identified on the basis of the mass spectrum of the labelled analytes.

In another embodiment, the analytes may be identified on the basis of the mass spectrum of the mass labels and/or analyte fragments comprising an intact mass label. In a preferred embodiment, the analyte fragment comprising an intact mass label is a b-series ion comprising an intact mass label, preferably a b1 ion.

In another embodiment, the method of mass spectrometry analysis of the invention comprises:
  a) providing a plurality of samples, wherein each sample is differentially labelled with a mass label or a combination of mass labels, wherein the mass label(s) are from the first or the second set of mass labels of the invention, or the array of mass labels of the invention;
  b) mixing the plurality of labelled samples to form an analysis mixture comprising labelled analytes;
  c) detecting the labelled analytes in a mass spectrometer;
  d) dissociating the labelled analytes in the mass spectrometer to release the reporter moieties, and detecting the complement ions comprising the remainder of the mass label attached to the analyte or a fragment of the analyte;
  e) optionally one or more further steps of dissociating the complement ions formed in step d to form fragments, and detecting the fragments;
  f) identifying the analytes on the basis of the mass spectrum of the labelled analytes and/or the mass spectrum of the complement ions and/or fragments thereof.

In a particular embodiment, the dissociation is, preferably, collision induced dissociation in a mass spectrometer.

In another particular embodiment, a complement ion is formed in step d) by neutral loss of carbon monoxide from the linker L.

Preferably the methods described herein may be performed in a mass spectrometer with a resolution of greater than 60,000 at a mass-to-charge ratio of 400, preferably a resolution of greater than 100,000 at a mass-to-charge ratio of 400, most preferably greater than 250,000 at a mass-to-charge ratio of 400.

Many of the mass labels of this invention are differentiated from each other by very small mass difference, sometimes of the order of only 1 millidalton. It has already be established that current Orbitrap instrumentation can resolve reporter ions with 6.3 millidalton mass differences (Marshall et al., 1998, cited supra). However, for mass labels that are differentiated from each other by the smallest mass differences, higher resolution may be necessary and this can currently be achieved routinely on commercially available Fourier Transform Ion Cyclotron Resonance mass spectrometers.

Time-of-Flight (TOF) mass spectrometers are a further example of a type of mass spectrometer from which high resolution, high mass accuracy data may be obtained depending on the length of the flight tube. Commercially available, Multi-turn (Okumura, D. et al., (2005) *Eur J Mass Spectrom* (Chichester, Eng), 11, 261-266) and Spiral TOF (Shimma, S. et al., (2012) *PLoS One*, 7, e37107) geometries can already achieve mass resolution similar to Orbitraps.

The Orbitrap mass spectrometer consists of an outer barrel-like electrode and a coaxial inner spindle-like electrode that form an electrostatic field with quadro-logarithmic potential distribution (Hu, Q. et al., (2005) *J Mass Spectrom*, 40, 430-443 & Makarov, A. (2000) *Anal Chem*, 72, 1156-1162). Image currents from dynamically trapped ions are detected, digitized and converted using Fourier transforms into frequency domain data and then into mass spectra. Ions are injected into the Orbitrap, where they settle into orbital pathways around the inner electrode. The frequencies of the orbital oscillations around the inner electrode are recorded as image currents to which Fourier Transform algorithms can be applied to convert the frequency domain signals into mass spectra with very high resolutions.

In Fourier Transform Ion Cyclotron Resonance (FTICR) mass spectrometry, a sample of ions is retained within a cavity like and ion trap but in FTICR MS the ions are trapped in a high vacuum chamber by crossed electric and magnetic fields (Marshall, A. G. et al., (1998) *Mass Spectrom Rev*, 17, 1-35 & Marshall, A. G. and Hendrickson, C. L. (2008) *Annu Rev Anal Chem* (Palo Alto Calif.), 1, 579-599). The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates', which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis. The mass resolution of FTICR instruments increases with the strength of the applied magnetic field and very high resolution (>1,000,000) analysis can be achieved (Schaub, T. M. et al., (2008) *Anal Chem*, 80, 3985-3990).

For induced fragmentation experiments, FTICR instruments can perform in a similar manner to an ion trap—all ions except a single species of interest can be ejected from the FTICR cavity. A collision gas can be introduced into the FTICR cavity and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole or Time-of-Flight instrument, for example.

In a time-of-flight mass spectrometer, pulses of ions with a narrow distribution of kinetic energy are caused to enter a field-free drift region. In the drift region of the instrument, ions with different mass-to-charge ratios in each pulse travel with different velocities and therefore arrive at an ion detector positioned at the end of the drift region at different times. The length of the drift region determines mass resolution of TOF instruments and this may be readily increased. The analogue signal generated by the detector in response to arriving ions is immediately digitised by a time-to-digital converter. Measurement of the ion flight-time determines mass-to-charge ratio of each arriving ion. There are a number of different designs for time of flight instruments. The design is determined to some extent by the nature of the ion source. In Matrix Assisted Laser Desorption Ionisation Time-of-Flight (MALDI TOF) mass spectrometry pulses of ions are generated by laser excitation of sample material crystallized on a metal target. These pulses form at one end of the flight tube from which they are accelerated.

In order to acquire a mass spectrum from an electrospray ion source, an orthogonal axis TOF (oaTOF) geometry is used. Pulses of ions, generated in the electrospray ion source, are sampled from a continuous stream by a 'pusher' plate. The pusher plate injects ions into the Time-Of-Flight mass analyser by the use of a transient potential difference that accelerates ions from the source into the orthogonally positioned flight tube. The flight times from the pusher plate to the detector are recorded to produce a histogram of the number of ion arrivals against mass-to-charge ratio. This data is recorded digitally using a time-to-digital converter.

For the purposes of resolving all of the possible tags of this invention, mass spectrometers with high resolution are required but the nature of the instruments is not particularly important to the practice of this invention. In addition, many of the tags that have been described in this application can still be resolved on instruments with only single dalton resolution as long as subsets of the possible tags that are separated by single dalton mass differences are used.

The invention is detailed below by means of the following examples, which are merely illustrative and by no means limiting the scope of the invention.

EXAMPLES

Syntheses of Mass Labels

Example 1

Synthesis of N,N-Dimethyl Piperazine-2-Carboxylic Acid Ring Isotopes

The synthesis of N,N'-orthogonally protected piperazine-2-carboxylic acid has been described previously in the literature (Warshawsky et al., 1997, J Org Chem 62:6439-40). In FIG. 3, the schematic steps up to product 5 illustrate this previously published route, in which BOC-protected serine is converted to the corresponding protected serine beta-lactone using modified Mitsunobu conditions (Arnold et al., 1985, J Am Chem Soc 107:7105-9) to give product 1, which then undergoes ring-opening by reaction with allylamine to give product 2. The ring-opening reaction can give rise to either the amide or the amine and the selectivity of this reaction is sensitive to solvents and nucleophile (Ratemi &Vederas, 1994, Tetrahedron Letters 35:7605-8). The resulting secondary amine is protected with a CBz group using standard Schotten-Baumann conditions to give product 3. Product 3 is then induced to undergo a ring-closing reaction by ozonolysis of the alkene and work-up with dimethylsulphide to give the aldehyde, which then spontaneously undergoes ring closure to form product 4, the ring hemiaminal. Chemoselective reduction of the hemiaminal can be effected using triethylsilane and boron trifluoride diethyl etherate in $CH_2Cl_2$ (Pedregal et al., 1994, Tetrahedron Letters 35:2053-6) to afford product 5. The BOC group at 1' position of the doubly protected ring can be selectively removed with Trifluoroacetic Acid (TFA) in Dichloromethane (DCM) to give product 6. Removal of the BOC is followed by reductive methylation using formaldehyde with triacetoxyborohydride to give product 7. The CBz group is then removed from the 4' position by reduction with hydrogen using a palladium/charcoal catalyst in methanol to give product 8. Finally, this is followed in turn by a further reductive methylation at the 4' nitrogen to afford N,N'-dimethyl-piperazine-2-carboxylic acid (product 9). There are numerous commercially available isotopes of serine and formaldehyde (see FIG. 6 although this is not a fully comprehensive list) but heavy isotopes of allylamine are not catalogue items. However, heavy isotopes of allylamine could be fairly readily made. Deuterated forms of formaldehyde are commercially available and additional deuterium can be introduced into the ring by using triacetoxyborodeuteride for the reductive methylation steps. In this way multiple heavy isotope versions of the piperazine-2-carboxylic acid ring can be prepared to produce the tags of this invention. It also advantageous that the methyl substitutions at the nitrogen centres in the rings can be carried out independently to allow the number of deuterium atoms to be independently controlled. This synthesis allows rings with 1, 2, 3, 4, 5 or 6 deuterium atoms to be made.

Since allylamine isotopes are not readily commercially available but heavy isotopes of ethanolamine are readily available, FIG. 4 illustrates a variation of the route shown in FIG. 3. In FIG. 4, BOC-protected serine (i.e. $R^5$ is hydrogen) is converted to the corresponding protected aldehyde using Dess Martin Periodinane (DMP) (Dess & Martin, 1983, J Org Chem 48:4155-6) to give product 1, which then undergoes reductive alkylation by reaction with ethanolamine (where $R^3$ is hydrogen in FIG. 4) and triacetoxyborohydride to give product 2. The resulting secondary amine is protected with a CBz protecting group using standard Schotten-Baumann conditions to give product 3. Product 3 is then induced to undergo a ring-closing reaction by conversion of the alcohol with DMP to the aldehyde, which then spontaneously undergoes ring closure to form product 4, the ring hemiaminal. Chemoselective reduction of the aminal can be effected using triethylsilane and boron trifluoride diethyl etherate in $CH_2Cl_2$ (Pedregal et al., 1994, cited supra) to afford product 5. The BOC group at 1' position of the doubly protected ring can be selectively removed with Trifluoroacetic Acid (TFA) in Dichloromethane (DCM) to give product 6. Removal of the BOC is followed by reductive methylation with formaldehyde with triacetoxyborohydride to give product 7. The CBz group is then removed from the 4' position by reduction with hydrogen using a palladium/charcoal catalyst in methanol to give product 8. Finally, this is followed in turn by reductive methylation at the 4' nitrogen to afford N,N'-dimethyl-piperazine-2-carboxylic acid (product 9).

Figure 5:
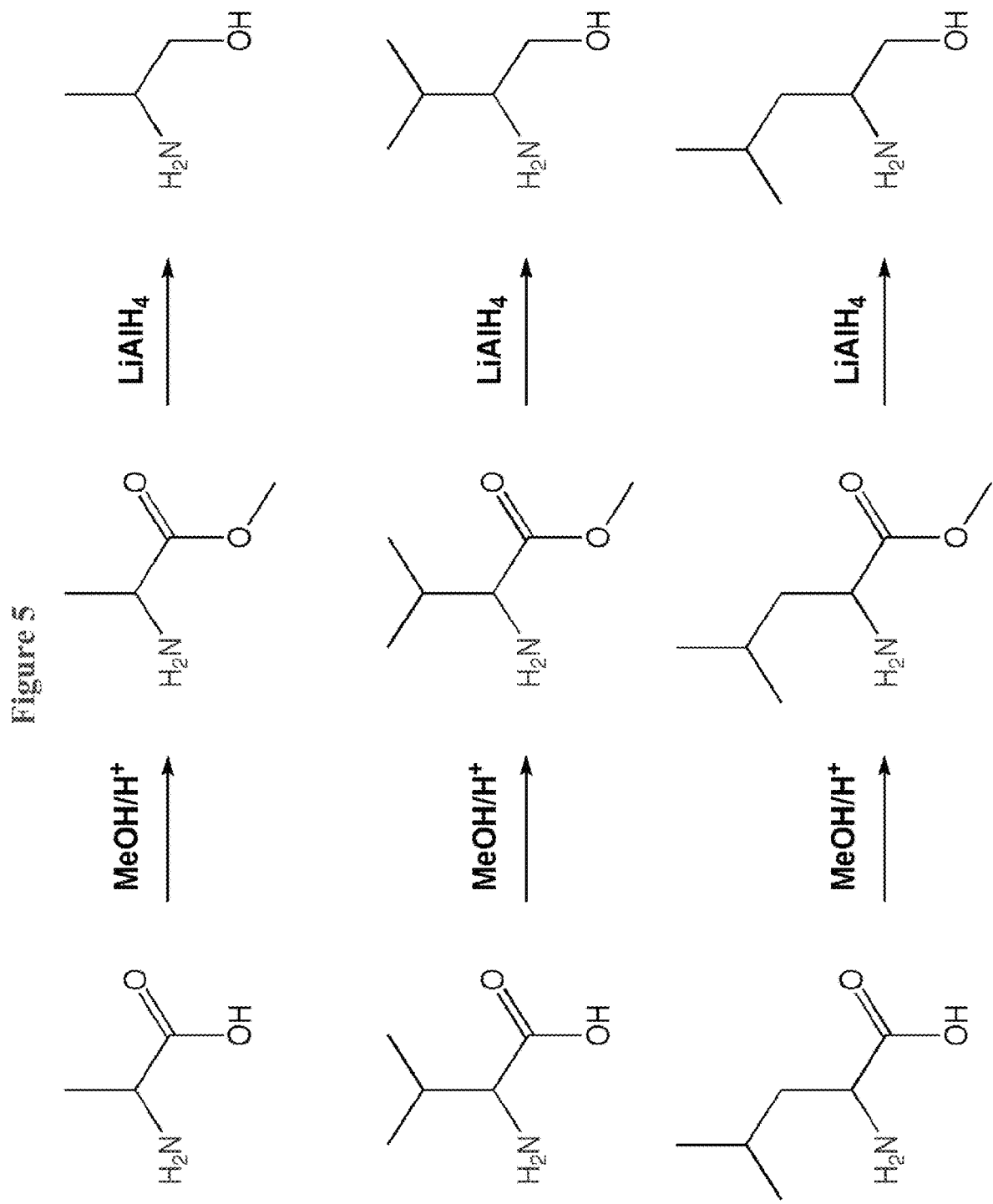
FIG. 5: Schematic representation of a synthetic route to convert alpha-amino acids, that are readily available with heavy isotope doping, to alpha-amino alcohols that may be used in the synthesis method shown in FIG. 4.

Piperazine rings with more substituents can be synthesized using the same synthetic route as that shown in FIG. 4 but with different starting components. For example, serine can be substituted for threonine (i.e. $R^5$ is $CH_3$) to give N,N'-dimethyl-5-methyl-piperazine-2-carboxylic acid. Similarly, ethanolamine can be substituted for L-alaninol (where $R^3$ is $CH_3$), which can be derived from alanine as shown in FIG. 5. Alternatively, ethanolamine can be substituted for L-valinol (where $R^3$ is isopropyl), which can be derived from valine as shown in FIG. 5. Furthermore, ethanolamine can be substituted for L-leucinol (where $R^3$ is isobutyl), which can be derived from leucine as shown in FIG. 5. A variety of heavy stable isotope versions of threonine, alanine, valine and leucine are commercially available (see FIG. 6 for a non-comprehensive list of available heavy isotopes) enabling the synthesis of a multitude of tags according to this invention. It should be apparent to one of ordinary skill in the art that a large number of alternative alpha-amino acids could be converted to the corresponding alpha-amino alcohol for the synthesis of the mass tags of this invention.

Example 2

Coupling of Substituted Piperazine-2-Carboxylic Acid Rings to Linkers

Figure 2:
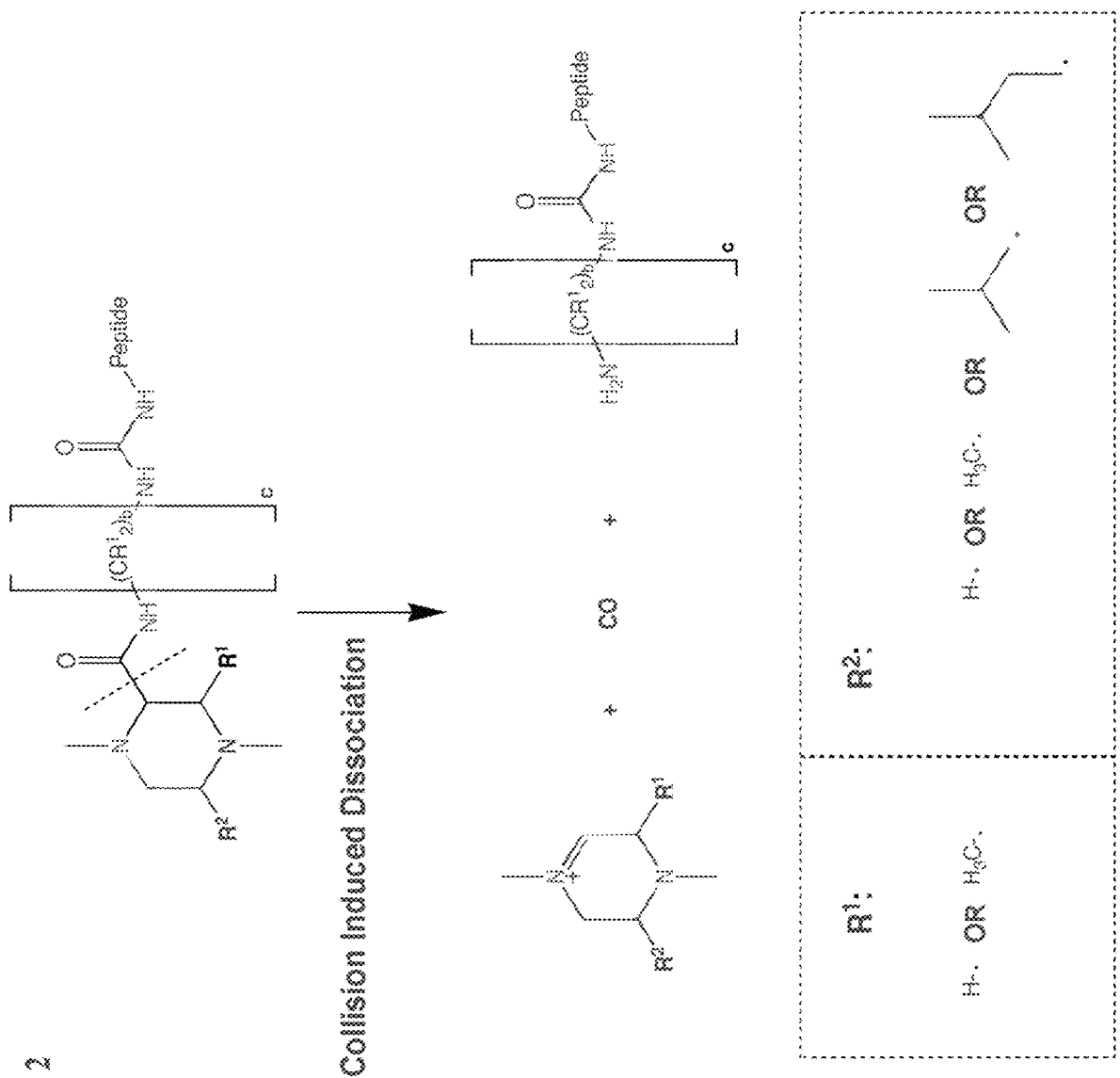
FIG. 2: Schematic of the predicted fragmentation pathway of the substituted piperazine-2-carboxylic acid mass label reporters according to this invention (depicted structure is hypothetical and illustrated only for the purpose of predicting the mass-to-charge ratio of expected reporter ions). Also shown is a second example of a suitable mass modifier linker according to this invention.

The substituted piperazine-2-carboxylic acid rings that form the basis of this invention are used as reporter ions in isobaric mass tags as shown in FIGS. 1 and 2. The reporter moieties X are linked to mass normalizer groups M to create isobaric and pseudo-isobaric tags and mass series offset tags, as explained previously.

FIG. 7 illustrates the coupling of a double beta-alanine linker to a substituted piperazine-2-carboxylic acid ring. Beta-alanine protected at the amino group with a BOC protecting group (product 10) is coupled to beta-alanine protected at the carboxyl group with a Benzyl protecting group (product 11) to give the protected double-beta alanine linker (product 12). The BOC group is removed to give the linker with a free amine (product 13), which is in turn coupled to the substituted piperazine-2-carboxylic acid ring (9). The benzyl protecting group is then removed to afford the free acid which can then be converted to an active ester for reaction with amino groups or the carboxylic acid group can be used to introduce other reactive groups as discussed below. Multiple isotopes of beta-alanine are commercially available enabling the production of any of the double beta-alanine linkers depicted in this document.

FIG. 8 illustrates the coupling of a 1,4-diaminobutane linker to a substituted piperazine-2-carboxylic acid ring. 1,4-diaminobutane protected at one of the amino groups with a BOC protecting group (product 10) is directly coupled to the substituted piperazine-2-carboxylic acid ring (9) to give the BOC protected product (11). Preparation of mono-BOC protected symmetric diamines is well known in the literature (Lee et al., 2007, Synthetic Communications: Communications: An International Journal for Rapid Communication of Synthetic Organic Chemistry 37:737-42). The BOC protecting group is then removed to afford the free amine (product 12) which can then be converted to an NHS Carbamate (product 13) by reaction with disuccinimidyl carbonate (DSC). The NHS carbamate is reactive to free amino groups. Alternatively, the free amino group can be used to introduce other reactive groups shown in FIG. 8. The free amine 12 can be reacted with iodoacetic acid anhydride to give the iodoacetmide product (14). Alternatively, the free amine product 12 can be coupled to (BOC-aminooxy)acetic acid (SigmaAldrich). The BOC group can be removed with TCA/DCM to give the aminooxy-derivatised tag (15).

Example 3

Reactive Groups

The example tag shown in FIG. 7 is shown functionalized with a free carboxylic acid. A carboxylic acid tag can be coupled to amino groups with a suitable coupling agent such as a carbodiimide like N,N'-dicyclohexylcarbodiimide. More preferably, the free carboxylic acids are modified to form so-called active esters, which are stable reagents that will react readily with free amino groups without requiring an additional coupling agent. Preferably, the mass label with a free carboxylic acid could be activated to the N-hydroxysuccinimide ester by contacting the free acid with N,N'-disuccinimidyl carbonate in a suitable organic solvent such as dichloromethane.

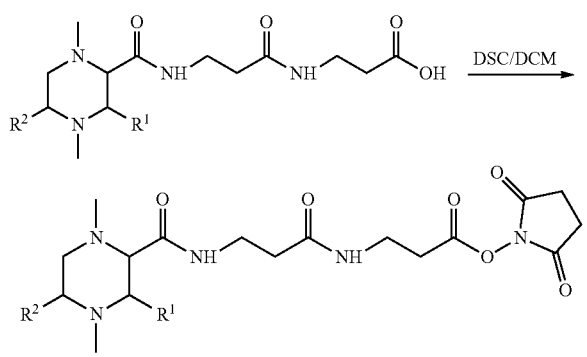

Other preferred active esters may be prepared by coupling a suitable alcohol to mass tags of this invention with a free carboxylic acid using a carbodiimide. Alternatively, a free carboxylic acid can be activated with thionyl chloride to from the acid chloride prior to reaction with an alcohol. Thus, the pentafluorophenol active ester is prepared by coupling the mass label with pentafluorophenol, similarly the nitrophenol ester is prepared by coupling the mass label with nitrophenol. The sulphodichlorophenol (SDP) ester can be prepared by reacting the acid chloride of a mass tag with 3,5-dichloro-4-hydroxybenzenesulphonic acid. Similarly, the 1-hydroxy-7-azabenzotriazole ester, the N-hydroxysulphosuccinimidyl ester, the 2,3,5,6-tetrafluorophenol ester, the 4-sulpho-2,3,5,6-tetrafluorophenol ester and the 3,4-dehydro-4-oxo-1,2,3-benzotriazinyl (DHBT) ester can all be prepared from the corresponding alcohols. The DHBT ester is not typically prepared as a reagent that can be stored or distributed. It is typically prepared in situ immediately prior to use.

Aminoxy-activated forms of the mass labels of this invention can be prepared by coupling Boc-protected aminoxypropylamine to the NHS ester activated forms of two of the mass labels of this invention. The BOC protecting group is then removed under acid conditions to provide the aminoxy reagent.

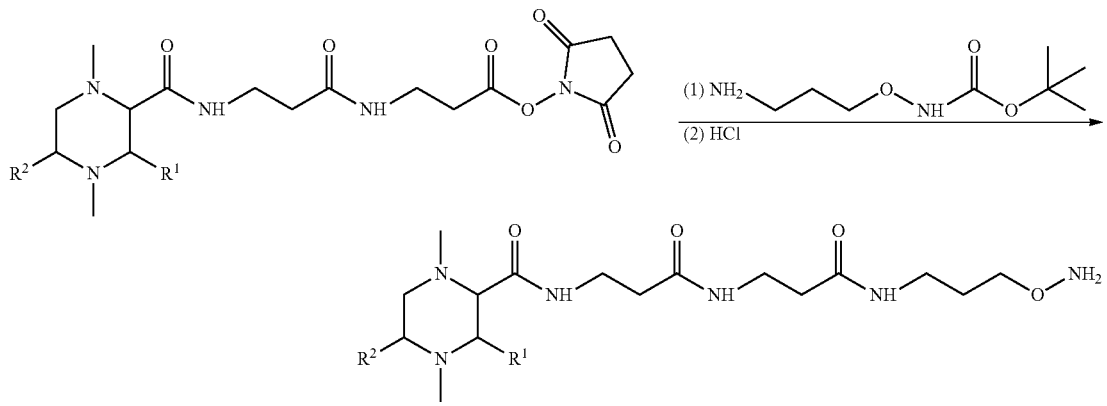

The aminoxy group reacts with carbonyl functions to form an oxime bond, which is quite stable. Carbonyl functions appear in oxidised carbohydrates and steroids and various methods are known in the art for preparing steroid-containing samples, carbohydrate-containing samples or glycoprotein containing samples for labelling with aminoxy-functionalised tagging reagents.

Similarly, hydrazide-activated reagents react with carbonyl groups to form a hydrazone linkage. The hydrazone is moderately stable and compounds labelled this way can be analysed directly or to avoid any chance of the coupling reaction being reversed, the hydrazone may be reduced to a secondary amine. The synthesis of hydrazide-activated forms of the mass labels of this invention can be effected by coupling hydrazine to the NHS ester activated forms of two of the mass labels of this invention.

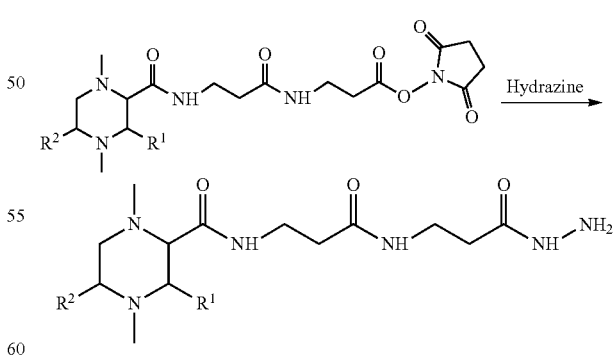

Pyridyldithio-activated forms of the mass labels of this invention may be prepared by coupling of thiopyridine-protected cysteamine to the active ester forms of the mass tag. thiopyridine-protected cysteamine is prepared by reacting cysteamine with dithiopyridine to produce the protected thiol with leaving a free amino group:

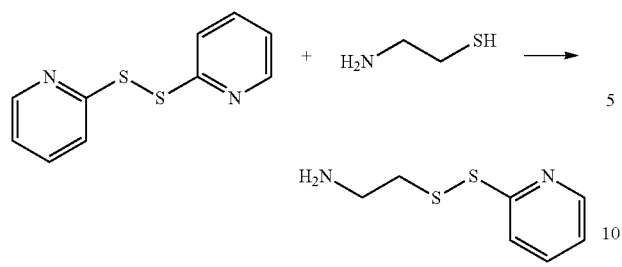

This amine intermediate is then coupled to the NHS ester activated forms of two of the mass labels of this invention to yield the pyridyldithio-activated form of the mass labels of this invention.

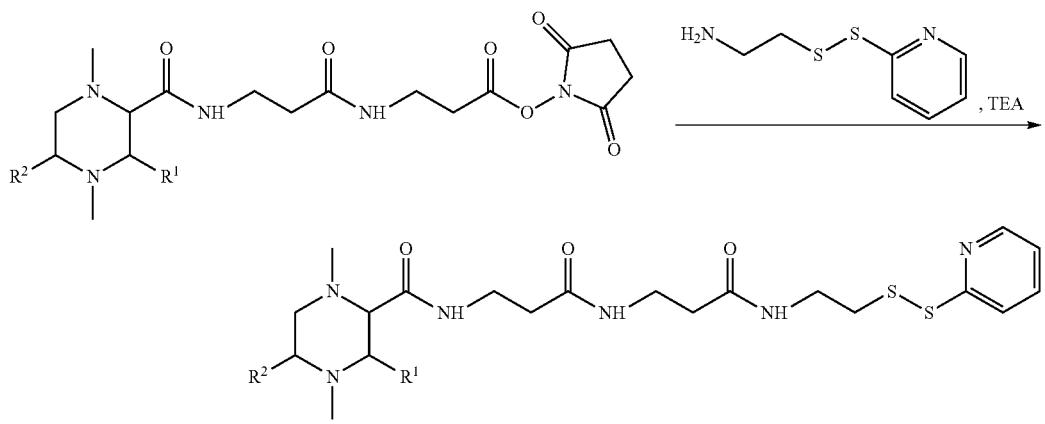

The pyridyldithio-activated form of the mass labels of this invention may be used to couple the mass labels of this invention to thiol functions such as reduced cysteine residues in proteins or peptides. The 2-dithiopyridine group and has several advantages: it shows a high selectivity to label cysteine residues, even at increased pH as often used in buffer solutions useful in proteomic investigations (eg. Triethylammonium bicarbonate TEAB) and it is not labile to exposure to water. Furthermore, this group can be re-cleaved from peptides easily if desired by treatment with any disulfide-reducing reagents.

Amino-functionalised forms of the mass labels can also be prepared from carboxylic acid derivatised tags. In this reaction scheme BOC-protected ethylenediamine is reacted with the NHS-ester activated forms of two of the mass labels of this invention followed by removal of the BOC group to yield amino-functionalised form of the mass labels of this invention. Amino-functionalised mass labels are useful in their own right and may used to couple the mass labels of this invention to carbonyl groups with reduction of the resulting imines.

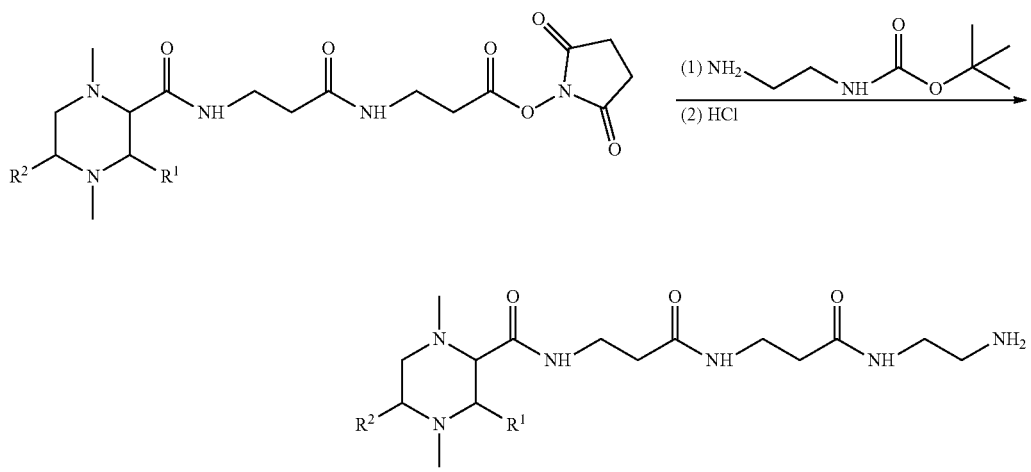

The amino-functionalised forms of the mass labels of this invention may be reacted further to produce haloacetyl forms of the mass tags of this invention by coupling haloacetic acid anhydrides, such as iodoacetic acid anhydride, to the amino-functionalised tags. The resulting iodoacetamide-activated form of the mass labels of this invention may be used to couple the mass labels of this invention to thiol functions such as reduced cysteine residues in proteins or peptides.

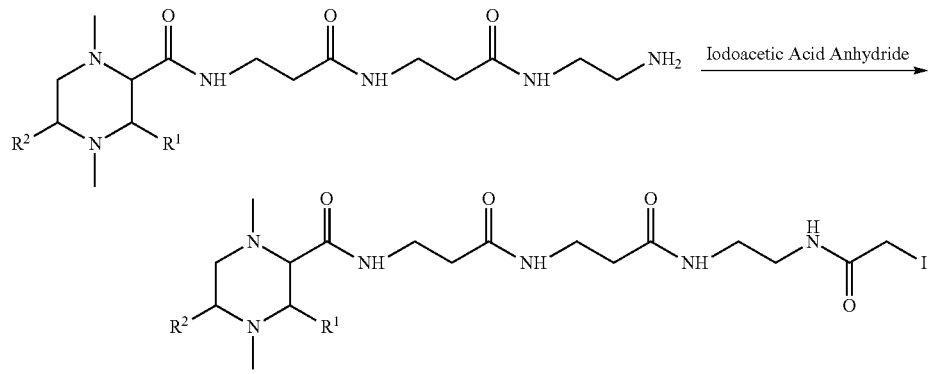

Maleimide compounds are also excellent reagents for thiol labeling and can be readily introduced into tags according to this invention by reaction of amine-modified tags with maleic anhydride in an inert solvent such as dimethylformamide (DMF) followed by dehydration with phosphorus pentoxide to effect ring closure.

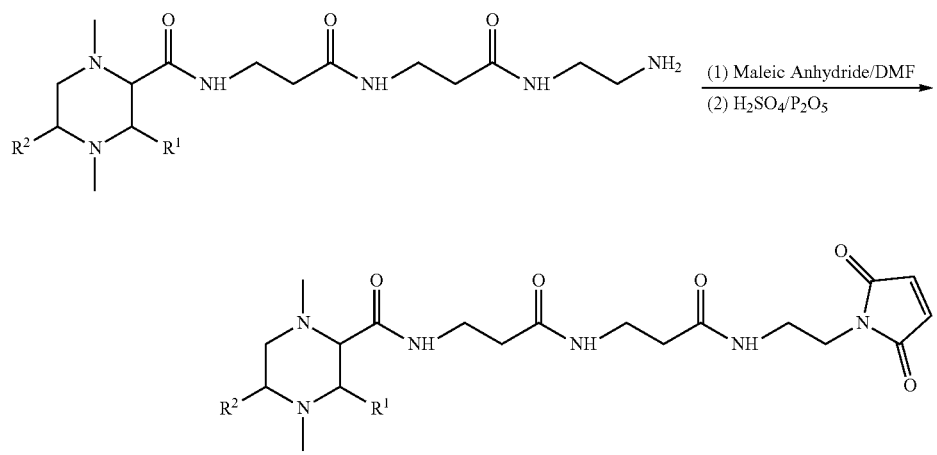

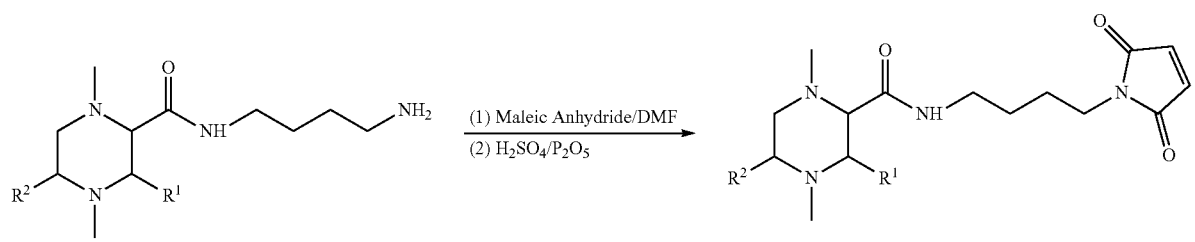

The synthesis of alkyne-activated forms of the mass tags of this invention is shown below.

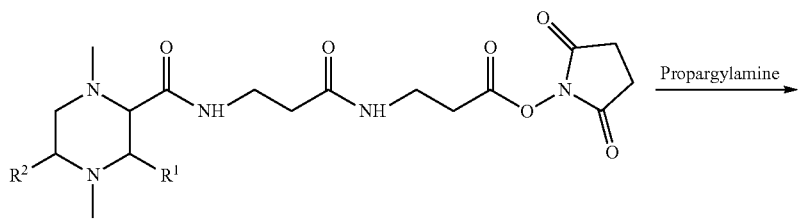

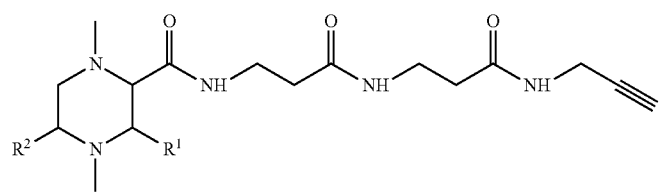

In this reaction scheme propargylamine is reacted with the NHS-ester activated forms of two of the mass labels of this invention to yield alkyne-functionalised form of the mass labels of this invention. Alternatively, amine-derivatised tags of this invention can be coupled to propynoic acid to give an alkyne-functionalised tag:

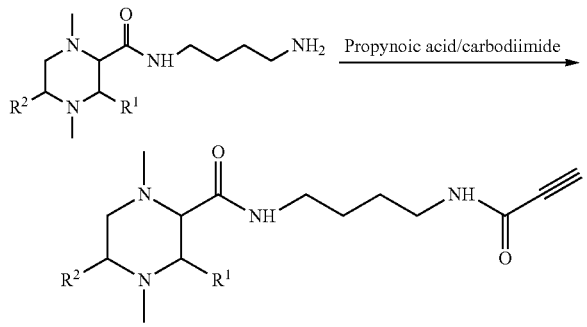

Alkyne-functionalized mass labels may be reacted with azide functionalities via Copper-catalyzed Azide Alkyne Cycloaddition (CuAAC) reaction to form triazole linkages. This is sometimes referred to as the 'Sharpless Reaction' (Rostovtsev et al., 2002, Angew Chem Int Ed 41:2596-9). A variety of azide-based reagents for metabolic labelling of live cells are commercially available and allowing azide-labelled molecules derived from such cells to be labelled with the mass labels of this invention.

The amino-functionalised forms of the mass labels of this invention may be reacted further to produce azide-functionalized forms of the mass labels of this invention by coupling a commercially available NHS-Azide reagent (Thermo Scientific's Pierce Biotechnology division, Rockford, Ill., USA), to the amino-functionalised mass labels. Alternatively, the amino-functionalized mass labels can be converted directly to the azide by reaction with azidification reagent imidazole-1-sulfonyl azide. Imidazole-1-sulfonyl azide is prepared by treating sulfuryl chloride with sodium azide in acetonitrile, followed by the addition of excess imidazole (Goddard-Borger & Stick, 2007, Org Lett 9:3797-800).

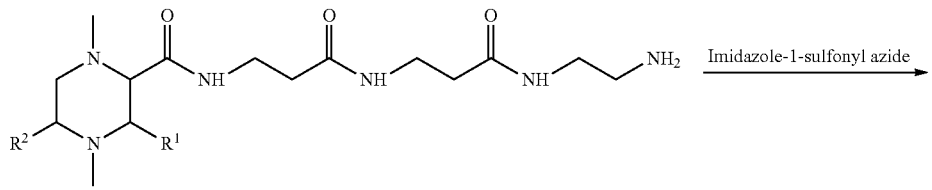

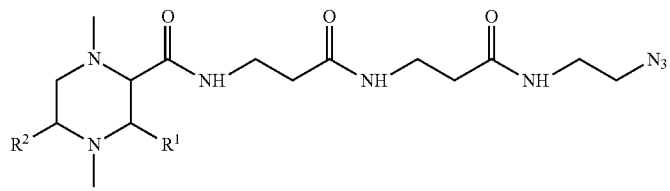

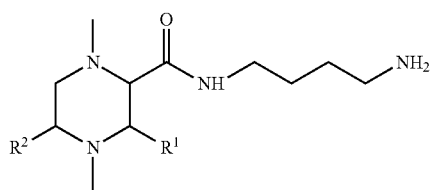 → Imidazole-1-sulfonyl azide → 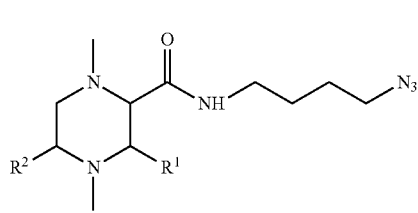

Azide-functionalized tags may be reacted with alkyne functionalities via the 'Sharpless Reaction' or Copper-catalyzed Azide Alkyne Cycloaddition (CuAAC) reaction to form triazole linkages. A variety of alkyne-based reagents for metabolic labelling of live cells are commercially available and allowing alkyne-labelled molecules derived from such cells to be labelled with the tags of this invention.

The examples described herein provide means for the generation of the mass labels and sets of mass labels as set out in Embodiments 1 to 6 previously described in the context of the first set of mass labels of the invention.

The invention claimed is:

1. A set of mass labels, wherein each mass label comprises the formula:

X-L-M-Re wherein:
X is a reporter moiety having an exact mass,
L is a bond cleavable by collision in a mass spectrometer,
M is a mass modifier, and
Re is a) a reactive functionality for attaching the mass label to an analyte or b) the analyte,
wherein each mass label in the set has an integer mass,
wherein each mass label in the set has the same integer mass,
wherein the set comprises two or more subsets of mass labels, each subset comprising one, two or more mass labels,
wherein, when the subset comprises two or more mass labels, the exact mass of the reporter moiety X of each mass label in the subset is different from the exact mass of the reporter moiety X of the mass labels in the same subset and in all other subsets,
wherein each mass label is distinguishable by mass spectrometry, and the set consists of n=5 mass labels having the following structures:

(Subset 5)

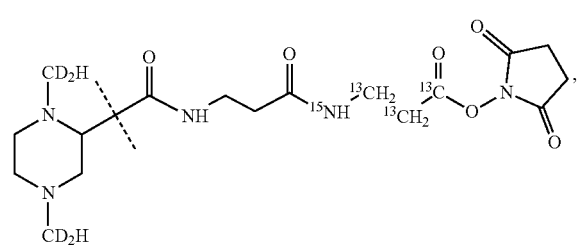

TMT-3-5-1-117.13243

(Subset 6)

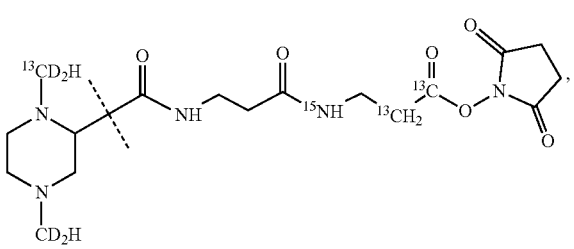

TMT-3-5-118.13579

(Subset 7)

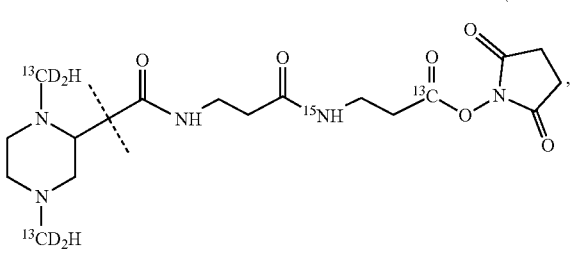

TMT-3-5-119.13914

(Subset 8)

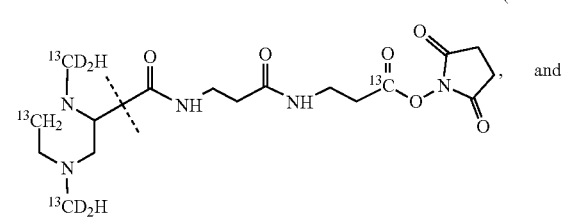

and

TMT-3-5-120.13618

(Subset 9)

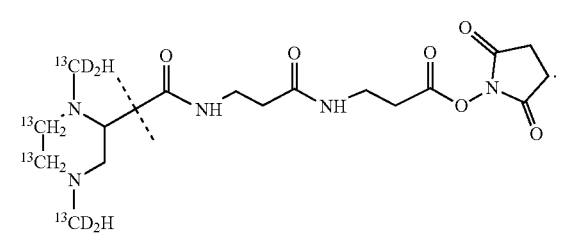

TMT-3-5-121.14585

2. A method of mass spectrometry analysis, the method comprising:
a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=5 mass labels having the following structures:

(Subset 5)

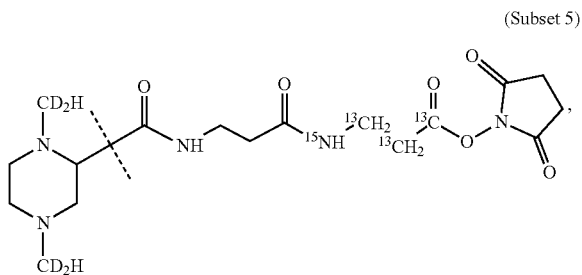

TMT-3-5-1-117.13243

(Subset 6)

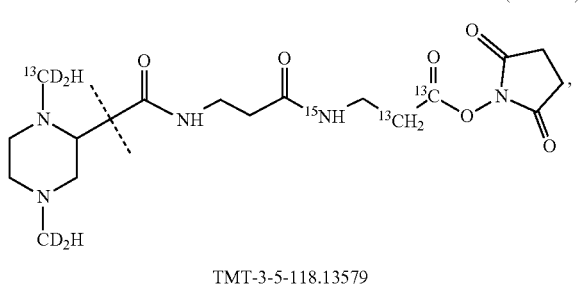

TMT-3-5-118.13579

(Subset 7)

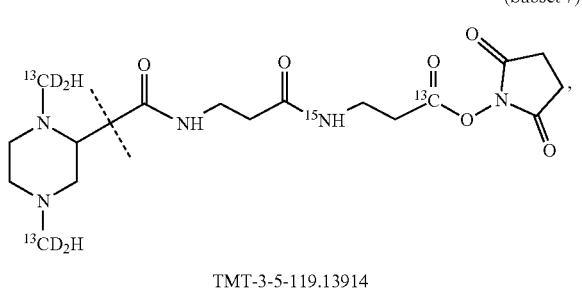

TMT-3-5-119.13914

(Subset 8)

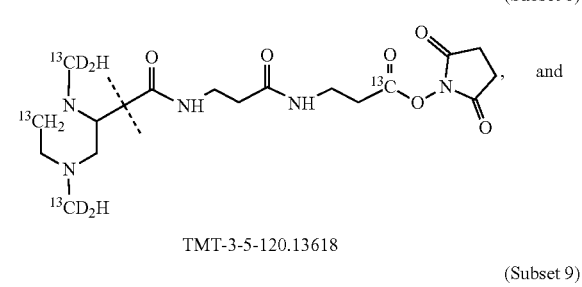

and

TMT-3-5-120.13618

(Subset 9)

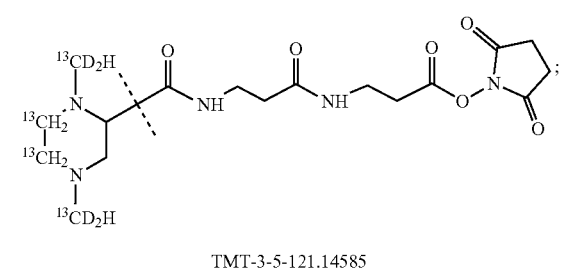

TMT-3-5-121.14585 b) mixing the plurality of differentially labelled samples to form an analysis mixture comprising labelled analytes;

c) optionally detecting the labelled analytes in a mass spectrometer;
d) dissociating the labelled analytes in the mass spectrometer to form mass labels and/or analyte fragments comprising intact mass labels;
e) detecting the mass labels and/or analyte fragments comprising intact mass labels;
f) optionally dissociating the mass labels in the mass spectrometer to release the reporter moieties, and detecting the reporter moieties;
g) optionally dissociating the reporter moieties formed in step f) to form fragments, and detecting the fragments;
h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

3. The method of mass spectrometry analysis according to claim 2, wherein the analytes are identified on the basis of the mass spectrum of the labelled analytes.

4. The method of mass spectrometry analysis according to claim 2, wherein the analytes are identified on the basis of the mass spectrum of the mass labels and/or analyte fragments comprising an intact mass label.

5. The method of mass spectrometry analysis according to claim 4, wherein the analyte fragment comprising an intact mass label is a b-series ion comprising an intact mass label, optionally a b1 ion.

6. The method of mass spectrometry analysis according to claim 2, wherein the analytes are identified on the basis of the mass spectrum of the reporter moieties or fragments of reporter moieties.

7. The method according to claim 2, wherein the dissociation is collision induced dissociation in a mass spectrometer.

8. The method according to claim 2, which method is performed in a mass spectrometer with a resolution of greater than 60,000 at a mass-to-charge ratio of 400.

9. The method according to claim 2, wherein m step d) the complement ion is formed by neutral loss of carbon monoxide from the bond L.

10. A method of mass spectrometry analysis, the method comprising:
a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=5 mass labels having the following structures:

(Subset 5)

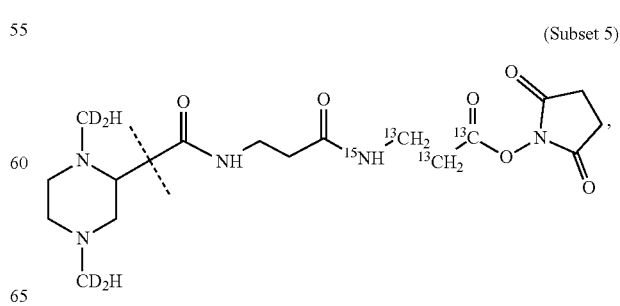

TMT-3-5-1-117.13243

-continued (Subset 6)

TMT-3-5-118.13579

(Subset 7)

TMT-3-5-119.13914

(Subset 8)

TMT-3-5-120.13618

(Subset 9)

TMT-3-5-121.14585 b) mixing the plurality of differentially labelled samples to form an analysis mixture comprising labelled analytes;

c) detecting the labelled analytes in a mass spectrometer;

d) dissociating the labelled analytes in the mass spectrometer to release the reporter moieties, and detecting complement ions comprising the remainder of the mass label attached to the analyte or a fragment of the analyte;

e) optionally one or more further steps of dissociating the complement ions formed in step d) to form fragments, and detecting the fragments;

f) identifying the analytes on the basis of the mass spectrum of the labelled analytes and/or the mass spectrum of the complement ions and/or fragments thereof.

11. A set of mass labels, wherein each mass label comprises the formula:

X-L-M-Re wherein:

X is a reporter moiety having an exact mass,

L is a bond cleavable by collision in a mass spectrometer,

M is a mass modifier, and

Re is a) a reactive functionality for attaching the mass label to an analyte or b) the analyte, wherein each mass label in the set has an integer mass, wherein each mass label in the set has the same integer mass, wherein the set comprises two or more subsets of mass labels, each subset comprising one, two or more mass labels, wherein, when the subset comprises two or more mass labels, the exact mass of the reporter moiety X of each mass label in the subset is different from the exact mass of the reporter moiety X of the mass labels in the same subset and in all other subsets, wherein each mass label is distinguishable by mass spectrometry, and the set consists of n=7 mass labels having the following structures:

(Subset 3)

TMT-2-7-115.11988

(Subset 4)

TMT-2-7-1-116.12323

(Subset 5)

TMT-2-7-1-117.12659

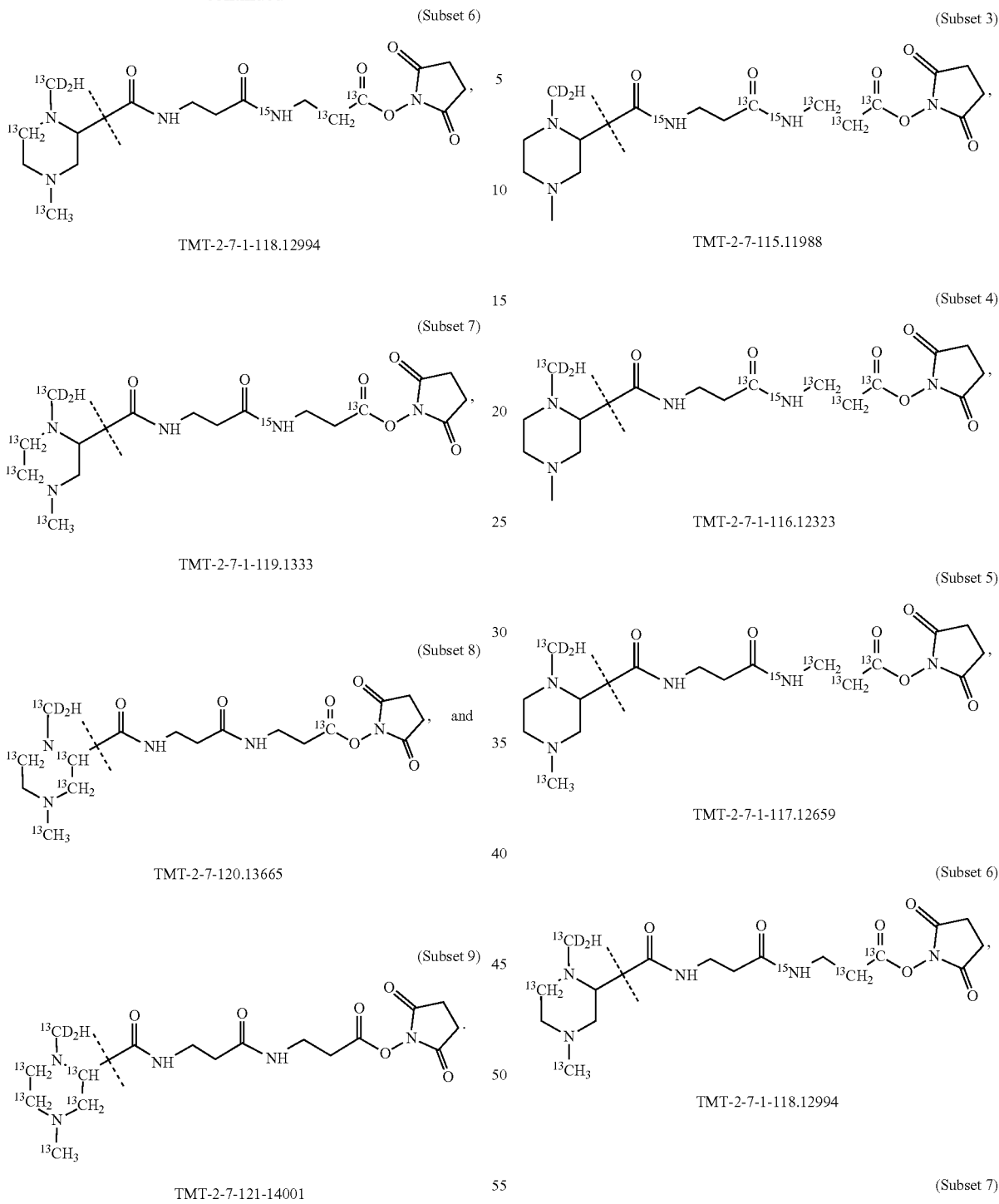

12. A method of mass spectrometry analysis, the method comprising:
a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=7 mass labels having the following structures:

-continued

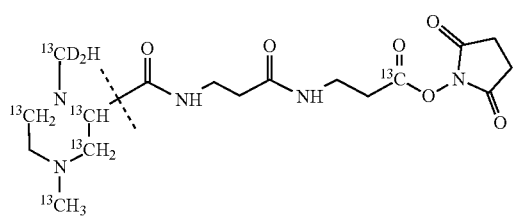

TMT-2-7-120.13665 and

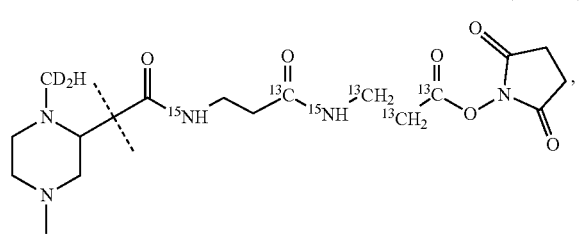

TMT-2-7-115.11988

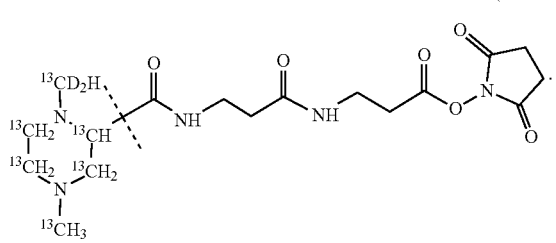

TMT-2-7-121-14001

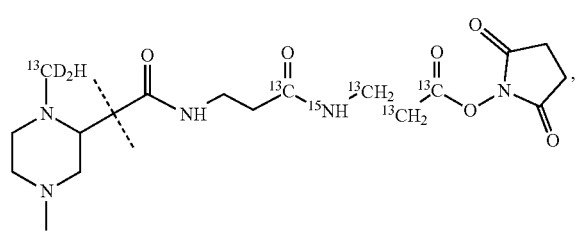

TMT-2-7-1-116.12323

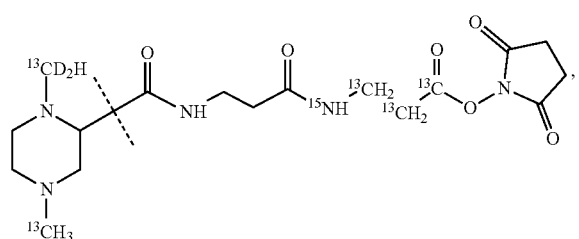

TMT-2-7-1-117.12659 b) mixing the plurality of differentially labelled samples to form an analysis mixture comprising labelled analytes;

c) optionally detecting the labelled analytes in a mass spectrometer;

d) dissociating the labelled analytes in the mass spectrometer to form mass labels and/or analyte fragments comprising intact mass labels;

e) detecting the mass labels and/or analyte fragments comprising intact mass labels;

f) optionally dissociating the mass labels in the mass spectrometer to release the reporter moieties, and detecting the reporter moieties;

g) optionally dissociating the reporter moieties formed in step f) to form fragments, and detecting the fragments;

h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

13. A method of mass spectrometry analysis, the method comprising:

a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=7 mass labels having the following structures:

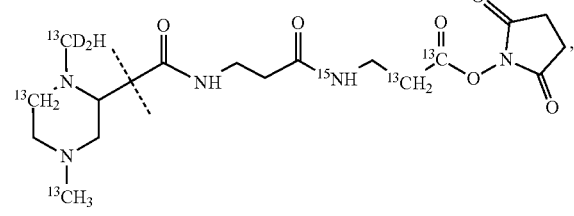

TMT-2-7-1-118.12994

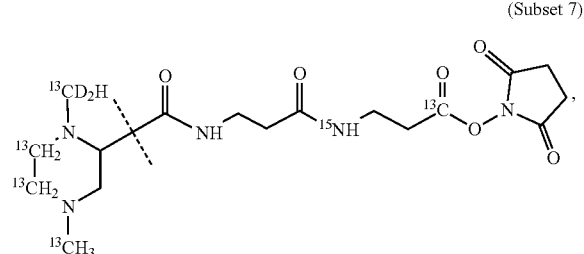

TMT-2-7-1-119.1333

-continued

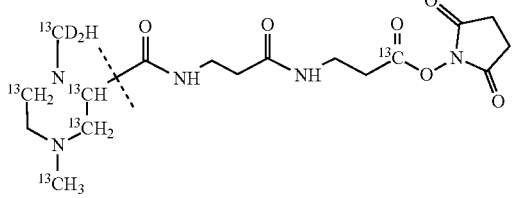

TMT-2-7-120.13665

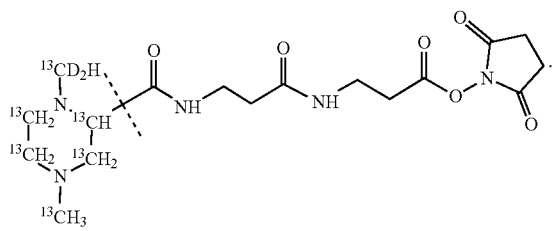

TMT-2-7-121-14001 b) mixing the plurality of differentially labelled samples to form an analysis mixture comprising labelled analytes;
c) detecting the labelled analytes in a mass spectrometer;
d) dissociating the labelled analytes in the mass spectrometer to release the reporter moieties, and detecting complement ions comprising the remainder of the mass label attached to the analyte or a fragment of the analyte;
e) optionally one or more further steps of dissociating the complement ions formed in step d) to form fragments, and detecting the fragments;
f) identifying the analytes on the basis of the mass spectrum of the labelled analytes and/or the mass spectrum of the complement ions and/or fragments thereof.

14. A set of two or more mass labels, wherein each mass label comprises the formula:

X-L-M-Re wherein:
X is a reporter moiety having an exact mass,
L is a bond cleavable by collision in a mass spectrometer,
M is a mass modifier, and
Re is a) a reactive functionality for attaching the mass label to an analyte or b) the analyte,
wherein each mass label in the set has an integer mass,
wherein each mass label in the set has the same integer mass,
wherein the set comprises two or more subsets of mass labels, each subset comprising one, two or more mass labels,
wherein, when the subset comprises two or more mass labels, the exact mass of the reporter moiety X of each mass label in the subset is different from the exact mass of the reporter moiety X of the mass labels in the same subset and in all other subsets,
wherein each mass label is distinguishable by mass spectrometry, and the set consists of n=21 mass labels having the following structures:

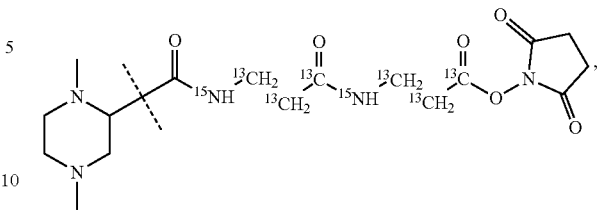

TMT-1-21-113.10732

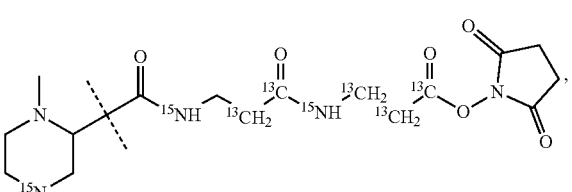

TMT-1-21-114.10436

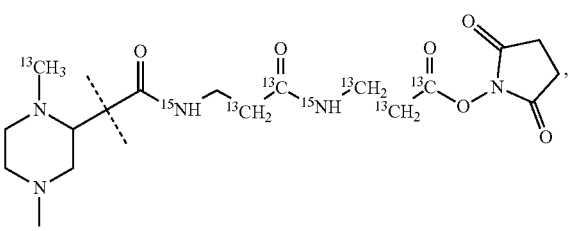

TMT-1-21-114.11068

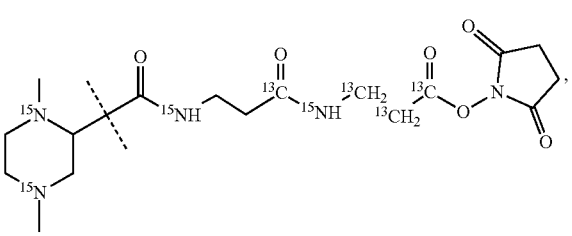

TMT-1-21-115.10139

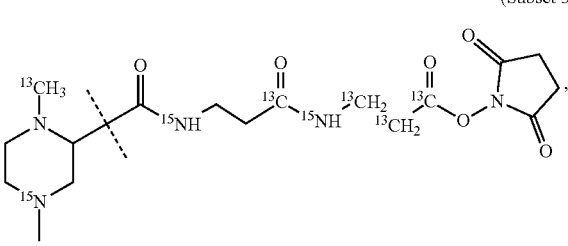

TMT-1-21-115.10771

(Subset 3)
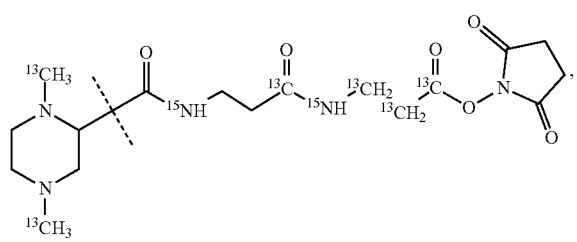
TMT-1-21-115.11403
(Subset 4)
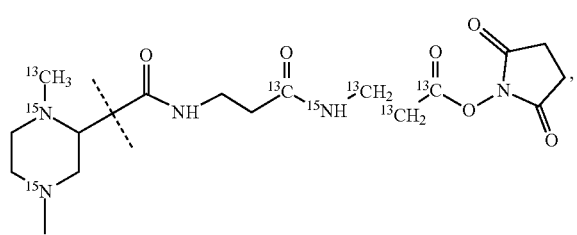
TMT-1-21-116.10475
(Subset 4)
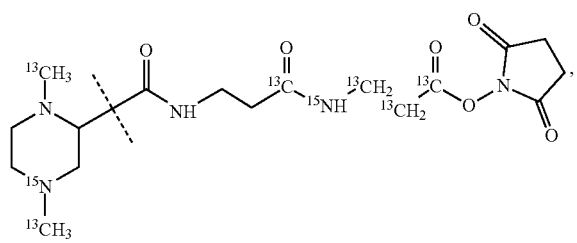
TMT-1-21-116.11107
(Subset 4)
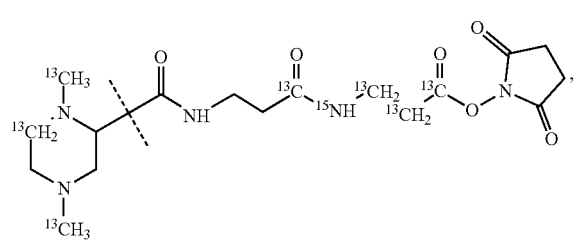
TMT-1-21-116.11739
(Subset 5)
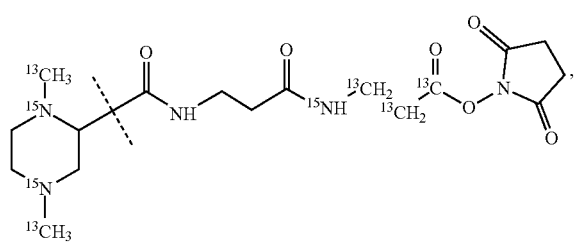
TMT-1-21-117.1081
(Subset 5)
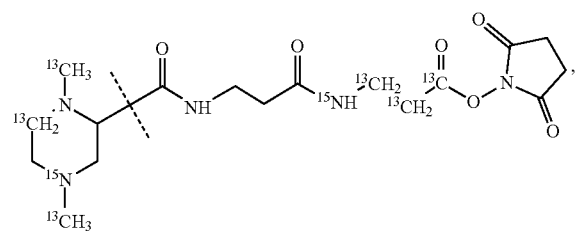
TMT-1-21-117.11442
(Subset 5)
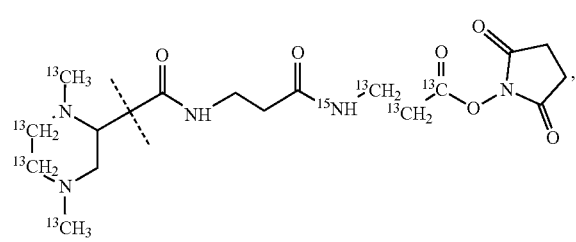
TMT-1-21-117.12074
(Subset 6)
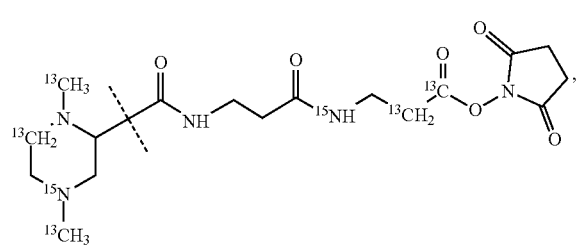
TMT-1-21-118.11146
(Subset 6)
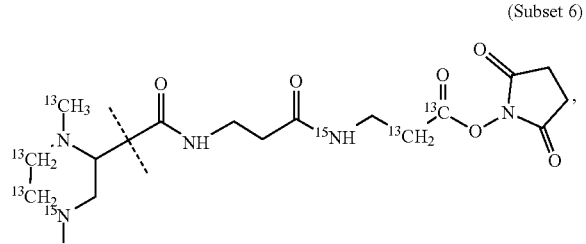
TMT-1-21-118.11778
(Subset 6)
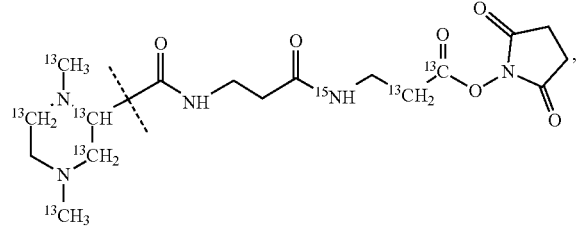
TMT-1-21-118.1241

-continued (Subset 7)

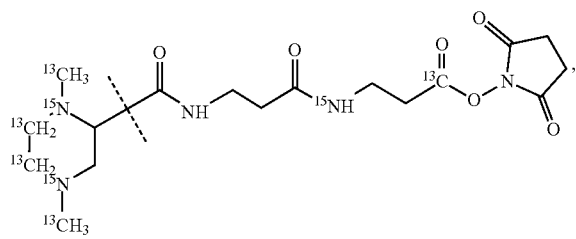

TMT-1-21-119.11481

(Subset 7)

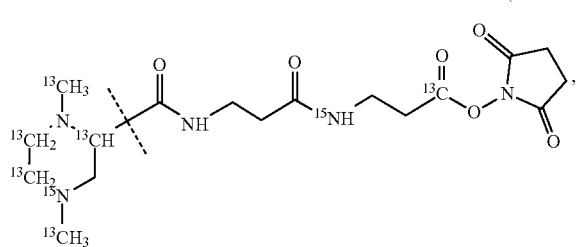

TMT-1-21-119.12113

(Subset 7)

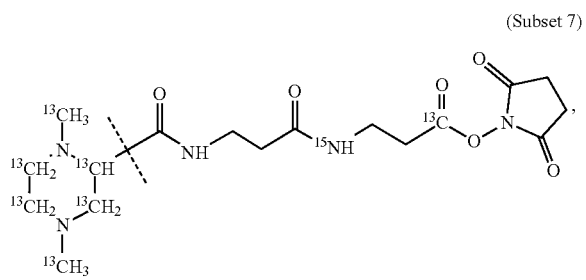

TMT-1-21-119.12745

(Subset 8)

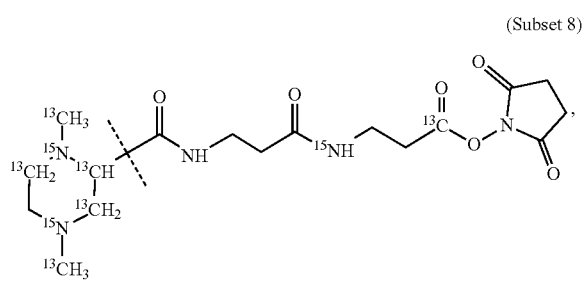

TMT-1-21-120.11817

(Subset 8)

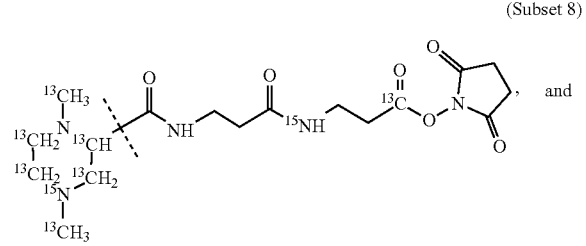

TMT-1-21-120.12449

, and

-continued (Subset 9)

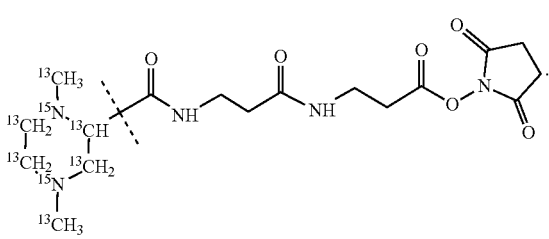

TMT-1-21-121.12152

15. A method of mass spectrometry analysis, the method comprising:
  a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=21 mass labels having the following structures:

(Subset 1)

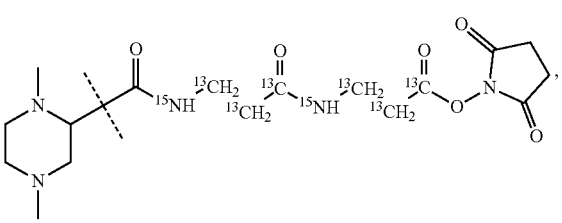

TMT-1-21-113.10732

(Subset 2)

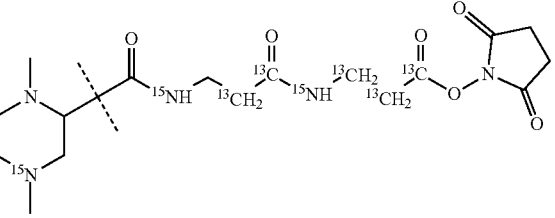

TMT-1-21-114.10436

(Subset 2)

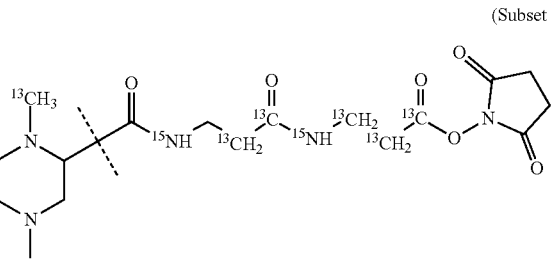

TMT-1-21-114.11068

(Subset 3)
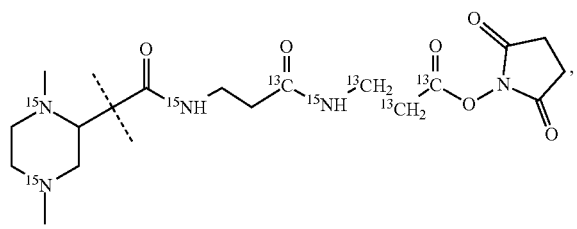
TMT-1-21-115.10139
(Subset 4)
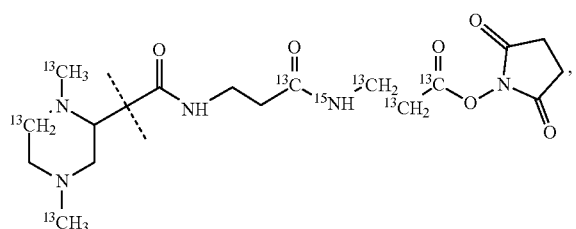
TMT-1-21-116.11739
(Subset 3)
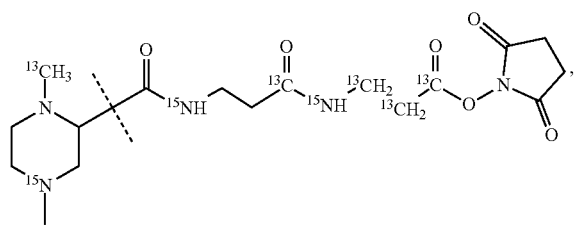
TMT-1-21-115.10771
(Subset 5)
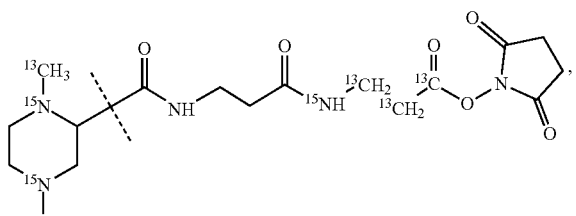
TMT-1-21-117.1081
(Subset 3)
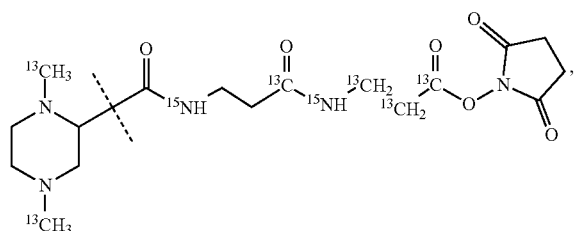
TMT-1-21-115.11403
(Subset 5)
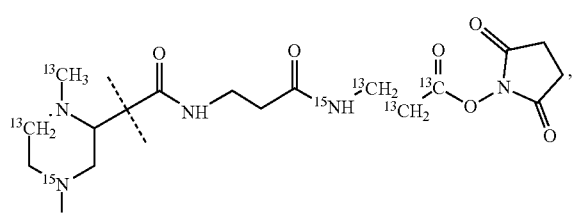
TMT-1-21-117.11442
(Subset 4)
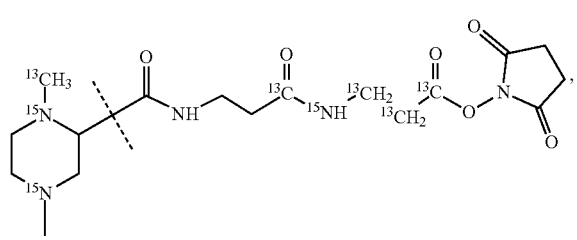
TMT-1-21-116.10475
(Subset 5)
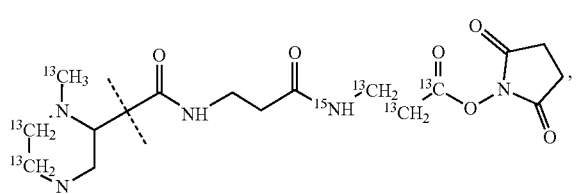
TMT-1-21-117.12074
(Subset 4)
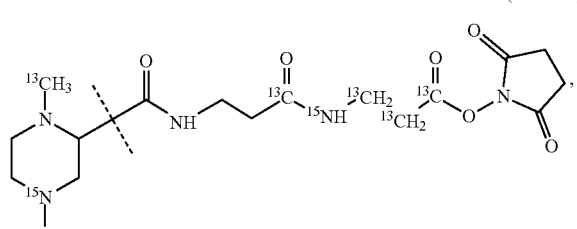
TMT-1-21-116.11107
(Subset 6)
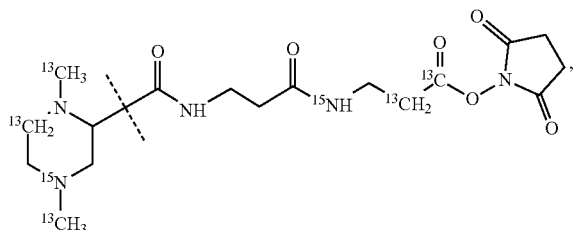
TMT-1-21-118.11146

-continued

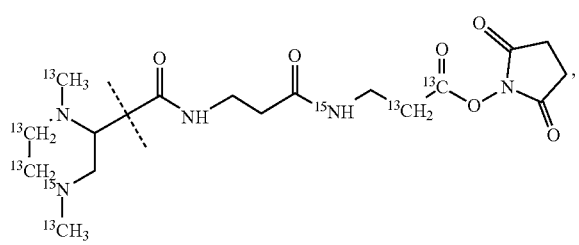

TMT-1-21-118.11778 (Subset 6)

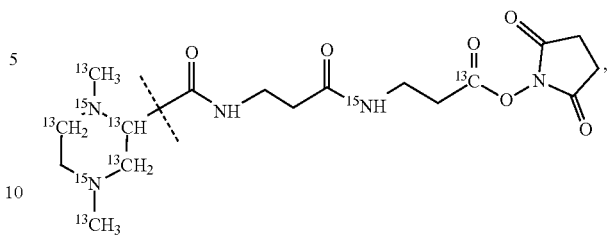

TMT-1-21-120.11817 (Subset 8)

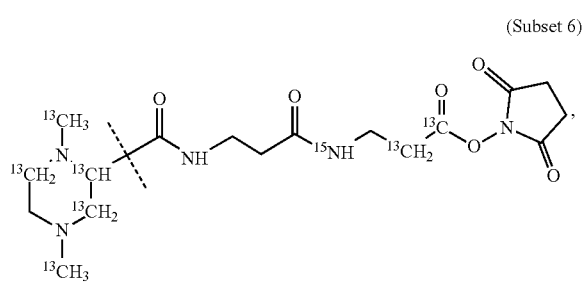

TMT-1-21-118.1241 (Subset 6)

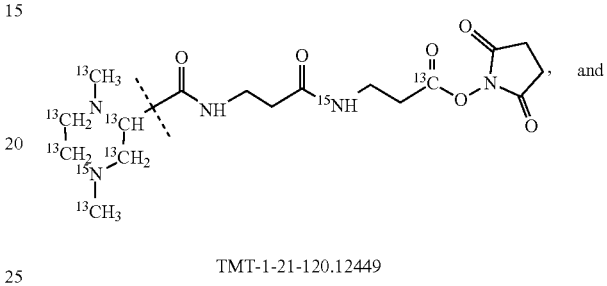

TMT-1-21-120.12449 (Subset 8), and

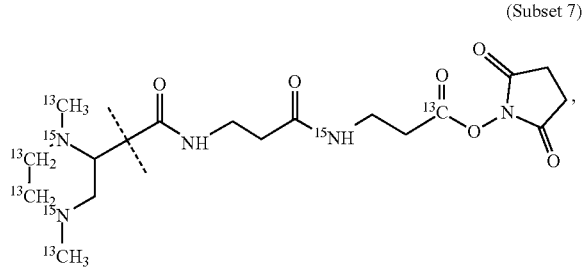

TMT-1-21-119.11481 (Subset 7)

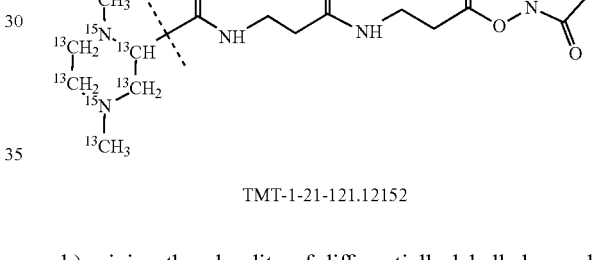

TMT-1-21-121.12152 (Subset 9)

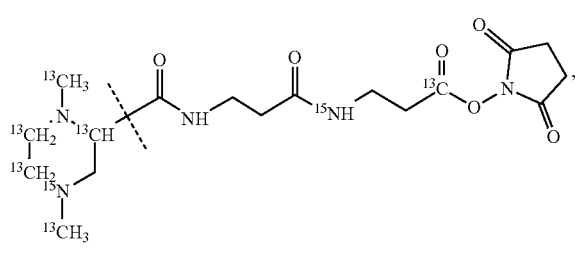

TMT-1-21-119.12113 (Subset 7)

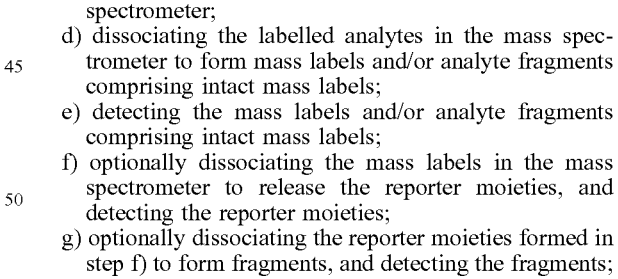

TMT-1-21-119.12745 (Subset 7)

b) mixing the plurality of differentially labelled samples to form an analysis mixture comprising labelled analytes;

c) optionally detecting the labelled analytes in a mass spectrometer;

d) dissociating the labelled analytes in the mass spectrometer to form mass labels and/or analyte fragments comprising intact mass labels;

e) detecting the mass labels and/or analyte fragments comprising intact mass labels;

f) optionally dissociating the mass labels in the mass spectrometer to release the reporter moieties, and detecting the reporter moieties;

g) optionally dissociating the reporter moieties formed in step f) to form fragments, and detecting the fragments;

h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

16. A method of mass spectrometry analysis the method comprising:

a) providing a plurality of samples, each sample comprising one or more analytes, wherein each sample is differentially labelled with a mass label or a combination of mass labels, obtaining one or more labelled analytes, wherein the one or more labelled analytes are labelled with a set of n=21 mass labels having the following structures:

(Subset 1)
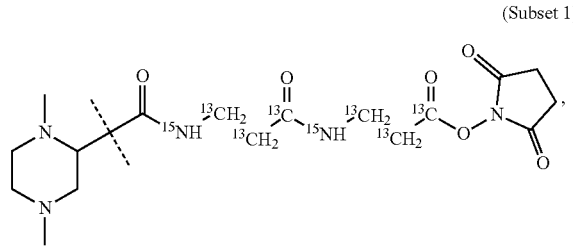
TMT-1-21-113.10732
(Subset 2)
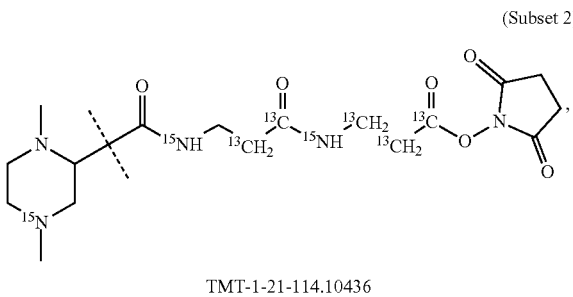
TMT-1-21-114.10436
(Subset 2)
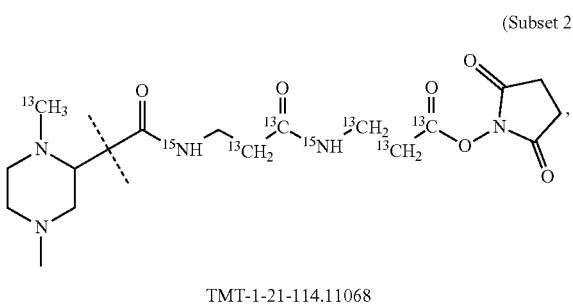
TMT-1-21-114.11068
(Subset 3)
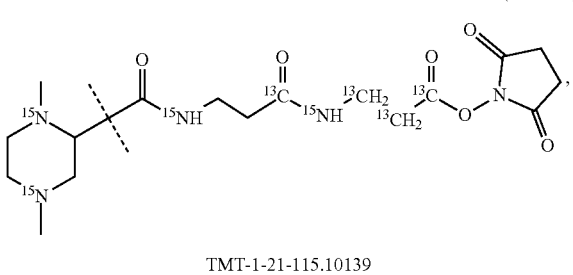
TMT-1-21-115.10139
(Subset 3)
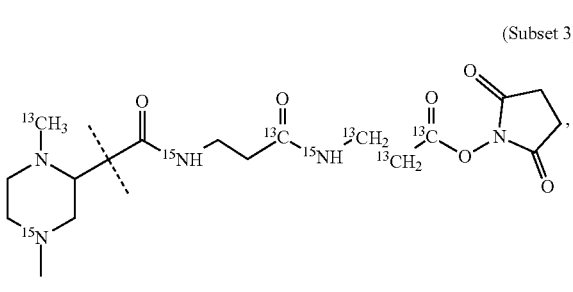
TMT-1-21-115.10771
-continued
(Subset 3)
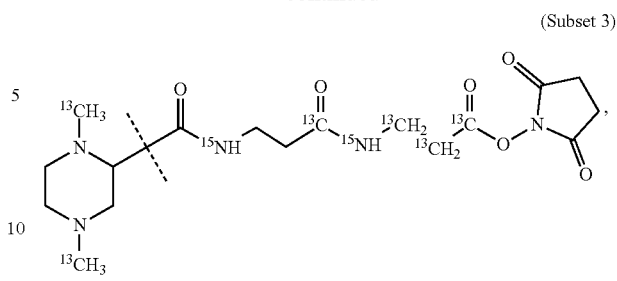
TMT-1-21-115.11403
(Subset 4)
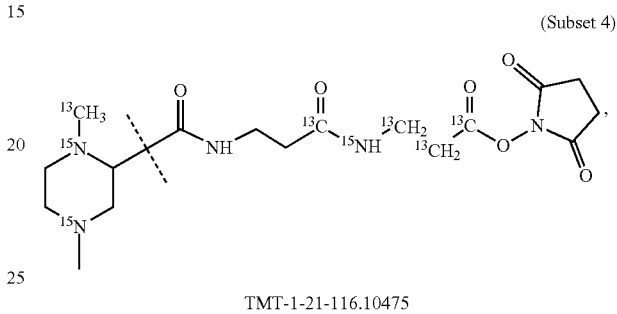
TMT-1-21-116.10475
(Subset 4)
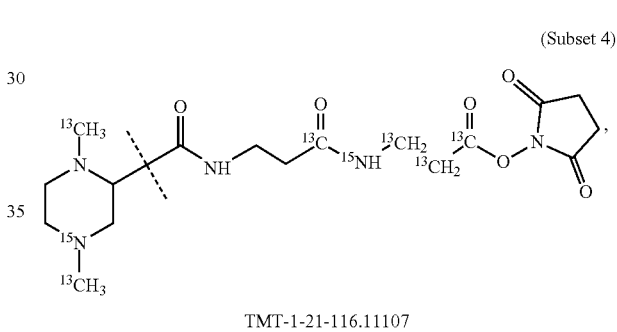
TMT-1-21-116.11107
(Subset 4)
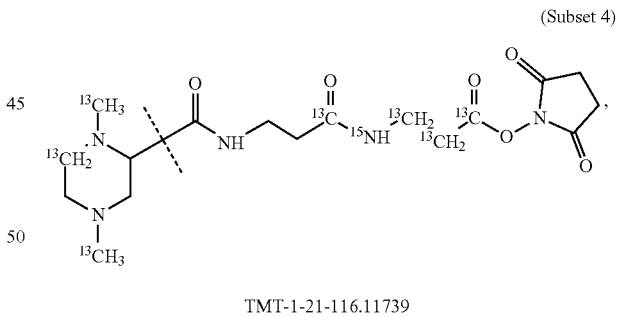
TMT-1-21-116.11739
(Subset 5)
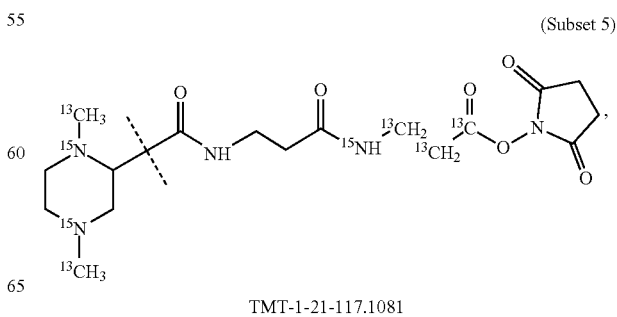
TMT-1-21-117.1081

(Subset 5)
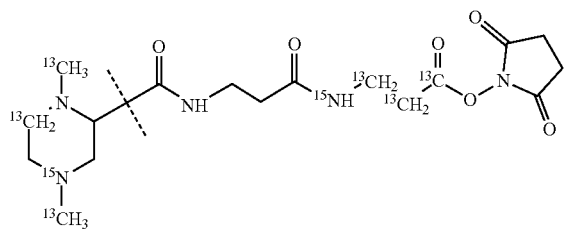
TMT-1-21-117.11442
(Subset 5)
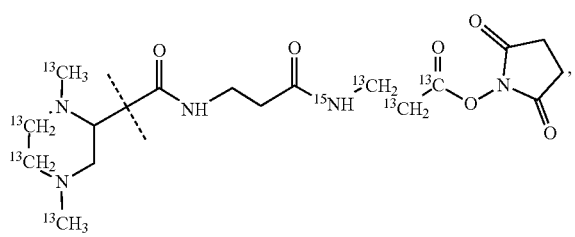
TMT-1-21-117.12074
(Subset 6)
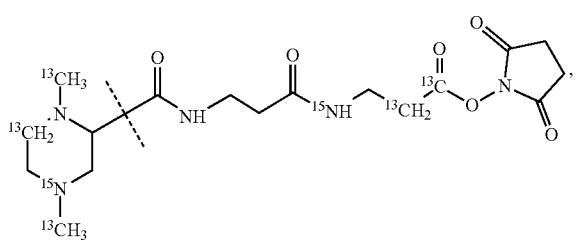
TMT-1-21-118.11146
(Subset 6)
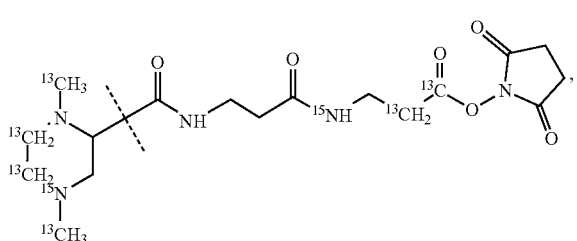
TMT-1-21-118.11778
(Subset 6)
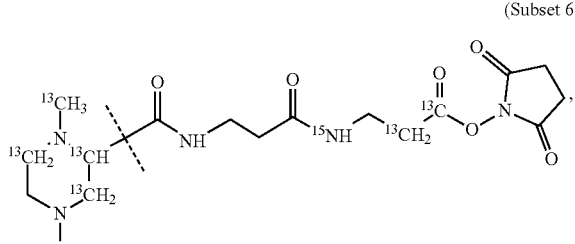
TMT-1-21-118.1241
(Subset 7)
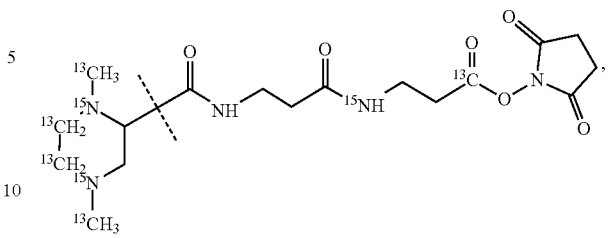
TMT-1-21-119.11481
(Subset 7)
TMT-1-21-119.12113
(Subset 7)
TMT-1-21-119.12745
(Subset 8)
TMT-1-21-120.11817
(Subset 8)
TMT-1-21-120.12449

-continued (Subset 9)

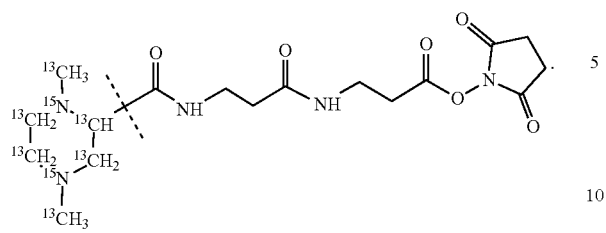

TMT-1-21-121.12152 b) mixing the plurality of differentially labelled samples to form an analysis mixture comprising labelled analytes;
c) detecting the labelled analytes in a mass spectrometer;
d) dissociating the labelled analytes in the mass spectrometer to release the reporter moieties, and detecting complement ions comprising the remainder of the mass label attached to the analyte or a fragment of the analyte;
e) optionally one or more further steps of dissociating the complement ions formed in step d) to form fragments, and detecting the fragments;
f) identifying the analytes on the basis of the mass spectrum of the labelled analytes and/or the mass spectrum of the complement ions and/or fragments thereof.

\* \* \* \* \*